US012344904B2

(12) United States Patent
Huygens

(10) Patent No.: US 12,344,904 B2
(45) Date of Patent: Jul. 1, 2025

(54) BIOMARKERS AND USES THEREOF

(71) Applicant: Microbio Pty Ltd, Westlake (AU)

(72) Inventor: Flavia Huygens, Westlake (AU)

(73) Assignee: Microbio Pty Ltd, Westlake (AU)

(*) Notice: Subject to any disclaimer, the term of this patent is extended or adjusted under 35 U.S.C. 154(b) by 182 days.

(21) Appl. No.: 18/355,932

(22) Filed: Jul. 20, 2023

(65) Prior Publication Data
US 2024/0141443 A1 May 2, 2024

Related U.S. Application Data

(62) Division of application No. 16/614,697, filed as application No. PCT/AU2018/050471 on May 17, 2018, now Pat. No. 11,739,389.

(30) Foreign Application Priority Data

May 17, 2017 (AU) ................. 2017901846

(51) Int. Cl.
C12Q 1/68 (2018.01)
C12Q 1/686 (2018.01)
C12Q 1/689 (2018.01)
C12Q 1/6895 (2018.01)

(52) U.S. Cl.
CPC ............. *C12Q 1/689* (2013.01); *C12Q 1/686* (2013.01); *C12Q 1/6895* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 4,656,127 A | 4/1987 | Mundy |
| 5,002,867 A | 3/1991 | Macevicz |
| 5,143,854 A | 9/1992 | Pirrung et al. |
| 5,422,252 A | 6/1995 | Walker et al. |
| 5,424,186 A | 6/1995 | Fodor et al. |
| 5,445,934 A | 8/1995 | Fodor et al. |
| 5,589,136 A | 12/1996 | Northrup et al. |
| 5,631,734 A | 5/1997 | Stern et al. |
| 6,134,854 A | 10/2000 | Stanchfield |
| 6,294,336 B1 | 9/2001 | Boyce-Jacino et al. |
| 7,381,547 B2 | 6/2008 | Tsang et al. |
| 7,864,230 B2 | 1/2011 | Sugita |
| 8,741,565 B2 | 6/2014 | Gu et al. |
| 2004/0010129 A1 | 1/2004 | Hsu et al. |
| 2004/0241643 A1 | 12/2004 | Yamamoto et al. |
| 2005/0142584 A1 | 6/2005 | Wilson et al. |
| 2008/0199863 A1 | 8/2008 | Haake et al. |
| 2016/0068897 A1 | 3/2016 | Talebpour et al. |
| 2016/0145696 A1 | 5/2016 | Brandon et al. |

FOREIGN PATENT DOCUMENTS

| CN | 1683565 | 10/2005 |
| CN | 1746319 | 3/2006 |
| CN | 1291997 C | 12/2006 |
| CN | 103436429 A | 12/2013 |
| CN | 103614326 | 3/2014 |
| CN | 103952417 A | 7/2014 |
| CN | 104372072 A | 2/2015 |
| CN | 105483251 | 4/2016 |
| EP | 0332435 | 9/1989 |
| EP | 0785280 A2 | 7/1997 |
| EP | 1464710 A2 | 10/2004 |
| EP | 1953247 A1 | 8/2008 |
| EP | 1997905 A1 | 12/2008 |
| JP | 2003-284559 | 10/2003 |
| JP | 2007-014351 | 1/2007 |
| KR | 10-2013-0046321 | 5/2013 |
| WO | WO 89/10414 | 11/1989 |
| WO | WO 91/02087 | 2/1991 |
| WO | WO 92/01813 | 2/1992 |
| WO | WO 92/10092 | 6/1992 |
| WO | WO 92/15712 | 9/1992 |
| WO | WO 95/11995 | 5/1995 |
| WO | WO 95/25116 | 9/1995 |
| WO | WO 95/35505 | 12/1995 |
| WO | WO 97/19193 | 5/1997 |
| WO | WO 2002/10444 A1 | 2/2002 |

(Continued)

OTHER PUBLICATIONS

Bujold & MacInnes, Validation of reference genes for quantitative real-time PCR (qPCR) analysis of Actinobacillus suis, BMC Res Notes. Mar. 18, 2015;8:86. doi: 10.1186/s13104-015-1045-8.*

(Continued)

*Primary Examiner* — Aaron A Priest
(74) *Attorney, Agent, or Firm* — Klarquist Sparkman, LLP

(57) ABSTRACT

The present invention generally relates to methods and agents for identifying and/or classifying microbes (especially bacteria), yeast organisms and filamentous fungi. In particular, the present invention concerns the discovery of unique single nucleotide polymorphisms (SNPs) in bacterial 16S ribosomal RNA (16S rRNA) and yeast organism and filamentous fungi 18S ribosomal RNA, and methods of classifying and/or identifying bacteria, yeast organisms and/or filamentous fungi in a sample based on the presence of one or more of those SNPs. The present invention also concerns probes, primers and kits that are useful in those method.

8 Claims, 26 Drawing Sheets
Specification includes a Sequence Listing.

(56) References Cited

FOREIGN PATENT DOCUMENTS

| WO | WO 2003/079241 A1 | 9/2003 |
|---|---|---|
| WO | WO 2003/106676 A1 | 12/2003 |
| WO | WO 2008/054432 A2 | 5/2008 |
| WO | WO 2011/103274 A1 | 8/2011 |
| WO | WO 2012/080754 A2 | 6/2012 |
| WO | WO 2012/110822 | 8/2012 |
| WO | WO 2012/139122 | 10/2012 |
| WO | WO 2013/036928 | 3/2013 |
| WO | WO 2014/190394 | 12/2014 |
| WO | WO 2015095796 A1 | 6/2015 |
| WO | WO 2016/012508 A1 | 1/2016 |
| WO | WO 2016/013940 A2 | 1/2016 |
| WO | WO 2016/193351 | 12/2016 |

OTHER PUBLICATIONS

Fernández-No, et al. "Identification of single nucleotide polymorphisms (SNPs) in the 16S rRNA gene of foodborne *Bacillus* spp," *Food Microbiol.* 46:239-245, 2015.

Andersson et al., "Analysis of blaSHV Codon 238 and 240 Allele Mixtures Using Sybr Green High-Resolution Melting Analysis," *Antimicrob Agents Chemother.* 53(6):2679-2683, Jun. 2009.

Applied Biosystems, "A Guide to High Resolution Melting (HRM) Analysis," available at https://tools.thermofisher.cn/content/sfs/manuals/cms_070283.pdf, 20 pages, 2010.

Chee et al., "Accessing Genetic Information with High-Density DNA Arrays," *Science* 274(5287): 610-614, Oct. 1996.

Cotton et al., "Reactivity of cytosine and thymine in single-base-pair mismatches with hydroxylamine and osmium tetroxide and its application to the study of mutations," *Proc Natl Acad Sci. USA* 85(12): 4397-4401, Jun. 1988.

Derisi et al, "Use of cDNA microarray to analyse gene expression patterns in human cancer," *Nat Genet.* 14: 457-460, Dec. 1996.

Derisi et al., "Exploring the Metabolic and Genetic Control of Gene Expression on a Genomic Scale," *Science* 278(5338): 680-686, Oct. 1997.

Devereux et al., "A comprehensive set of sequence analysis programs for the VAX," *Nucleic Acids Research* 12(1): 387-395, 1984.

Drmanac et al., "Accurate sequencing by hybridization for DNA diagnostics and individual genomics," *Nature Biotech.* 16: 54-58, Jan. 1998.

El-Bahy, et al. "New approach to molecular characterization of *Paramphistomum cervi* and *Carmyerius gregarius* and comparative analyses with selected trematodes," *Parasitol Res.*, 116(5):1417-1422, ePub Dec. 2016.

Fluit et al., "Molecular Detection of Antimicrobial Resistance," *Clin Microbial Rev*, 14(4): 836-871, 2001.

Gibbs et al., "Detection of single DNA base differences by competitive oligonucleotide priming," *Nucleic Acids Research* 17(7): 2437-2448, 1989.

Hacia et al., "Detection of heterozygous mutations in BRCA1 using high density oligonucleotide arrays and two-colour fluorescence analysis," *Nat Genet.* 14: 441-447, Dec. 1996.

Hakovirta, Jr., et al. "Identification and Analysis of Informative Single Nucleotide Polymorphisms in 16S rRNA Gene Sequences of the *Bacillus cereus* Group," *J. Clin. Microbial*, 54(11):2749-2756, 2016.

Imajoh, et al., "Genotypic characteristics of a *Mycobacterium* sp. Isolated from yellowtail *Seriola quinqueradiata* and striped jack *Pseudocaranx dentex* in Japan," *Microbiology and Immunology*, 57(1):13-20, 2013.

Jobs et al., "DASH-2: Flexible, Low-Cost, and High-Throughput SNP Genotyping by Dynamic Allele-Specific Hybridization on Membrane Arrays," *Genome Res.* 13(5): 916-924, 2003.

Kagkli et al, "Towards a Pathogenic *Escherichia coli* Detection Platform Using Multiplex SYBR®Green Real-Time PCR Methods and High Resolution Melting Analysis," *PLoS One* 7(6): e39287, 2012.

Karlowsky et al. "Prevalence and antimicrobial susceptibilities of bacteria isolated from blood cultures of hospitalized patients in the United States in 2002," *Ann Clin Microbiol Antimicrob.* 3:7, May 2004.

Kornher and Livak, "Mutation detection using nucleotide analogs that alter electrophoretic mobility," *Nucl Acids Res.* 17(19): 7779-7784, 1989.

Kumar and Song, "Polymorphisms of the CB2 Cannabinoid Receptor," *Handbook of Cannabis and Related Pathologies Biology, Academic Press*, pp. 584-591, 2017.

Kuppuswamy et al., "Single nucleotide primer extension to detect genetic diseases: Experimental application to hemophilia B (factor IX) and cystic fibrosis genes," *Proc Natl Acad Sci. USA* 88(4): 1143-1147, Feb. 1991.

Liu et al, "Rolling Circle DNA Synthesis: Small Circular Oligonucleotides as Efficient Templates for DNA Polymerases," *J Am Chem Soc.* 118(7): 1587-1594, Feb. 1996.

Lucignano et al., "Multiplex PCR Allows Rapid and Accurate Diagnosis of Bloodstream Infections in Newborns and Children with Suspected Sepsis," *J Clin Microbiol.* 49(6): 2252-2258, Jun. 2011.

Marques, et al., "Intraspecific sequence variation in 16S rRNA gene of *Ureaplasma diversum* isolates," *Veterinary Microbiology* 152(1-2):205-211, 2011.

Maxam and Gilbert, "A new method for sequencing DNA," *Proc Natl Acad Sci. USA* 74(2): 560-564, Feb. 1977.

Merchant-Patel et al, "*Campylobacter jejuni* and *Campylobacter coli* Genotyping by High-Resolution Melting Analysis of a flaA Fragment," *Applied and Environmental Microbiology* 76(2): 493-499, Epub Nov. 2009.

Merchant-Patel et al., "Characterisation of chicken *Campylobacter jejuni* isolates using resolution optimised single nucleotide polymorphisms and binary gene markers," *Int J Food Microbiol.* 128(2):304-308, 2008.

Modrich, "Mechanisms and Biological Effects of Mismatch Repair," *Ann Rev Genet.* 25: 229-253, 1991.

Moro et al., "Bacterial taxa associated with the hematophagous mite *Dermanyssus gallinae* detected by 16S rRNA PCR amplification and TTGE fingerprinting," *Res Microbiol.* 160(1): 63-70, Epub Nov. 2008.

Nagamine et al., "A PCR Artifact: Generation of Heteroduplexes," *Am J Hum Genet.* 45(2): 337-339, 1989.

Newton et al., "Analysis of any point mutation in DNA. The amplification refractory mutation system (ARMS)," *Nucl Acids Res.* 17(7): 2503-2516, 1989.

Nolan et al., "Quantification of mRNA using real-time RT-PCR," *Nature Protocols*, 1(3): 1559-1582, 2006.

Novack et al., "Detection of single base-pair mismatches in DNA by chemical modification followed by electrophoresis in 15% polyacrylamide gel," *Proc Natl Acad Sci. USA* 83(3): 586-590, Feb. 1986.

Nucleotide sequence of accession No. EF674493, Uncultured *Staphylococcus* sp. isolate TTGE gel band 11 16S (1 page), 2009.

Orita et al., "Detection of polymorphisms of human DNA by gel electrophoresis as single-strand conformation polymorphisms," *Proc Natl Acad Sci USA* 86(8): 2766-2770, Apr. 1989.

Price et al., "Fingerprinting of Campylobacter jejuni by Using Resolution-Optimized Binary Gene Targets Derived from Comparative Genome Hybridization Studies," *Appl Environ Microbiol.* 72(12): 7793-7803, 2006.

Prince et al., "Robust and Accurate Single Nucleotide Polymorphism Genotyping by Dynamic Allele-Specific Hybridization (DASH): Design Criteria and Assay Validation," *Genome Res.* 11(1): 152-162, 2001.

Reinhart et al., "New Approaches to Sepsis: Molecular Diagnostics and Biomarkers," *Clinical Microbiology Reviews* 25(4): 609-634, Oct. 2012.

Salimullah et al., "Efficient SNP Analysis Enabled by Joint Application of the μTGGE and Heteroduplex Methods," *Cellular and Mol Biol Letts.* 10(2): 237-245, 2005.

Schena et al., "Quantitative Monitoring of Gene Expression Patterns with a Complementary DNA Microarray," *Science* 270(5235): 467-470, Oct. 1995.

(56) References Cited

OTHER PUBLICATIONS

Shalon et al., "A Dna Microarray System for Analyzing Complex DNA Samples using Two-Color Fluorescent Probe Hybridization," *Genome Res.* 6(7): 639-645, 1996.

Sheffield et al., "Attachment of a 40-base-pair G+C-rich sequence (GC-clamp) to genomic DNA fragments by the polymerase chain reaction results in improved detection of single-base changes" *Proc Natl Acad Sci. USA* 86(1): 232-236, Jan. 1989.

Shenk et al., "Biochemical Method for Mapping Mutational Alterations in DNA with S1 Nuclease: The Location of Deletions and Temperature-Sensitive Mutations in Simian Virus 40," *Proc Natl Acad Sci. USA* 72(3): 989-993, Mar. 1975.

Shoemaker et al., "Quantitative phenotypic analysis of yeast deletion mutants using a highly parallel molecular bar-coding strategy," *Nat Genet.* 14(4): 450-456, Dec. 1996.

Sokolov, "Primer extension technique for the detection of single nucleotide in genomic DNA," *Nucl Acids Res.* 18(12): 3671, 1990.

Stephens et al., "High-Resolution Melting Analysis of the spa Repeat Region of *Staphylococcus aureus,*" *Clinical Chemistry* 54(2): 432-436, Feb. 2008.

Syvanen et al., "Identification of Individuals by Analysis of Biallelic DNA Markers, Using PCR and Solid-Phase Minisequencing," *Amer J Hum Genet.* 52(1): 46-59, 1993.

Syvanen, "Accessing Genetic Variation: Genotyping Single Nucleotide Polymorphisms," *Nat Rev Genet.* 2(12): 930-942, Dec. 2001.

Thelwell et al., "Mode of action and application of Scorpion primers to mutation detection," *Nucleic Acid Res.* 28(19): 3752-3761, 2000.

Tong et al., "Microbiological Applications of High-Resolution Melting Analysis," *J Clin Microbial,* 50(11): 3418-3421, 2012.

Tyagi et al., "Extremely sensitive, background-free gene detection using binary probes and Qβ replicase," *Proc Natl Acad Sci. USA* 93(11): 5395-5400, May 1996.

Wartell et al., "Detecting base pair substitutions in DNA fragments by temperature-gradient gel electrophoresis," *Nucl Acids Res.* 18(9): 2699-2705, 1990.

Wei et al., "Profiling and Identification of Small rDNA-Derived RNAs and Their Potential Biological Functions," *PLoS One* 8(2): e56842, 2013.

Weisburg et al., "16S Ribosomal DNA Amplification for Phylogenetic Study," *Journal of Bacteriology* 173(2): 697-703, Jan. 1991.

Xiao and Kwok, "DNA Analysis by Fluorescence Quenching Detection," *Genome Research* 13(5): 932-939, 2003.

* cited by examiner

| | |
|---|---|
| Staphylococcus aureus | TTTATGGAGAGTTTGATCCTGGCTCAGGATGAACGCTGGCGGCGTGCCTAATACATGCA |
| Staphylococcus epidermidis | TTTATGGAGAGTTTGATCCTGGCTCAGGATGAACGCTGGCGGCGTGCCTAATACATGCA |
| Streptococcus pneumoniae | ----------GTTTGATCCTGGCTCAGGACGAACGCTGGCGGCGTGCCTAATACATGCA |
| Streptococcus agalactiae | ----------------GACGAACGCTGGCGGCGTGCCTAATACATGCA |
| Streptococcus pyogenes | ----------GAGAGTTTGATCCTGGCTCAGGACGAACGCTGGCGGCGTGCCTAATACATGCA |
| Enterococcus faecalis | ----------AGAGTTTGATCCTGGCTCAGGACGAACGCTGCCGGCGTGCCTAATACATGCA |
| Enterococcus faecium | ----------AGAGTTTGATCCTGGCTCAGGACGAACGCTGCCGGCGTGCCT-ATACATGCA |
| Proteus mirabilis | ---AATTGAAGAGTTTGATCATGGCTCAGATTGAACGCTGGCGGCAGGCCTAACACATGCA |
| Escherichia coli | -AAATTGAAGAGTTTGATCATGGCTCAGATTGAACGCTGGCGGCAGGCCTAACACATGCA |
| Serratia marcescens | -----------GCTCAGATTGAACGCTGGCGGCAGGCCTAACACATGCA |
| Enterobacter aerogenes | --------------ACGCTGGCGGCAGGCCTAACACATGCA |
| Enterobacter cloacae | -------------TGAACGCTGGCGGCAGGCCTAACACATGCA |
| Klebsiella pneumoniae | ----------AGAGTTTGATNNTGGCTCAGATTGAACGCTGGCGGCAGGCCTAACACATGCA |
| Pseudomonas aeruginosa | -GAACTGAAGAGTTTGATCATGGCTCAGATTGAACGCTGGCGGCAGGCCTAACACATGCA |
| Acinetobacter calcoaceticus | ----TAGAGTTTGATCCTGGCTCAGATTGAACGCTGGCGGCAGGCCTTAACACATGCA |
| | ********** ** * * ******* |
| | |
| Staphylococcus aureus | AGTCGAGCGAACGGACGAGAGAAGCTTG------------CTTCTCTGATGTTAGCGGCGGACG |
| Staphylococcus epidermidis | AGTCGAGCGAACAGACAGAGAGGAGCTTG-----------CTTCTCTGACGTTAGCGGCGGACG |
| Streptococcus pneumoniae | AGTAGAACGCTGAAGGAGGAGCTT----------GCTTCTCTGGATGAGTGAGTTGCGAACG |
| Streptococcus agalactiae | AGTAGAACGCTCAGGTTTGGTGTT----------ACACTAGACTGATGAGTTGCGAACG |
| Streptococcus pyogenes | AGTAGAACGCTGAGAACTGGTGCTT-----------GCACCGGTTCAAGGAGTTGCGAACG |
| Enterococcus faecalis | AGTCGAACGCTTCTTTCCTCCCGAGTGCTTGCACTCAATTGGAAAGAGGAGTGGCGGACG |
| Enterococcus faecium | AGTCGAACGCTTCTTTTTCCACCGGAGCTTGCTCCACCGGAAAAAGAGGAGTGGCGAACG |
| Proteus mirabilis | AGTCGAGCGGTAACAGGAGAAAGCTTGCTTTCTTGC--------TGACGAGCGGCGGACG |
| Escherichia coli | AGTCGAACGGTAACAGGAAGAAGCTTGCTTCTTTGC--------TGACGAGTGGCGGACG |
| Serratia marcescens | AGTCGAGCGGTAGCACAGAGAGCTTGCTCTCGGG---------TGACGAGCGGCGGACG |
| Enterobacter aerogenes | AGTCGAGCGGTAGCACAGAGAGCT--TGCTCTCGGG------TGACGAGTGGCGGACG |
| Enterobacter cloacae | AGTCGAGCGGTAGCACAGAGAGCT--TGCTCTCGGG------TGACGAGCGGCGGACG |
| Klebsiella pneumoniae | AGTCGAGCGGTAGCACAGAGAGCTTGCTCTCGGG--------TGACGAGCGGCGGACG |
| Pseudomonas aeruginosa | AGTCGAGCGGATGAAGGGAGCTTGCT-----CCTG---------GATTCAGCGGCGGACG |
| Acinetobacter calcoaceticus | AGTCGAGCGGGGAAAGGTAGCTTGCT-----ACTG---------GACCTAGCGGCGGACG |
| | *** **** ** *** *** |

Figure 1A

| Species | Sequence block 1 | Sequence block 2 |
|---|---|---|
| Staphylococcus aureus | GGTGAGTAACACGTGGATAACCTACCTATAAGACTGGGATAACTTCGGGAAACCGGAGCT | AATACCGGATAATATTTTGAACCGCATGGTTCAAAAGTGA------AAGACGGTCTTGCTGTCA |
| Staphylococcus epidermidis | GGTGAGTAACACGTGGATAACTTACCTATAAGACTGGGATAACTTCGGGAAACCGGAGCT | AATACCGGATAATATATTGAACCGCATGGTTCAATAGTGA------AAGACGGTTTGCTGTCA |
| Streptococcus pneumoniae | GGTGAGTAACGCGTAGGTAACCTGCCTGGTAGCGGGGGATAACTATTGGAAACGATAGCT | AATACCGCATAAGAGTGGATCGTTGCATGACAT-TTGCTTAAAA--GGTGCACTTGCATCA |
| Streptococcus agalactiae | GGTGAGTAACGCGTAGGTAACCTGCCTAACCTGCCTCATAGCGGGGGATAACTATTGGAAACGATAGCT | AATACCGCATAAGAGTAATTAACACATGTTAG-TTATTTAAAA--GGAGCAATTGCTTCA |
| Streptococcus pyogenes | GGTGAGTAACGCGTAGGTAACCTGCCTAACCTACCCATAGGGGGATAACTATTGGAAACGATAGCT | AATACCGCATAAGAGAGACTAACGCATGTTAG-TAATTTAAAA---GGGCAATTGCTCCA |
| Enterococcus faecalis | GGTGAGTAACACGTGGTAACCTGCCTAACCTCAGAGGGGATAACACTTGGAAACAGGTGCT | AATACCGCATAACAGTTTAT-GCCGCATGGCATAAGAGTGAAAGGCGCTTTCGGGTGTCG |
| Enterococcus faecium | GGTGAGTAACACGTGGTAACCTACCCATCAGAGGGGATAACACTTGGAAACAGGTGCT | AATACCGTATAACAATCAAAACCGCATGGTTTTGATTTGAAAGGCGCTTTCGGTGTCG |
| Proteus mirabilis | GGTGAGTAATGTATG--GGGATCTGCCCGATAGGGGGGATAACTACTGGAAACGGTAGCT | AATACCGCATAATGTCTACGGACCAAAG------CAGGGGCTCTTCGGACCTTGCA |
| Escherichia coli | GGTGAGTAATGTCTG--GGAAACTGCCTGATGGAGGGGGATAACTACTGGAAACGGTAGCT | AATACCGCATAACGTCGCAAGACCAAAG------AGGGGGACCTTCGGGCCTCTTG |
| Serratia marcescens | GGTGAGTAATGTCTG--GGAAACTGCCTGATGGAGGGGGATAACTACTGGAAACGGTAGCT | AATACCGCATAACGTCCAAGACCAAAG------AGGGGGACCTTCGGGCCTCTTG |
| Enterobacter aerogenes | GGTGAGTAATGTCTG--GGAAACTGCCTGATGGAGGGGGATAACTACTGGAAACGGTAGCT | AATACCGCATAACGTCGCAAGACCAAAG------TGGGGGACCTTCGGGCCTCATG |
| Enterobacter cloacae | GGTGAGTAATGTCTG--GGAAACTGCCTGATGGAGGGGGATAACTACTGGAAACGGTAGCT | AATACCGCATAACGTCGCAAGACCAAAG------AGGGGGACCTTCGGGCCTCTTG |
| Klebsiella pneumoniae | GGTGAGTAATGTCTG--GGAATCTGCCTGATGGAGGGGGATAACTACTGGAAACGGTAGCT | AATACCGCATAACGTCGCAAGACCAAAG------TGGGGGACCTTCGGGCCTCATG |
| Pseudomonas aeruginosa | GGTGAGTAATGCCTA--GGAATCTGCCTGGTAGTGGGGGATAACGTCCGGAAACGGGCGCT | AATACCGCATACGTCCTGAGGGAGAAAG------TGGGGGATCTTCGGACCTCACG |
| Acinetobacter calcoaceticus | GGTGAGTAATGCTTA--GGAATCTGCCTATTAGTGGGGGACAACATTCCGAAGGAATGCT | AATACCGCATACGTCCTACGGGAGAAAG------CAGGGGACCTTCGGGCCTTGCG |
| | * ** *** * * *** *** | ****** *** |

Figure 1B

|  | SNP273 |
| --- | --- |

```
Staphylococcus aureus         CTTATAGATGGATCCGCGGCTGCATTAGCTAGTTGGTAAGGTAACGGCTTACCAAGGCAAC
Staphylococcus epidermidis    CTTATAGATGGATCCGCGGCTGCATTAGCTAGTTGGTAAGGTAACGGCTTACCAAGGCAAC
Streptococcus pneumoniae      CTACCAGATGGACCTGCGTTGTATTAGCTAGTTGGTGGGGTAACGGCTCACCAAGGCGAC
Streptococcus agalactiae      CGTGAGATGGACCTGCGTTGTATTAGCTAGTTGGTGAGGTAAAGGCTCACCAAGGCGAC
Streptococcus pyogenes        CTATGAGATGGACCTGCGTTGTATTAGCTAGTTGGTGAGGTAAAGGCTCACCAAGGCGAC
Enterococcus faecalis         TTGATCGGATGGACGCCGGCTGCATTAGCTAGTTGGTGGTGAGGTAACGGCTCACCAAGGCGAC
Enterococcus faecium          CTGATCGGATGAACCCGCGGCTGCATTAGCTAGTTGGTGAGGTAACGGCTCACCAAGGCGAC
Proteus mirabilis             CTATCGGATGAACCCATATGGATTAGCTAGTAGGTGGGGTAAAGGCTCACCTAGGCGAC
Escherichia coli              CCATCGGATGTGCCCAGATGTGCCCAGATGGATTAGCTAGTAGGTGGGGTAACGGCTCACCTAGGCGAC
Serratia marcescens           CCATCAGATGTGCCCAGATGGATTAGCTAGTAGGTGGGGTAATGGCTCACCTAGGCGAC
Enterobacter aerogenes        CCATCAGATGTGCCCAGATGGATTAGCTAGTAGGTGGGGTAATGGCTCACCTAGGCGAC
Enterobacter cloacae          CCATCAGATGTGCCCAGATGTGCCCAGATGGATTAGCTAGTAGGTGGGGTAACGGCTCACCTAGGCGAC
Klebsiella pneumoniae         CCATCAGATGTGCCCAGATGTGCCCAGATGGATTAGCTAGTAGGTGGGGTAACGGCTCACCTAGGCGAC
Pseudomonas aeruginosa        CTATCAGATGAGCCTAGGTCGGATTAGCTAGTTGGTGGGGTAAAGGCCTACCAAGGCGAC
Acinetobacter calcoaceticus   CTAATAGATGAGCCTAAGTCGGATTAGCTAGTTGGTGGGGTAAAGGCCTACCAAGGCGAC
                                  *     *     *   *    *****  ****** ***  ***  ****  **

Staphylococcus aureus         GATGCATAGCCGACC--TGAGAGGGTGATCGGCCACACTGGAACTGAGACACGGTCCAGAC
Staphylococcus epidermidis    GATGGTAGCCGACC--TGAGAGGGTGATCGGCCACACTGGAACTGAGACACGGTCCAGAC
Streptococcus pneumoniae      GATACATAGCCGACC--TGAGAGGGTGATCGGCCACACTGGGACTGAGACACGGCCCAGAC
Streptococcus agalactiae      GATACATAGCCGACC--TGAGAGGGTGATCGGCCACACTGGGACTGAGACACGGCCCAGAC
Streptococcus pyogenes        GATACATAGCCGACC--TGAGAGGGTGATCGGCCACACTGGGACTGAGACACGGCCCAGAC
Enterococcus faecalis         GATGCATAGCCGACC--TGAGAGGGTGATCGGCCACACTGGGACTGAGACACGGCCCAGAC
Enterococcus faecium          GATGCATAGCCGACC--TGAGAGGGTGATCGGCCACACTGGGACTGAGACACGGCCCAGAC
Proteus mirabilis             GATGCATAGCCGCACCTGACCTGATCGGCCACATTGGGACTGAGACACGGCCCA-AA
Escherichia coli              GATCTCTAGCTGGTC--TGAGGATGATCAGCCACACTGGAACTGGAACTGAGACACGGTCCAGAC
Serratia marcescens           GATCCCTAGCTGGTC--TGAGAGGATGATCAGCCACACTGGAACTGAGACACGGTCCAGAC
Enterobacter aerogenes        GATCCCTAGCTGGTC--TGAGAGGATGATCAGCCACACTGGAACTGAGACACGGTCCAGAC
Enterobacter cloacae          GATCCCTAGCTGGTC--TGAGAGGATGATCAGCCACACTGGAACTGAGACACGGTCCAGAC
Klebsiella pneumoniae         GATCCCTAGCTGGTC--TGAGAGGATGATCAGCCACACTGGAACTGAGACACGGTCCAGAC
Pseudomonas aeruginosa        GATCCGTAACTGGTC--TGAGAGGATGATCAGTCACACTGGAACTGAGACACGGTCCAGAC
Acinetobacter calcoaceticus   GATCGTAG--CGGTC--TGAGGACTGGAGATGATCCGCCACACTGGGACTGAGACACGGCCCAGAC
                                 *  *  ***     ***  *  **    * ** *** ***********  *****
```

Figure 1C

|  | SNP378 |
| --- | --- |
| Staphylococcus aureus | TCCTACGGGAGGCAGCAGTAGGGAATCTTCCCCAATGGGCGAAAGCCTGACGGAGCAACG |
| Staphylococcus epidermidis | TCCTACGGGAGGCAGCAGTAGGGAATCTTCCCCAATGGGCGAAAGCCTGACGGAGCAACG |
| Streptococcus pneumoniae | TCCTACGGGAGGCAGCAGTAGGGAATCTTCGGCAATGGACGGAAGTCTGACCGAGCAACG |
| Streptococcus agalactiae | TCCTACGGGAGGCAGCAGTAGGGAATCTTCGGCAATGGGCGAAAGCCTGACCGAGCAACG |
| Streptococcus pyogenes | TCCTACGGGAGGCAGCAGTAGGGAATCTTCGGCAATGGGCGCAACCCTGACCGAGCAACG |
| Enterococcus faecalis | TCCTACGGGAGGCAGCAGTAGGGAATCTTCGGCAATGGACGAAAGTCTGACCGAGCAACG |
| Enterococcus faecium | CTCTACGGGAGGCAGCAGTAGGGAATCTTCGGCAATGGACGAAAGTCTGACCGAGCAACG |
| Proteus mirabilis | TCCTACGGGAGGCAGCAGTGGGGAATATTGCACAATGGGCGCAAGCCTGATGCAGCCATG |
| Escherichia coli | TCCTACGGGAGGCAGCAGTGGGGAATATTGCACAATGGGCGCAAGCCTGATGCAGCCATG |
| Serratia marcescens | TCCTACGGGAGGCAGCAGTGGGGAATATTGCACAATGGGCGCAAGCCTGATGCAGCCATG |
| Enterobacter aerogenes | TCCTACGGGAGGCAGCAGTGGGGAATATTGCACAATGGGCGCAAGCCTGATGCAGCCATG |
| Enterobacter cloacae | TCCTACGGGAGGCAGCAGTGGGGAATATTGCACAATGGGCGCAAGCCTGATGCAGCCATG |
| Klebsiella pneumoniae | TCCTACGGGAGGCAGCAGTGGGGAATATTGCACAATGGGCGCAAGCCTGATGCAGCCATG |
| Pseudomonas aeruginosa | TCCTACGGGAGGCAGCAGTGGGGAATATTGGACAATGGGCGAAAGCCTGATCCAGCCATG |
| Acinetobacter calcoaceticus | TCCTACGGGAGGCAGCAGTGGGGAATATTGGACAATGGGGGAACCCTGATCCAGCCATG |
|  | ****** ****************** ***** * ****** * ** * *** *** ** |

|  | SNP412 | | SNP440 | |
| --- | --- | --- | --- | --- |
| Staphylococcus aureus | CCGCGTGAGTGATGAAGGTCTTCGGATCGTAAAACTCTGTTATTAGGGAAGAACATATGT |
| Staphylococcus epidermidis | CCGCGTGAGTGATGAAGGTCTTCGGATCGTAAAACTCTGTTATTAGGGAAGAACAAATGT |
| Streptococcus pneumoniae | CCGCGTGAGTGAAGAAGGTTTTCGGATCGTAAAGCTCTGTTGTAAGAGAAGAACGAGTGT |
| Streptococcus agalactiae | CCGCGTGAGTGAAGAAGGTTTTCGGATCGTAAAGCTCTGTTGTTAGAGAAGAACGTTGGT |
| Streptococcus pyogenes | CCGCGTGAGTGAAGAAGGTTTTCGGATCGTAAAGCTCTGTTGTTAGAGAAGAATGATGGT |
| Enterococcus faecalis | CCGCGTGAGTGAAGAAGGTTTTCGGATCGTAAAACTCTGTTGTTAGAGAAGAACAAGGAC |
| Enterococcus faecium | CCGCGTGAGTGAAGAAGGTTTTCGGATCGTAAAGCTCTGTTGTTAGAGAAGAACAAGGAT |
| Proteus mirabilis | CCGCGTGTATGAAGAAGGCCTTAGGGTTGTAAAGTACTTTCAGCGGGGAGGAAGGTGATA |
| Escherichia coli | CCGCGTGTATGAAGAAGGCCTTCGGGTTGTAAAGTACTTTCAGCGGGGAGGAAGGGAGTA |
| Serratia marcescens | CCGCGTGTATGAAGAAGGCCTTCGGGTTGTAAAGTACTTTCAGCGGGGAGGAAGGGAGTA |
| Enterobacter aerogenes | CCGCGTGTATGAAGAAGGCCTTCGGGTTGTAAAGTACTTTCAGCGGGGAGGAAGGGAGTG |
| Enterobacter cloacae | CCGCGTGTATGAAGAAGGCCTTCGGGTTGTAAAGTACTTTCAGCGGGGAGGAAGGGTTA |
| Klebsiella pneumoniae | CCGCGTGTATGAAGAAGGCCTTCGGGTTGTAAAGTACTTTCAGCGGGGAGGAAGGGTTTG |
| Pseudomonas aeruginosa | CCGCGTGTGTGAAGAAGGCCTTCGGGTTGTAAAGCACTTTAAGTTGGGAGGAAGGGCATG |
| Acinetobacter calcoaceticus | CCGCGTGTGTGAAGAAGGCCTTATGGTTGTAAAGCACTTTAAGCGAGGAGGAGGCTACTA |
|  | ******* * ** ***** ** * ****** ** ** * * * * * * |

Figure 1D

| SNP488 |

```
Staphylococcus aureus          GTAAGTAAC-TGTGCACATCTTGACGGTACCTAATCAGAAAGCCACGGCTAACTACGTGC
Staphylococcus epidermidis     GTAAGTAAC-TATGCACGTCTTGACGGTACCTAATCAGAAAGCCACGGCTAACTACGTGC
Streptococcus pneumoniae       GAGAGTGGAAAGTTCACACTGTGACGGTATCTTACCAGAAAGGACGGCTAACTACGTGC
Streptococcus agalactiae       AGGAGTGGAAATCTACCAAGTGACGGTAACTAACCAGAAAGGACGGCTAACTACGTGC
Streptococcus pyogenes         GGGAGTGGAAAATCCACCAAGTGACGGTAACTAACCAGAAAGGACGGCTAACTACGTGC
Enterococcus faecalis          GTTAGTAAC-TGAACGTCCCCTGACGGTAACTAACCAGAAAGCCACGGCTAACTACGTGC
Enterococcus faecium           GAGAGTAAC-TGTTCATCCCTTGACGGTAACTAACCAGAAAGCCACGGCTAACTACGTGC
Proteus mirabilis              AGGTTAATACCCTTGTCAATTGACGTTACC-CGCAGAAGAAGCACCGGCTAACTCCGTGC
Escherichia coli               AAGTTAATACCTTTGCTCATCAATTGACGTTACC-CGCAGAAGAAGCACCGGCTAACTCCGTGC
Serratia marcescens            AGCTTAATACGTTCATCAATTGACGTTACT-CGCAGAAGAAGCACCGGCTAACTCCGTGC
Enterobacter aerogenes         AGGTTAATAACCTTGGCGATTGACGTTACT-CGCAGAAGAAGCACCGGCTAACTCCGTGC
Enterobacter cloacae           TGGTTAATAACCGCAGCAATTGACGTTACC-CGCAGAAGAAGCACCGGCTAACTCCGTGC
Klebsiella pneumoniae          AGGTTAATAACCTCATCGATTGACGTTACCCTGCAGAAGAAGCACCGGCTAACTCCGTGC
Pseudomonas aeruginosa         AAGTTAATAC-CTTGCTGTTTTGACGTTACCAACAGATAAGCACCGGCTAACTTCGTGC
Acinetobacter calcoaceticus    GTATTAATACTACTGGATAGTGACGTTACTCGCAGAATAAGCACCGGCTAACTCTGTGC
                                        *    ***                *       *           *  *     ****      *   **********

Staphylococcus aureus          CAGCAGCCGCGGTAATACGTAGGTGGCAAGCGTTATCCGGAATTATTGGGCGTAAAGCGC
Staphylococcus epidermidis     CAGCAGCCGCGGTAATACGTAGGTGGCAAGCGTTATCCGGAATTATTGGGCGTAAAGCGC
Streptococcus pneumoniae       CAGCAGCCGCGGTAATACGTAGGTCCCGAGCGTTGTCCGGATTTATTGGGCGTAAAGCGA
Streptococcus agalactiae       CAGCAGCCGCGGTAATACGTAGGTCCCGAGCGTTGTCCGGATTTATTGGGCGTAAAGCGA
Streptococcus pyogenes         CAGCAGCCGCGGTAATACGTAGGTCCCGAGCGTTGTCCGGATTTATTGGGCGTAAAGCGA
Enterococcus faecalis          CAGCAGCCGCGGTAATACGTAGGTGGCAAGCGTTGTCCGGATTTATTGGGCGTAAAGCGA
Enterococcus faecium           CAGCAGCCGCGGTAATACGTAGGTGGCAAGCGTTGTCCGGATTTATTGGGCGTAAAGCGA
Proteus mirabilis              CAGCAGCCGCGGTAATACGGAGGGTGCAAGCGTTAATCGGAATTACTGGGCGTAAAGCGC
Escherichia coli               CAGCAGCCGCGGTAATACGGAGGGTGCAAGCGTTAATCGGAATTACTGGGCGTAAAGCGC
Serratia marcescens            CAGCAGCCGCGGTAATACGGAGGGTGCAAGCGTTAATCGGAATTACTGGGCGTAAAGCGC
Enterobacter aerogenes         CAGCAGCCGCGGTAATACGGAGGGTGCAAGCGTTAATCGGAATTACTGGGCGTAAAGCGC
Enterobacter cloacae           CAGCAGCCGCGGTAATACGGAGGGTGCAAGCGTTAATCGGAATTACTGGGCGTAAAGCGC
Klebsiella pneumoniae          CAGCAGCCGCGGTAATACGGAGGGTGCAAGCGTTAATCGGAATTACTGGGCGTAAAGCGC
Pseudomonas aeruginosa         CAGCAGCCGCGGTAATACGAAGGGTGCAAGCGTTAATCGGAATTACTGGGCGTAAAGCGC
Acinetobacter calcoaceticus    CAGCAGCCGCGGTAATACAGAGGGTGCGAGCGTTAATCGGATTTACTGGGCGTAAAGCGT
                               ******************            *  *    *    * ******     *************
```

Figure 1E

| | |
|---|---|
| Staphylococcus aureus | GCGTAGGCGGTTTTTTAAGTCTGATGTGAAAGCCCACGGCTCAACCCTGGAGGGTCATTG |
| Staphylococcus epidermidis | GCGTAGGCGGTTTTTTAAGTCTGATGTGAAAGCCCACGGCTCAACCGTGGAGGGTCATTG |
| Streptococcus pneumoniae | GCGCAGGCGGTTAGATAAGTCTGAAGTTAAAGGCTGTGGCTTAACCATAGT-AGGCTTTG |
| Streptococcus agalactiae | GCGCAGGCGGTTCTTAAGTCTGAAGTTAAAGGCAGTGGCTTAACCATTGT-ACGCTTTG |
| Streptococcus pyogenes | GCGCAGGCGGTTTTTTAAGTCTGAAGTTAAAGGCATTGGCTCAACCAATGT-ACGCTTTG |
| Enterococcus faecalis | GCGCAGGCGGTTTCTTAAGTCTGATGTGAAAGCCCCGGGCTCAACCGGGGAGGGTCATTG |
| Enterococcus faecium | GCGCAGGCGG--TTCTTAAGTCTGATGTGAAAGCCCCGGGCTCAACCGGGGAGGGTCATTG |
| Proteus mirabilis | ACGCAGGCGGTCAATTAAGTCAGATGTGAAATCAGATGGAATTGCATCT |
| Escherichia coli | ACGCAGGCGGTTTGTTAAGTCAGATGTGAAATCCCCGGGCTCAACCTGGGAACTGCATTT |
| Serratia marcescens | ACGCAGGCGGTTTGTTAAGTCAGATGTGAAATCCCCGGGCTCAACCTGGGAACTGCATTT |
| Enterobacter aerogenes | ACGCAGGCGGTCTGTCAAGTCGGATGTGAAATCCCCGGGCTCAACCTGGGAACTGCATTC |
| Enterobacter cloacae | ACGCAGGCGGTCTGTCAAGTCGGATGTGAAATCCCCGGGCTCAACCTGGGAACTGCATTC |
| Klebsiella pneumoniae | ACGCAGGCGGTCTGTCAAGTCGGATGTGAAATCCCCGGGCTCAACCTGGGAACTGCATTC |
| Pseudomonas aeruginosa | GCGTAGGTGGTTCAGCAAGTTGGATGTGAAATCCCCGGGCTCAACCTGGGAACTGCATCC |
| Acinetobacter calcoaceticus | GCGTAGGCGGCCAATTAAGTCAAATGTGAAATCCCCGAGCTTAACTTGGGAATTGCATTG |
|  | ** *** ** ** *** * *** *** * |

| | SNP647 | SNP653 | |
|---|---|---|---|
| Staphylococcus aureus | GAAACTGGA | AAACTT | GAGTGCAGAAGAGGAAAGTGGAATTCCATGTGTAGCGGTGAAATG |
| Staphylococcus epidermidis | GAAACTGGA | AAACTT | GAGTGCAGAAGAGGAAAGTGGAATTCCATGTGTAGCGGTGAAATG |
| Streptococcus pneumoniae | GAAACTGTT | AACTT | GAGTGCAGAAGAGGAGAGTGGAATTCCATGTGTAGCGGTGAAATG |
| Streptococcus agalactiae | GAAACTGGA | AGACTT | GAGTGCAGAAGAGGAGAGTGGAATTCCATGTGTAGCGGTGAAATG |
| Streptococcus pyogenes | GAAACTGGA | AGACTT | GAGTGCAGAAGAGGAGAGTGGAATTCCATGTGTAGCGGTGAAATG |
| Enterococcus faecalis | GAAACTGGA | GAGACTT | GAGTGCAGAAGAGGAGAGTGGAATTCCATGTGTAGCGGTGAAATG |
| Enterococcus faecium | GAAACTGGA | GAGACTT | GAGTGCAGAAGAGGAGAGTGGAATTCCATGTGTAGCGGTGAAATG |
| Proteus mirabilis | GAAACTGGC | TGGCTA | GAGTCTTGTAGAGGGGGGTAGAATTCCAGGTGTAGCGGTGAAATG |
| Escherichia coli | GATACTGGC | AAGCTA | GAGTCTCGTAGAGGGGGGTAGAATTCCAGGTGTAGCGGTGAAATG |
| Serratia marcescens | GAAACTGGC | AAGCTA | GAGTCTCGTAGAGGGGGGTAGAATTCCAGGTGTAGCGGTGAAATG |
| Enterobacter aerogenes | GAAACTGGC | AGGCTA | GAGTCTTGTAGAGGGGGGTAGAATTCCAGGTGTAGCGGTGAAATG |
| Enterobacter cloacae | GAAACTGCC | AGGCTA | GAGTCTTGTAGAGGGGGGTAGAATTCCAGGTGTAGCGGTGAAATG |
| Klebsiella pneumoniae | GAAACTGCC | AGGCTA | GAGTCTTGTAGAGGGGGGTAGAATTCCAGGTGTAGCGGTGAAATG |
| Pseudomonas aeruginosa | AAAACTACT | GAGCTA | GAGTACGGTAGAGGGTGGTGGAATTTCCTGTGTAGCGGTGAAATG |
| Acinetobacter calcoaceticus | CATACTGGA | ATGCTA | GAGTATGGGAGAGGATGGTAGAATTCCAGGTGTAGCGGTGAAATG |
|  | * *** | ** ** | * ** * ** ***** * ********* |

Figure 1F

| | |
|---|---|
| Staphylococcus aureus | CGCAGAGATATGGAGGAACACCAGTGGCGAAGGCGACTTTCTGGTCTGTAACTGACGCTG |
| Staphylococcus epidermidis | CGCAGAGATATGGAGGAACACCAGTGGCGAAGGCGACTTTCTGGTCTGTAACTGACGCTG |
| Streptococcus pneumoniae | CGTAGATATATGGAGGAACACCGGTGGCGAAAGCGGCTCTCTGGCTTGTAACTGACGCTG |
| Streptococcus agalactiae | CGTAGATATATGGAGGAACACCGGTGGCGAAAGCGGCTCTCTGGTCTGTAACTGACGCTG |
| Streptococcus pyogenes | CGTAGATATATGGAGGAACACCGGTGGCGAAAGCGGCTCTCTGGTCTGTAACTGACGCTG |
| Enterococcus faecalis | CGTAGATATGGAGGAACACCAGTGGCGAAGGCGGCTCTCTGGTCTGTAACTGACGCTG |
| Enterococcus faecium | CGTAGATATGGAGGAACACCAGTGGCGAAGGCGGCTCTCTGGTCTGTAACTGACGCTG |
| Proteus mirabilis | CGTAGAGATGTGGAGGAATACCGGTGGCGAAGGCGGCCCCCTGGACGAAGACTGACGCTC |
| ESCHERICHIA COLI | CGTAGAGATCTGGAGGAATACCGGTGGCGAAGGCGGCCCCCTGGACGAAGACTGACGCTC |
| Serratia marcescens | CGTAGAGATCTGGAGGAATACCGGTGGCGAAGGCGGCCCCCTGGACGAAGACTGACGCTC |
| Enterobacter aerogenes | CGTAGAGATCTGGAGGAATACCGGTGGCGAAGGCGGCCCCCTGGACAAAGACTGACGCTC |
| Enterobacter cloacae | CGTAGAGATCTGGAGGAATACCGGTGGCGAAGGCGGCCCCCTGGACAAAGACTGACGCTC |
| Klebsiella pneumoniae | CGTAGAGATCTGGAGGAATACCGGTGGCGAAGGCGGCCCCCTGGACAAAGACTGACGCTC |
| Pseudomonas aeruginosa | CGTAGAGATATGGAGGAATACCGGTGGCGAAGGCGGACCACCTGGACTGATACTGACACTG |
| Acinetobacter calcoaceticus | CGTAGAGATCTGGAGGAATACCGATGGCGAAGGCAGCCATCTGGCCTATACTGACGCTG |
| | ** * *** ** * ***** *** ******** ** ****** ****** ** |

| | |
|---|---|
| Staphylococcus aureus | ATGTGCGAAAGCGTGGGGATCAAACAGGATTAGATACCCTGGTAGTCCACGCCGTAAACG |
| Staphylococcus epidermidis | ATGTGCGAAAGCGTGGGGATCAAACAGGATTAGATACCCTGGTAGTCCACGCCGTAAACG |
| Streptococcus pneumoniae | AGGCTCGAAAGCGTGGGGAGCAAACAGGATTAGATACCCTGGTAGTCCACGCCGTGTAAACG |
| Streptococcus agalactiae | AGGCTCGAAAGCGTGGGGAGCAAACAGGATTAGATACCCTGGTAGTCCACGCCGTAAACG |
| Streptococcus pyogenes | AGGCTCGAAAGCGTGGGGAGCAAACAGGATTAGATACCCTGGTAGTCCACGCCGTAAACG |
| Enterococcus faecalis | AGGCTCGAAAGCGTGGGGAGCAAACAGGATTAGATACCCTGGTAGTCCACGCCGTAAACG |
| Enterococcus faecium | AGGCTCGAAAGCGTGGGGAGCAAACAGGATTAGATACCCTGGTAGTCCACGCCGTAAACG |
| Proteus mirabilis | AGGTGCGAAAGCGTGGGGAGCAAACAGGATTAGATACCCTGGTAGTCCACGCTGTAAACG |
| Escherichia coli | AGGTGCCAAAGCGTGGGGAGCAAACAGGATTAGATACCCTGGTAGTCCACGCCGTAAACG |
| Serratia marcescens | AGGTGCGAAAGCGTGGGGAGCAAACAGGATTAGATACCCTGGTAGTCCACGCTGTAAACG |
| Enterobacter aerogenes | AGGTGCCAAAGCGTGGGGAGCAAACAGGATTAGATACCCTGGTAGTCCACGCCGTAAACG |
| Enterobacter cloacae | AGGCTCGAAAGCGTGGGGAGCAAACAGGATTAGATACCTGGTAGTCCACGCCGTAAACG |
| Klebsiella pneumoniae | AGGCTCGAAAGCGTGGGGAGCAAACAGGATTAGATACCCTGGTAGTCCACGCCGTAAACG |
| Pseudomonas aeruginosa | AGGTGCGAAAGCGTGGGGAGCAAACAGGATTAGATACCCTGGTAGTCCACGCCGTAAACG |
| Acinetobacter calcoaceticus | AGGTACGAAAGCATGGGAGCAGAACAGGATTAGATACCCTGGTAGTCCATGCCGTAAACG |
| | * * ****** ***** ************************** ** ******* |

Figure 1G

| Species | Sequence |
|---|---|
| Staphylococcus aureus | ATGAGTGCTAAGTGTTAGGGGGTTTCCGCCCCTTAGTGCTGCAGCTAACGCATTAAGCAC |
| Staphylococcus epidermidis | ATGAGTGCTAAGTGTTAGGGGGTTTCCGCCCCTTAGTGCTGCAGCTAACGCATTAAGCAC |
| Streptococcus pneumoniae | ATGAGTGCTAGGTGTTAGACCCTTTCCGGGGTTTAGTGCCGTAGTGCCAGCTAACGCATTAAGCAC |
| Streptococcus agalactiae | ATGAGTGCTAGGTGTGTAGGTGTTAGGCCTTTCCGGGGCTTAGTGCCGGAGCTAACGCATTAAGCAC |
| Streptococcus pyogenes | ATGAGTGCTAGGTGTTAGGCCTGTTAGGCCCTTTCCGGGGCTTAGTGCCGGAGCTAACGCATTAAGCAC |
| Enterococcus faecalis | ATGAGTGCTAAGTGTTGGAGGTTTCCGCCCTTCAGTGCTGCAGCAAACGCATTAAGCAC |
| Enterococcus faecium | ATGAGTGCTAAGTGTTGGAGGTTTCCGCCCTTCAGTGCTGCAGCTAACGCATTAAGCAC |
| Proteus mirabilis | ATGTCGATTTAGAGGTTGTGGTCTTG--AACCGTGGCTTCTGGAGCTAACGCGTTAAATCG |
| Escherichia coli | ATGTCGACTTGGAGGTTGTGCCCTTG--AGGCGTGGCTTCCGGAGCTAACGCGTTAAGTCG |
| Serratia marcescens | ATGTCGATTTGGAGGTTGTGCCCTTG--AGGCGTGGCTTCCGGAGCTAACGCGTTAATCG |
| Enterobacter aerogenes | ATGTCGACTTGGAGGTTGTGCCCTTG--AGGCGTGGCTTCCGGAGCTAACGCGTTAAGTCG |
| Enterobacter cloacae | ATGTCGATTTGGAGGTTGTGCCCTTG--AGGCGTGGCTTCCGGAGCTAACGCGTTAAGTCG |
| Klebsiella pneumoniae | ATGTCGATTTGGAGGTTGTGCCCTTG--AGGCGTGGCTTCCGGAGCTAACGCGTTAAATCG |
| Pseudomonas aeruginosa | ATGTCGACTAGCCGTTGGGATCCTG--AGATCTTAGTGGCGCAGCTAACGCGATAAGTCG |
| Acinetobacter calcoaceticus | ATGTTACTAGCCGTTGGGCCTTTG--AGGCTTTAGTGCCGCAGCTAACGCGATAAGTAG |
| | *** * *** ***** *** |

| | |
|---|---|
| Staphylococcus aureus | TCCGCCTGGGGAGTACGACCGCAAGGTTGAAACTCAAAGGAATTGACGGGACCCGCACA |
| Staphylococcus epidermidis | TCCGCCTGGGGAGTACGACCGCAAGGTTGAAACTCAAAGGAATTGACGGGACCCGCACA |
| Streptococcus pneumoniae | TCCGCCTGGGGAGTACGACCGCAAGGTTGAAACTCAAAGGAATTGACGGGGCCCGCACA |
| Streptococcus agalactiae | TCCGCCTGGGGAGTACGACCGCAAGGTTGAAACTCAAAGGAATTGACGGGGCCCGCACA |
| Streptococcus pyogenes | TCCGCCTGGGGAGTACGACCGCAAGGTTGAAACTCAAAGGAATTGACGGGGCCCGCACA |
| Enterococcus faecalis | TCCGCCTGGGGAGTACGACCGCAAGGTTGAAACTCAAAGGAATTGACGGGGCCCGCACA |
| Enterococcus faecium | TCCGCCTGGGGAGTACGACCGCAAGGTTGAAACTCAAAGGAATTGACGGGGCCCGCACA |
| Proteus mirabilis | ACCGCCTGGGGAGTACGGCCGCAAGGTTAAAACTCAAATGAATTGACGGGGCCCGCACA |
| Escherichia coli | ACCGCCTGGGGAGTACGGCCGCAAGGTTAAAACTCAAATGAATTGACGGGGCCCGCACA |
| Serratia marcescens | ACCGCCTGGGGAGTACGGCCGCAAGGTTAAAACTCAAATGAATTGACGGGGCCCGCACA |
| Enterobacter aerogenes | ACCGCCTGGGGAGTACGGCCGCAAGGTTAAAACTCAAATGAATTGACGGGGCCCGCACA |
| Enterobacter cloacae | ACCGCCTGGGGAGTACGGCCGCAAGGTTAAAACTCAAATGAATTGACGGGGCCCGCACA |
| Klebsiella pneumoniae | ACCGCCTGGGGAGTACGGCCGCAAGGTTAAAACTCAAATGAATTGACGGGGCCCGCACA |
| Pseudomonas aeruginosa | ACCGCCTGGGGAGTACGGCCGCAAGGTTAAAACTCAAATGAATTGACGGGGCCCGCACA |
| Acinetobacter calcoaceticus | ACCGCCTGGGGAGTACGGTCGCAAGACTAAAACTCAAATGAATTGACGGGGCCCGCACA |
| | *********** * ***** ***** * *************** *********** |

Figure 1H

```
Staphylococcus aureus              AGCGGGTGGAGCATGTGGTTTAATTCGAAGCAACGCGAAGAACCTTACCAAATCTTGACAT
Staphylococcus epidermidis         AGCGGGTGGAGCATGTGGTTTAATTCGAAGCAACGCGAAGAACCTTACCAAATCTTGACAT
Streptococcus pneumoniae           AGCGGGTGGAGCATGTGGTTTAATTCGAAGCAACGCGAAGAACCTTACCAGGTCTTGACAT
Streptococcus agalactiae           AGCGGGTGGAGCATGTGGTTTAATTCGAAGCAACGCGAAGAACCTTACCAGGTCTTGACAT
Streptococcus pyogenes             AGCGGGTGGAGCATGTGGTTTAATTCGAAGCAACGCGAAGAACCTTACCAGGTCTTGACAT
Enterococcus faecalis              AGCGGGTGGAGCATGTGGTTTAATTCGAAGCAACGCGAAGAACCTTACCAGGTCTTGACAT
Enterococcus faecium               AGCGGGTGGAGCATGTGGTTTAATTCGAAGCAACGCGAAGAACCTTACCAGGTCTTGACAT
Proteus mirabilis                  AGCGGGTGGAGCATGTGGTTTAATTCGATGCAACGCGAAGAACCTTACCTGGTCTTGACAT
Escherichia coli                   AGCGGGTGGAGCATGTGGTTTAATTCGATGCAACGCGAAGAACCTTACCTGGTCTTGACAT
Serratia marcescens                AGCGGGTGGAGCATGTGGTTTAATTCGATGCAACGCGAAGAACCTTACCTACTCTTGACAT
Enterobacter aerogenes             AGCGGGTGGAGCATGTGGTTTAATTCGATGCAACGCGAAGAACCTTACCTACTCTTGACAT
Enterobacter cloacae               AGCGGGTGGAGCATGTGGTTTAATTCGATGCAACGCGAAGAACCTTACCTGGTCTTGACAT
Klebsiella pneumoniae              AGCGGGTGGAGCATGTGGTTTAATTCGATGCAACGCGAAGAACCTTACCTGGTCTTGACAT
Pseudomonas aeruginosa             AGCGGGTGGAGCATGTGGTTTAATTCGAAGCAACGCGAAGAACCTTACCTGGCCTTGACAT
Acinetobacter calcoaceticus        AGCGGGTGGAGCATGTGGTTTAATTCGATGCAACGCGAAGAACCTTACCTGGCCTTGACAT
                                   ****************************  *************** *** *********

Staphylococcus aureus              CCTTTGACAACTCTAGAGATAGAGCTTTCCCCCTTCGGGGGACAAAGTGACAGGTGGTGCA
Staphylococcus epidermidis         CCTCTGACCCCTCTAGAGATAGAGCTTTCCCCCTTCGGGGGACAAAGTGACAGGTGGTGCA
Streptococcus pneumoniae           CCCTCTGACCGCTCTAGAGATAGAGTTTT--CCTTCGGGGAACTCTGAGACAGGTGGTGCA
Streptococcus agalactiae           CCTTCTGACCGGCCGCTCTAGAGATAGAGCTTTC---TCTTCGGAGCAGAAGTGACAGGTGGTGCA
Streptococcus pyogenes             CCCGATGCCCGCTCTAGAGATAGAGCTTTT--ACTTCGGTACATCGGTGACAAAGTGACAGGTGGTGCA
Enterococcus faecalis              CCTTTGACCACTCTAGAGATAGAGCTTTC---CCTTCGGGGACAAAGTGACAGGTGGTGCA
Enterococcus faecium               CCTTTGACCACTCTAGAGATAGAGCTTCC---CCTTCGGGGGCAAAGTGACAGGTGGTGCA
Proteus mirabilis                  CCAGCGAATCCTTTAGAGATAGAGGAGTG---CCTTCGGGAACGCTGTGAGACAGGTGCTGCA
Escherichia coli                   CCACAGAACTTTCCAGAGATGGATTGGTG---CCTTCGGGAACTCTGAGACAGGTGCTGCA
Serratia marcescens                CCAGAGAACTTTCCAGAGATGGATTGGTG---CCTTCGGGAACTCTGAGACAGGTGCTGCA
Enterobacter aerogenes             CCAGAGAACTTAGCAGATGGATGCTTTGGTG---CCTTCGGGAACTCTGAGACAGGTGCTGCA
Enterobacter cloacae               CCAGAGAACTTTCCAGAGATGGATGGATTGGTG---CCTTCGGGAACTGTGAGACAGGTGCTGCA
Klebsiella pneumoniae              CCACAGAACTTTCCAGAGATGGATGGATTGGTG---CCTTCGGGGAACTGTGAGACAGGTGCTGCA
Pseudomonas aeruginosa             GCTCAGAACTTTCCAGAGATGGATTGGTG---CCTTCGGGAACTCAGACACAGGTGCTGCA
Acinetobacter calcoaceticus        ACTAGAAACTTTCCAGAGATTAGATACAGGATTGGTG---CCTTCGGGAATTAGATACAGGTGCTGCA
                                      *         *         *        *  ******* ****  *****
```

Figure 1I

| | |
|---|---|
| Staphylococcus aureus | TGGTTGTCGTCAGCTCGTCGTCGTGAGATGTTGGGTTAAGTCCCGCAACGAGCGCAACCCT |
| Staphylococcus epidermidis | TGGTTGTCGTCAGCTCGTCGTCGTGAGATGTTGGGTTAAGTCCCGCAACGAGCGCAACCCT |
| Streptococcus pneumoniae | TGGTTGTCGTCAGCTCGTCGTCGTGAGATGTTGGGTTAAGTCCCGCAACGAGCGCAACCCC |
| Streptococcus agalactiae | TGGTTGTCGTCAGCTCGTCGTCGTGAGATGTTGGGTTAAGTCCCGCAACGAGCGCAACCCC |
| Streptococcus pyogenes | TGGTTGTCGTCAGCTCGTCGTCGTGAGATGTTGGGTTAAGTCCCGCAACGAGCGCAACCCC |
| Enterococcus faecalis | TGGTTCTCGTCAGCTCGTCGTCGTGAGATGTTGGGTTAAGTCCCGCAACGAGCGCAACCCT |
| Enterococcus faecium | TGGTTCTCGTCAGCTCGTCGTCGTGAGATGTTGGGTTAAGTCCCGCAACGAGCGCAACCCT |
| Proteus mirabilis | TGGCTGTCGTCAGCTCGTGTTGTGAAATGTTGGGTTAAGTCCCGCAACGAGCGCAACCCT |
| Escherichia coli | TGGCTGTCGTCAGCTCGTGTTGTGAAATGTTGGGTTAAGTCCCGCAACGAGCGCAACCCT |
| Serratia marcescens | TGGCTGTCGTCAGCTCGTGTTGTGAAATGTTGGGTTAAGTCCCGCAACGAGCGCAACCCT |
| Enterobacter aerogenes | TGGCTGTCGTCAGCTCGTGTTGTGAAATGTTGGGTTAAGTCCCGCAACGGGCAACCCT |
| Enterobacter cloacae | TGGCTGTCGTCAGCTCGTGTTGTGAAATGTTGGGTTAAGTCCCGCAACGAGCGCAACCCT |
| Klebsiella pneumoniae | TGGCTGTCGTCAGCTCGTGTTGTGAAATGTTGGGTTAAGTCCCGCAACGAGCGCAACCCT |
| Pseudomonas aeruginosa | TGGCTGTCGTCAGCTCGTGTCGTGAGATGTTGGGTTAAGTCCCGTAACGAGCGCAACCCT |
| Acinetobacter calcoaceticus | TGGCTGTCGTCAGCTCGTGTCGTGAGATGTTGGGTTAAGTCCCGCAACGAGCGCAACCCT |
| | *** ********************* ***** * **** ******************* |

| | |
|---|---|
| Staphylococcus aureus | TAAGCTTAGTTGCCATCATT--AAGTTGGGCACTCTAAGTTGACTGCCGGTGACAAACCG |
| Staphylococcus epidermidis | TAAGCTTAGTTGCCATCATT--AAGTTGGGCACTCTAAGTTGACTGCCGGTGACAAACCG |
| Streptococcus pneumoniae | TATTGTTAGTTGCCATCATT--CAGTTGGGCACTCTAGCGAGACTGCCGGTAATAAACCG |
| Streptococcus agalactiae | TATTGTTAGTTGCCATCATT--AAGTTGGGCACTCTAGCGAGACTGCCGGTAATAAACCG |
| Streptococcus pyogenes | TATTGTTAGTTGCCATCATT--AAGTTGGGCACTCTAGCGAGACTGCCGGTAATAAACCG |
| Enterococcus faecalis | TATTGTTAGTTGCCATCATT--TAGTTGGGCACTCTAGCGAGACTGCCGGTGACAAACCG |
| Enterococcus faecium | TATTGTTAGTTGCCATCATT--CAGTTGGGCACTCTAGCAAGACTGCCGGTGACAAACCG |
| Proteus mirabilis | TATCCTTTGTTGCCAGCACGTAATGGTGGGAACTCAAAGGAGACTGCCAGTGATAAACTG |
| Escherichia coli | TATCTTTTGTTGCCAGCGGT--CCGGCCGGGAACTCAAAGGAGACTGCCAGTGATAAACTG |
| Serratia marcescens | TATCCTTTGTTGCCAGCGGT--TCGGCCGGGAACTCAAAGGAGACTGCCAGTGATAAACTG |
| Enterobacter aerogenes | TATCCTTTGTTGCCAGCGGT--CCGGCCGGGAACTCAAAGGAGACTGCCAGTGATAAACTG |
| Enterobacter cloacae | TATCCTTTGTTGCCAGCGGT--CCGGCCGGGAACTCAAAGGAGACTGCCAGTGATAAACTG |
| Klebsiella pneumoniae | TATCCTTTGTTGCCAGCGGT--CCGGCCGGGAACTCAAAGGAGACTGCCAGTGATAAACTG |
| Pseudomonas aeruginosa | TGTCCTTAGTTACCAGCACC--TCGGGTGGGCACTCTAAGGAGACTGCCAGTGACAAACCG |
| Acinetobacter calcoaceticus | TTTCCTTACTTGCCAGCATT--TCGGATGGGAACTTTAAGGATACTGCCAGTGACAAACTG |
| | *   * ***  *  *** *  *   *    **  **  *   ****** * ** |

Figure 1J

| Species | Sequence 1 | Sequence 2 |
|---|---|---|
| Staphylococcus aureus | GAGGAAGGTGGGGATGACGTCAAATCATCATGCCCCTTATGATTTGGGCTACACACGTGC | TACAATGGACAATACAAAGGGCAGCGAAACCGTGAGGTGAGGTCAAGTCAAGCAAATCCATAAAGTTGT |
| Staphylococcus epidermidis | GAGGAAGGTGGGGATGACGTCAAATCATCATGCCCCTTATGATTTGGGCTACACACGTGC | TACAATGGACAATACAAAGGGCAGCGAAACCGTGAGGTGAGGTCAAGTCAAGCAAATCCATAAAGTTGT |
| Streptococcus pneumoniae | GAGGAAGGTGGGGATGACGTCAAATCATCATGCCCCTTATGACCTGGGCTACACACGTGC | TACAATGGCTGGTACAACGAGTCGCAAGCCGGTGACGGCAAGCCAAGCTAATCTCTTAAAGCCAG |
| Streptococcus agalactiae | GAGGAAGGTGGGGATGACGTCAAATCATCATGCCCCTTATGACCTGGGCTACACACGTGC | TACAATGGTTGGTACAACGAGTCGCAAGCCGGTGACGGCAAGCCAAGCTAATCTCTTAAAGCCAA |
| Streptococcus pyogenes | GAGGAAGGTGGGGATGACGTCAAATCATCATGCCCCTTATGACCTGGGCTACACACGTGC | TACAATGGTTGGTACAACGAGTCGCAAGCCGGTGACGGCAAGCCAAGCTAATCTCTTAAAGCCAA |
| Enterococcus faecalis | GAGGAAGGTGGGGATGACGTCAAATCATCATGCCCCTTATGACCTGGGCTACACACGTGC | TACAATGGGAAGTACAACGAGTCGCTAGACCGGAGCCGAGGTCATGCAAATCTCTTAAAGCTTC |
| Enterococcus faecium | GAGGAAGGTGGGGATGACGTCAAATCATCATGCCCCTTATGACCTGGGCTACACACGTGC | TACAATGGGAAGTACAACGAGTCGCTAGACCGGAGCCGAGGTCATGCAAATCTCTTAAAGCTTC |
| Proteus mirabilis | GAGGAAGGTGGGGATGACGTCAAGTCATCATGCCCTTACGACCAGGGGTAGGGCTACACACGTGC | TACAATGGCAGATACAAAGAGAAGCGACCTCGCGAGAGCAAGCGACCTCATAAAGTCTG |
| Escherichia coli | GAGGAAGGTGGGGATGACGTCAAGTCATCATGCCCTTACGACCAGGGCTACACACGTGC | TACAATGGCGCATACAGAGGGCAGCGAACTCGCGAGAGCAAGCGGACCTCATAAAGTGCG |
| Serratia marcescens | GAGGAAGGTGGGGATGACGTCAAGTCATCATGCCCTTACGACCAGGGCTACACACGTGC | TACAATGGCATATACAACAGAAGCGACCTCGCGAGAGCAAGCGGACCTCATAAAGTATG |
| Enterobacter aerogenes | GAGGAAGGTGGGGATGACGTCAAGTCATCATGCCCTTACGACCAGGGCTACACACGTGC | TACAATGGCATATACAACAGAAGCGACCTCGCGAGAGCAAGCGGACCTCATAAAGTATG |
| Enterobacter cloacae | GAGGAAGGTGGGGATGACGTCAAGTCATCATGCCCTTACGACCAGGGCTACACACGTGC | TACAATGGCATATACAACAGAAGCGACCTCGCGAGAGCAAGCGGACCTCATAAAGTATG |
| Klebsiella pneumoniae | GAGGAAGGTGGGGATGACGTCAAGTCATCATGCCCTTACGACCAGGGCTACACACGTGC | TACAATGGCATATACAACAGAAGCGACCTCGCGAGAGCAAGCGGACCTCATAAAGTGCG |
| Pseudomonas aeruginosa | GAGGAAGGTGGGGATGACGTCAAGTCATCATGCCCTTACGACCAGGGCTACACACGTGC | TACAATGGTCGGTACAAAGGGTTGCCAAGCCGCGAGGTGAGCTAAGCTAATCCATAAACCGA |
| Acinetobacter calcoaceticus | GAGGAAGGGCGGGGACGACGTCAAGTCATCATGCCCTTACGGCCAGGGCTACACACGTGC | TACAATGGTCGGTACAAAGGGTTGCTACTAGCGATAGGATGCTAATCTCAAAAGCCGA |
| | ******* *** ************************ *** ** * ** * ************ | ****** *** ** * *** ** * *** |

Figure 1K

| Species | Sequence |
|---|---|
| Staphylococcus aureus | TCTCAGTTCGGATTGTAGTCTGCAACTCGACTACATGAAGCTGGAATCGCTAGTAATCGT |
| Staphylococcus epidermidis | TCTCAGTTCGGATTGTAGTCTGCAACTCGACTATATGAAGCTGGAATCGCTAGTAATCGT |
| Streptococcus pneumoniae | TCTCAGTTCGGATTGTAGGCTGCAACTCGCCTACATGAAGTCGGAATCGCTAGTAATCGC |
| Streptococcus agalactiae | TCTCAGTTCGGATTGTAGGCTGCAACTCGCCTACATGAAGTCGGAATCGCTAGTAATCGC |
| Streptococcus pyogenes | TCTCAGTTCGGATTGTAGGCTGCAACTCGCCTACATGAAGTCGGAATCGCTAGTAATCGC |
| Enterococcus faecalis | TCTCAGTTCGGATTGCAGGCTGCAACTCGCCTGCATGAAGCCGGAATCGCTAGTAATCGC |
| Enterococcus faecium | TCTCAGTTCGGATTGCAGGCTGCAACTCGCCTGCATGAAGCCGGAATCGCTAGTAATCGC |
| Proteus mirabilis | TCGTAGTCCGGATTGGAGTCTGCAACTCGACTCCATGAAGTCGGAATCGCTAGTAATCGT |
| Escherichia coli | TCGTAGTCCGGATTGGAGTCTGCAACTCGACTCCATGAAGTCGGAATCGCTAGTAATCGT |
| Serratia marcescens | TCGTAGTCCGGATTGGAGTCTGCAACTCGACTGCATGAAGTCGGAATCGCTAGTAATCGT |
| Enterobacter aerogenes | TCGTAGTCCGGATTGGAGTCTGCAACTCGACTGCATGAAGTCGGAATCGCTAGTAATCGT |
| Enterobacter cloacae | TCGTAGTCCGGATTGGAGTCTGCAACTCGACTGCATGAAGTCGGAATCGCTAGTAATCGT |
| Klebsiella pneumoniae | TCGTAGTCCGGATTGGAGTCTGCAACTCGACTCCATGAAGTCGGAATCGCTAGTAATCGT |
| Pseudomonas aeruginosa | TCGTAGTCCGATCGCAGTCTGCAACTCGACTGCGTGAAGTCGGAATCGCTAGTAATCGT |
| Acinetobacter calcoaceticus | TCGTAGTCCGGATTGGAGTCTGCAACTCGACTCCATGAAGTCGGAATCGCTAGTAATCGT |
|  | ** *** * ** ****************** * ** ****** ************* |

| Species | Sequence |
|---|---|
| Staphylococcus aureus | AGATCAGCATGCTACGGTGAATACGTTCCCGGGTCTTGTACACACCGCCCGTCACACCAC |
| Staphylococcus epidermidis | AGATCAGCATGCTACGGTGAATACGTTCCCGGGTCTTGTACACACCGCCCGTCACACCAC |
| Streptococcus pneumoniae | GGATCAGCACGCCACGGTGAATACGTTCCCGGGCCTTGTACACACCGCCCGTCACACCAC |
| Streptococcus agalactiae | GGATCAGCACGCCACGGTGAATACGTTCCCGGGCCTTGTACACACCGCCCGTCACACCAC |
| Streptococcus pyogenes | GGATCAGCACGCCACGGTGAATACGTTCCCGGGCCTTGTACACACCGCCCGTCACACCAC |
| Enterococcus faecalis | GGATCAGCACGCCGCGGTGAATACGTTCCCGGGCCTTGTACACACCGCCCGTCACACCAC |
| Enterococcus faecium | GGATCAGCACGCCGC-GTGAATACGTTCCCGGGCCTTGTACACACCGCCCGTCACACCAC |
| Proteus mirabilis | AGATCAGAATGCTACGGTGAATACGTTCCCGGGCCTTGTACACACCGCCCGTCACACCAT |
| Escherichia coli | GGATCAGAATGCCACGGTGAATACGTTCCCGGGCCTTGTACACACCGCCCGTCACACCAT |
| Serratia marcescens | AGATCAGAATGCTACGGTGAATACGTTCCCGGGCCTTGTACACACCGCCCGTCACACCAT |
| Enterobacter aerogenes | AGATCAGAATGCTACGGTGAATACGTTCCCGGGCCTTGTACACACCGCCCGTCACACCAT |
| Enterobacter cloacae | AGATCAGAATGCTACGGTGAATACGTTCCCGGGCCTTGTACACACCGCCCGTCACACCAT |
| Klebsiella pneumoniae | AGATCAGAATGCTACGGTGAATACGTTCCCGGGCCTTGTACACACCGCCCGTCACACCAT |
| Pseudomonas aeruginosa | GAATCAGAATGTCACGGTGAATACGTTCCCGGGCCTTGTACACACCGCCCGTCACACCAT |
| Acinetobacter calcoaceticus | GGATCAGAATGCCC---GGTGATACGTTCCCGGGCCTTGTACACACCGCCCGTCACACCAT |
|  | ****** * *      * ************ ***************************  |

Figure 1L

```
Staphylococcus aureus              GAGAGTTTGTAACACCCGAAGCCGGTGGAGTAACCTTTAGGAGCTAGCCGTCGAAGGTG
Staphylococcus epidermidis         GAGAGTTTGTAACACCCGAAGCCGGTGGAGTAACCATT-TGGAGCTAGCCGTCGAAGGTG
Streptococcus pneumoniae           GAGAGTTTGTAACACCCGAAGCCGAAGTCGGTGAGGTAACCG-TAAGGAGCCAGCCGCCTAAGGTG
Streptococcus agalactiae           GAGAGTTTGTAACACCCGAAGCCGAAGTCGGTGAGGTAACCTTTTAGGAGCCAGCCGCCTAAGGTG
Streptococcus pyogenes             GAGAGTTTGTAACACCCGAAGCCGAAGTCGGTGAGGTAACCTATTAGGAGCCAGCCGCCTAAGGTG
Enterococcus faecalis              GAGAGTTTGTAACACCCGAAGCCGAAGTCGGTGAGGTAACCTTTTGGAGCCAGCCGCCTAAGGTG
Enterococcus faecium               GAGAGTTTGTAACACCCGAAGCCGAAGTCGGTGAGGTAACCTTT-TGGAGCCAGCCGCCTAAGGTG
Proteus mirabilis                  GGGAGTGGGTTGCAAAAGAAGTAGGTAGCTTAACCTTC-GGGAGGGCGCTTACCACTTTG
Escherichia coli                   GGGAGTGGGTTGCAAAAGAAGTAGGTAGCTTAACCTTC-GGGAGGGCGCTTACCACTTTG
Serratia marcescens                GGGAGTGGGTTGCAAAAGAAGTAGGTAGCTTAACCTTC-GGGAGGGCGCTTACCACTTTG
Enterobacter aerogenes             GGGAGTGGGTTGCAAAAGAAGTAGGTAGCTTAACCTTC-GGGAGGNCGCTTTACCACTT-
Enterobacter cloacae               GGGAGTGGGTTGCAAAAGAAGTAGGTAGCTTAACCTTC-GGGAGGGCGCTTACCACTTTG
Klebsiella pneumoniae              GGGAGTGGGTTGCAAAAGAAGTAGGTAGCTTAACCTTC-GGGAGGGCGCTTACCACTTTG
Pseudomonas aeruginosa             GGGAGTGGGTTGCTCCAGAAGTAGCTAGTCTAACCGCA-AGGGGACGGTTACCACGGAG
Acinetobacter calcoaceticus        GGGAGTTTGTTGCACCAGAAGTAGTCTAACCGCA-AGGAGGACGCTTACCACGGTG
                                   *  ****  **   *            ****  *        *  *  **

Staphylococcus aureus              GGACAAATGATTGGGGTGAAGTCGTAACAAGGTAGCCGTATCGGAAGGTGCGGCTGGATC
Staphylococcus epidermidis         GGACAAATGATTGGGGTGAAGTCGTAACAAGGTAGCCGTATCGGAAGGTGCGGCTGGATC
Streptococcus pneumoniae           GGATAGATGATTGGGGTGAAGTCGTAACAAGGTAGCCGTATCGGAAG-----
Streptococcus agalactiae           GGATAGATGATTGGGGTGAAGTCGTAACAAGGTAGCCGTATCGGAAGG-----
Streptococcus pyogenes             GGATAGATGATTGGGGTGAAGTCGTAACAAGGTAGCCGTATCGGAAGGTGCGGCTGGATC
Enterococcus faecalis              GGATAGATGATTGGGGTGAAGTCGTAACAAGGTAGCC-----
Enterococcus faecium               GGATAGATGATTGGGGTGAAGTCGTAACAAGGTAGCCGTATCTGAAGGTGCGGCTGGATC
Proteus mirabilis                  TGATTCATGACTGGGGTGAAGTCGTAACAAGGTAACCGTAGGGGAACCTGCGGTTGGATC
Escherichia coli                   TGATTCATGACTGGGGTGAAGTCGTAACAAGGTAACCGTAGGGGAACCTGCGGTTGGATC
Serratia marcescens                TGATTCATGACTGGGGTGAAGTCGTAACAAGGTAACCGTAGGGGAACCTGCGGTTGGATC
Enterobacter aerogenes             TGATTCATGACTGGGGTGAAGTCGTAACAAGGTAACCGTAGGGGAACCTGCG-----
Enterobacter cloacae               TGATTCATGACTGGGGTGAAGTCGTAACAAGGTAACCGTAGGGGAACCTGCGGTTGGATC
Klebsiella pneumoniae              TGATTCATGACTGGGGTGAAGTCGTAACAAGGTAACCGTAGGGGAACCTGCGGTTGGATC
Pseudomonas aeruginosa             TGATTCATGACTGGGGTGAAGTCGTAACAAGGTAGCCGTAGGGGAACCTGCGGCTGGATC
Acinetobacter calcoaceticus        TGGCCGATGACTGGGGTGAAGTCGTAACAAGGTAACCA-----
```

Figure 1M

| | |
|---|---|
| Staphylococcus aureus | ACCTCCTTTCT |
| Staphylococcus epidermidis | ACCTCCTTTCT |
| Streptococcus pneumoniae | ---------- |
| Streptococcus agalactiae | ---------- |
| Streptococcus pyogenes | ACCTCCTTT-- |
| Enterococcus faecalis | ---------- |
| Enterococcus faecium | ACCTCCTTT-- |
| Proteus mirabilis | ACCTCCTTA-- |
| Escherichia coli | ACCTCCTTA-- |
| Serratia marcescens | ---------- |
| Enterobacter aerogenes | ---------- |
| Enterobacter cloacae | ACCTCCTTG-- |
| Klebsiella pneumoniae | ACCTCCTTT-- |
| Pseudomonas aeruginosa | ACCTCCTTA-- |
| Acinetobacter calcoaceticus | ---------- |

Figure 1N

BIOMARKERS AND USES THEREOF

CROSS REFERENCE TO RELATED APPLICATIONS

This is a divisional of U.S. application Ser. No. 16/614,697, filed Nov. 18, 2019, which is the § 371 U.S. National Stage of International Application No. PCT/AU2018/050471, filed May 17, 2018, which was published in English under PCT Article 21(2), which in turn claims the benefit of Australian Application No. 2017901846, filed May 17, 2017, all of which are incorporated herein by reference in their entirety.

INCORPORATION OF SEQUENCE LISTING

The Sequence Listing is submitted as an XML file named sequence.xml, created on Nov. 27, 2023, 117,962 bytes, which is incorporated by reference herein.

TECHNICAL FIELD

The present invention relates generally to methods and agents for identifying and/or classifying microbes. The methods and agents are based on the detection of polymorphisms within the 16S ribosomal RNA gene or gene products for bacteria, and within the 18S ribosomal RNA gene or gene products for yeast organisms and filamentous fungi. The invention also features methods for the treatment of infections of bacteria, yeast organisms or filamentous fungi based on the diagnostic methods of the present invention.

BACKGROUND

Rapid and accurate identification or classification of microbes (such as bacteria), yeast organisms and filamentous fungi in a sample is highly desirable.

First and foremost, rapid and accurate diagnosis of such infections can make the difference between life and death of a patient by allowing early implementation of an effective treatment or therapy.

Rapid and accurate identification or classification may assist in the implementation of effective control measures to manage, control, eradicate and/or eliminate microbes, yeast organisms or filamentous fungi in contaminated solutions, materials or foodstuffs, which may otherwise pose a threat to the wellbeing of organisms or the quality of production of the solutions, materials or foodstuffs.

Also, rapid and accurate identification or classification may assist with natural microbial, yeast organisms or filamentous fungi populations in a sample, such as, e.g., for ecological studies of microbial diversity, phylum spectrum and/or relative phylum abundance, or for monitoring deviation of a balance from a normal state in pathological conditions for an organism, such as, e.g., enteric, respiratory and skin disorders.

It may also be desirable to rapidly and accurately identify or classify microbes, yeast or filamentous fungi post therapy, treatment or modulation. For example, rapid microbial identification or classification may be of use in analysing the use of antibiotics, steroids, immune modulators, pre- and postbiotics, soil or water treatments, filtration, sterilization procedures and antiseptics.

Currently most diagnostic techniques commercially available typically require isolation and identification of live microbes, yeast organisms and filamentous fungi from a sample using culture, but this technique is negatively affected by considerable turn around time and suboptimal sensitivity, specificity and predictive value. It also can require more extensive handling of the organism, which can be particularly undesirable for some organisms such as security sensitive biological agents.

Alternative diagnostic techniques available include the use of polymerase chain reaction (PCR), particularly in conjunction with culture. However, a problem with such a technique is a lack of trust in early positive PCR results in the absence of culture results or relevant clinical or physical symptoms. Another problem with such a technique is, like with culture, a lack of sensitivity and specificity when attempting to detect small quantities of microbial nucleic acid in a background of host nucleic acid.

Hence, there is a recognized need for rapid and reliable techniques for accurate diagnosis of bacteria, yeast organisms and/or filamentous fungi.

SUMMARY OF INVENTION

In various aspects the present invention is predicated in part on high conservation of the 16S (Svedberg unit) ribosomal RNA (16S rRNA) gene between prokaryotes, including bacteria, and the high conservation of the 18S ribosomal RNA (18S rRNA) gene between yeast organisms and filamentous fungi, and also in part on the discovery of multiple single nucleotide polymorphisms (SNPs) within the 16S rRNA gene and 18S rRNA gene that may be useful in the identification and classification of microbes, particularly bacterial microbes, and yeast organisms and/or filamentous fungi in a sample.

Generally speaking, prokaryotes, including bacteria, contain 16S rRNA, which is a component of the 30S small subunit of the prokaryotic ribosome. The 16S rRNA is approximately 1,500 nucleotides in length and encoded by the 16S rRNA gene (also referred to as 16S rDNA), which is generally part of a co-transcribed operon also containing the 23S and 5S rRNA genes. Although the DNA sequence of the 16S rRNA genes (and thus the RNA sequence of the 16S rRNA molecules) is highly conserved between prokaryotes, there are regions of variation (Weisberg W. G., et al., 1991).

Similarly, the 18S rRNA gene in yeast and filamentous fungi is the homologue of the 16S rRNA gene in prokaryotes. The 18S rRNA is a component of the 40S small eukaryotic ribosomal subunit. The DNA sequence of the 18S rRNA gene (and thus the RNA sequence of the 18S rRNA molecules) is also highly conserved in yeast and filamentous fungi.

According to a first aspect of the invention, there is provided a method of identifying, partially identifying or classifying at least one bacterium, yeast organism or filamentous fungi in a sample.

In one embodiment, said method comprises analysing at least a portion of a bacterial 16S rRNA gene or gene product from the sample, or at least a portion of a yeast organism or filamentous fungi 18S rRNA gene or gene product from the sample, for the presence or absence of at least one single nucleotide polymorphism (SNP), wherein the at least one SNP in the at least a portion of the bacterial 16S rRNA gene or gene product is at a position corresponding to at least one of positions 273, 378, 412, 440, 488, 647, and 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43; or wherein the at least one bacterium, yeast organism or filamentous fungi in the sample is identified, partially identified or classified based on the presence or absence of the at least one SNP.

In another embodiment, said method comprises analysing at least a portion of a bacterial 16S rRNA gene or gene product from the sample, or at least a portion of a yeast organism or filamentous fungi 18S rRNA gene or gene product from the sample, for the presence or absence of at least one single nucleotide polymorphism (SNP), wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1;

wherein the at least one bacterium, yeast organism or filamentous fungi in the sample is identified, partially identified or classified based on the presence or absence of the at least one SNP.

According to a second aspect of the present invention, there is provided a method of identifying, partially identifying, classifying or diagnosing a bacterial, yeast organism or filamentous fungi infection in a subject.

In one embodiment, said method comprises analysing the presence or absence of at least one single nucleotide polymorphism (SNP) in at least a portion of a bacterial 16S rRNA gene or gene product or in at least a portion of a yeast organism or filamentous fungi 18S rRNA gene or gene product in a sample from the subject;

wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43; or wherein the presence or absence of said at least one SNP in the at least a portion of the 16S rRNA gene or gene product or in the at least a portion of the 18S rRNA gene or gene product is used to identify, partially identify, classify or diagnose the bacterial, yeast organism or filamentous fungi infection in the subject.

In another embodiment, said method comprises analysing the presence or absence of at least one single nucleotide polymorphism (SNP) in at least a portion of a bacterial 16S rRNA gene or gene product or in at least a portion of a yeast organism or filamentous fungi 18S rRNA gene or gene product in a sample from the subject;

wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1;

wherein the presence or absence of said at least one SNP in the at least a portion of the 16S rRNA gene or gene product or in the at least a portion of the 18S rRNA gene or gene product is used to identify, partially identify, classify or diagnose the bacterial, yeast organism or filamentous fungi infection in the subject.

According to a third aspect of the present invention, there is provided method of treating a subject having a bacterial, yeast organism or filamentous fungi infection, said method comprising:

identifying, partially identifying, classifying or diagnosing a bacterial, yeast organism or filamentous fungi infection in a subject according to the method of the second aspect, to identify, partially identify, classify or diagnose the bacterial, yeast organism or filamentous fungi infection in the subject;

administering to the subject a therapy or treatment agent for treating the bacterial, yeast organism or filamentous fungi infection in the subject.

According to a fourth aspect of the present invention, there is provided at least one isolated probe, tool or reagent.

In one embodiment of the fourth aspect, said at least one isolated probe, tool or reagent is capable of identifying, partially identifying, or classifying at least one bacteria, yeast organism or filamentous fungi in a sample, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

In another embodiment of the fourth aspect, said at least one isolated probe, tool or reagent is capable of identifying, partially identifying, or classifying at least one bacteria, yeast organism or filamentous fungi in a sample, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to another embodiment of the fourth aspect, said at least one isolated probe, tool or reagent is capable of discriminating between a sample that comprises at least one bacteria, yeast organism or filamentous fungi and a sample that does not comprise at least one bacteria, yeast organism or filamentous fungi, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

According to another embodiment of the fourth aspect, said at least one isolated probe, tool or reagent is capable of discriminating between a sample that comprises at least one bacteria, yeast organism or filamentous fungi and a sample that does not comprise at least one bacteria, yeast organism or filamentous fungi, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a fifth aspect of the present invention, there is provided a method of identifying, partially identifying, or classifying at least one bacterium, yeast organism or filamentous fungi in a sample.

In one embodiment, said method comprises:
combining with the sample the at least one isolated probe, tool or reagent of the fourth aspect; and
identifying, partially identifying, or classifying the at least one bacterium, yeast organism or filamentous fungi based on the presence or absence of at least one at least one single nucleotide polymorphism (SNP) in at least a portion of a bacterial 16S rRNA gene or gene product or at least a portion of a yeast organism or filamentous fungi 18S rRNA gene or gene product,
wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or
wherein the at least one SNP in the at least a portion of the bacterial 16S rRNA gene or gene product is in or corresponds to the 16S rRNA gene set forth in SEQ ID NO: 43.

In another embodiment, said method comprises:
combining with the sample the at least one isolated probe, tool or reagent of the fourth aspect; and
identifying, partially identifying, or classifying the at least one bacterium, yeast organism or filamentous fungi based on the presence or absence of at least one at least one single nucleotide polymorphism (SNP) in at least a portion of a bacterial 16S rRNA gene or gene product or at least a portion of a yeast organism or filamentous fungi 18S rRNA gene or gene product,
wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a sixth aspect of the present invention, there is provided an array (especially a microarray) comprising more than one said isolated probe, tool or reagent of the fourth aspect.

According to a seventh aspect of the present invention, there is provided a biochip comprising a solid substrate and at least one isolated probe, tool or reagent of the fourth aspect.

According to an eighth aspect of the present invention, there is provided a kit or assay.

In one embodiment of the eighth aspect, the kit or assay is for classifying or identifying at least one bacterium or at least one yeast organism or filamentous fungi in a sample, said kit or assay comprising: the at least one probe, tool or reagent of the fourth aspect; the array of the sixth aspect; and/or the biochip of the seventh aspect.

In another embodiment of the eighth aspect, the kit or assay is capable of discriminating between a sample that comprises at least one bacteria, yeast organism or filamentous fungi and a sample that does not comprise at least one bacteria, yeast organism or filamentous fungi, wherein the kit or assay comprises the probe, tool or reagent of the fourth aspect.

According to a ninth aspect of the present invention, there is provided at least one single nucleotide polymorphism (SNP).

In one embodiment, said at least one SNP is in at least a portion of a bacterial 16S rRNA gene or gene product or at least a portion of a yeast organism or filamentous fungi 18S rRNA gene or gene product for use as an indicator for classifying, identifying or partially identifying at least one bacterium, yeast organism or filamentous fungi in a sample;
wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or
wherein the at least one SNP in the at least a portion of the bacterial 16S rRNA gene or gene product is in or corresponds to the 16S rRNA gene set forth in SEQ ID NO: 43.

In another embodiment, said at least one SNP is in at least a portion of a bacterial 16S rRNA gene or gene product or at least a portion of a yeast organism or filamentous fungi 18S rRNA gene or gene product for use as an indicator for classifying, identifying or partially identifying at least one bacterium, yeast organism or filamentous fungi in a sample;
wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a tenth aspect of the present invention, there is provided a use of at least one single nucleotide polymorphism (SNP) in at least a portion of a bacterial 16S rRNA gene or gene product or at least a portion of a yeast organism or filamentous fungi 18S rRNA gene or gene product as defined in the first aspect, or the at least one isolated probe, tool or reagent of the fourth aspect in identifying, partially identifying or classifying at least one bacterium, yeast organism or filamentous fungi in a sample, wherein said at least one bacterium, yeast organism or filamentous fungi is identified, partially identified or classified based on the presence or absence of at least one SNP in at least a portion of the 16S rRNA gene or gene product or of at least a portion of the 18S rRNA gene or gene product from the sample.

According to an eleventh aspect of the present invention, there is provided a kit comprising a probe, tool or reagent for use in the method of any one of the first, second, third or fifth aspects of the present invention.

Further aspects of the invention are provided below.

According to a twelfth aspect of the present invention, there is provided at least one single nucleotide polymorphism (SNP) in a 16S rRNA gene for use or when used in identifying at least one bacterium in a sample or classifying bacteria in the sample; or at least one single nucleotide polymorphism (SNP) in a 18S rRNA gene for use or when used in identifying at least one yeast organism or filamentous fungi in a sample or classifying a yeast organism or filamentous fungi in the sample.

According to a thirteenth aspect of the present invention, there is provided at least one probe, tool or reagent for use or when used in identifying at least one bacterium in a sample or classifying bacteria in the sample, said at least one probe, tool or reagent is capable of specifically binding, detecting or identifying at least a portion of a 16S rRNA gene in the sample containing at least one SNP; or at least one probe, tool or reagent for use or when used in identifying at least one yeast organism or filamentous fungi in a sample or classifying at least one yeast organism or filamentous fungi in the sample, said at least one probe, tool or reagent is capable of specifically binding, detecting or identifying at least a portion of a 18S rRNA gene in the sample containing at least one SNP.

According to a fourteenth aspect of the present invention, there is provided at least one probe, tool or reagent for use or when used in identifying a bacterium in a sample or classifying bacteria in the sample, said at least one probe, tool or reagent comprising an oligonucleotide having a nucleotide sequence as set forth in any one of the of SEQ ID NOs:16-35, 56 or 57; or at least one probe, tool or reagent for use or when used in identifying at least one yeast organism or filamentous fungi in a sample or classifying at least one yeast organism or filamentous fungi in the sample, said at least one probe, tool or reagent comprising an oligonucleotide having a nucleotide sequence as set forth in any one of the of SEQ ID NOs:53-55.

According to a fifteenth aspect of the present invention, there is provided a use of the at least one SNP as defined in the twelfth aspect or the at least one probe, tool or reagent as defined in the thirteenth or fourteenth aspect in identifying at least one bacterium in a sample or classifying bacteria in the sample, wherein said at least one bacterium is identified or bacteria classified based on the presence of at least one SNP in a 16S rRNA gene from the sample as described above; or a use of the at least one SNP as defined in the twelfth aspect or the at least one probe, tool or reagent as defined in the thirteenth or fourteenth aspect in identifying at least one yeast organism or filamentous fungi in a sample or classifying at least one yeast organism or filamentous fungi in the sample, wherein said at least one yeast organism or filamentous fungi is identified or classified based on the presence of at least one SNP in a 18S rRNA gene from the sample as described above.

According to a sixteenth aspect of the present invention, there is provided a method of identifying at least one bacterium in a sample, said method comprising analysing a 16S rRNA gene from the sample for the at least one SNP as defined in the first aspect, wherein the at least one bacterium is identified based on the presence of the at least one SNP; or a method of identifying at least one yeast organism or filamentous fungi in a sample, said method comprising analysing a 18S rRNA gene from the sample for the at least one SNP as defined in the twelfth aspect, wherein the at least one yeast organism or filamentous fungi is identified based on the presence of the at least one SNP.

In one embodiment there is provided a method of identifying at least one bacterium in a sample, said method comprising analysing nucleic acid from the sample for at least one SNP in a bacterial 16S rRNA gene at a position corresponding to at least one of positions 273, 378, 412, 440, 488, 647, and 653 of the 16S rRNA gene set forth in SEQ ID NO: 1, wherein the at least one bacterium is identified based on the presence of the at least one SNP.

According to a seventeenth aspect of the present invention, there is provided a method of classifying bacteria in a sample, said method comprising analysing a 16S rRNA gene from the sample for the at least one SNP as defined in the first aspect, wherein the bacteria are classified based on the presence of the at least one SNP; or a method of classifying at least one yeast organism or filamentous fungi in a sample, said method comprising analysing a 18S rRNA gene from the sample for the at least one SNP as defined in the twelfth aspect, wherein the at least one yeast organism or filamentous fungi are classified based on the presence of the at least one SNP.

According to an eighteenth aspect of the present invention, there is provided a method of identifying at least one bacterium in a sample, said method comprising:
 combining with the sample the at least one probe, tool or reagent as defined in the thirteenth or fourteenth aspects; and
 identifying the at least one bacterium based on the presence of at least one SNP in a 16S rRNA gene from the sample as broadly described above; or
 a method of identifying at least one yeast organism or filamentous fungi in a sample, said method comprising:
 combining with the sample the at least one probe, tool or reagent as defined in the thirteenth or fourteenth aspects; and
 identifying the at least one yeast organism or filamentous fungi based on the presence of at least one SNP in a 18S rRNA gene from the sample as broadly described above.

According to a nineteenth aspect of the present invention, there is provided a method of classifying bacteria in a sample, said method comprising:
 combining with the sample the at least one probe, tool or reagent as defined in the thirteenth or fourteenth aspects; and
 classifying the bacteria based on the presence of at least one SNP in a 16S rRNA gene from the sample as broadly described above; or
 a method of classifying at least one yeast organism or filamentous fungi in a sample, said method comprising:
 combining with the sample the at least one probe, tool or reagent as defined in the thirteenth or fourteenth aspects; and
 classifying the at least one yeast organism or filamentous fungi based on the presence of at least one SNP in a 18S rRNA gene from the sample as broadly described above.

According to a twentieth aspect of the present invention, there is provided a method of diagnosing a bacterial infection in a subject, said method comprising analysing a 16S rRNA gene from a sample obtained from the subject for the at least one SNP as defined in the twelfth aspect, wherein the bacterial infection is diagnosed by identifying at least one causative bacterium in the sample based on the presence of the at least one SNP; or a method of diagnosing at least one yeast organism or filamentous fungi infection in a subject, said method comprising analysing a 18S rRNA gene from a sample obtained from the subject for the at least one SNP as defined in the twelfth aspect, wherein the at least one yeast organism or filamentous fungi infection is diagnosed by identifying at least one causative yeast organism or filamentous fungi in the sample based on the presence of the at least one SNP.

According to a twenty-first aspect of the present invention, there is provided a method of diagnosing a bacterial infection in a subject, said method comprising:
 combining with a sample obtained from the subject the at least one probe, tool or reagent as defined in the thirteenth or fourteenth aspects; and
 diagnosing the bacterial infection by identifying at least one causative bacterium in the sample based on the presence of the at least one SNP in a 16S rRNA gene from the sample as broadly described above; or a method of diagnosing at least one yeast organism or filamentous fungi infection in a subject, said method comprising:

combining with a sample obtained from the subject the at least one probe, tool or reagent as defined in the thirteenth or fourteenth aspects; and diagnosing the at least one yeast organism or filamentous fungi infection by identifying at least one causative bacterium in the sample based on the presence of the at least one SNP in a 18S rRNA gene from the sample as broadly described above.

According to a twenty-second aspect of the present invention, there is provided a method of treating a subject having a bacterial infection, said method comprising:

diagnosing the bacterial infection by identifying the at least one causative bacterium in the sample according to the method as defined in the twentieth or twenty-first aspects; and administering to the subject a therapy or treatment agent for treating the at least one causative bacterium identified to thereby treat the bacterial infection; or a method of treating a subject having at least one yeast organism or filamentous fungi infection, said method comprising:

diagnosing the at least one yeast organism or filamentous fungi infection by identifying the at least one causative bacterium in the sample according to the method as defined in the twentieth or twenty-first aspects; and administering to the subject a therapy or treatment agent for treating the at least one causative yeast organism or filamentous fungi identified to thereby treat the bacterial infection.

According to a twenty-third aspect of the present invention, there is provided an array of oligonucleotide probes for identifying at least one bacterium in a sample or classifying bacteria in the sample, said probes comprising oligonucleotides which hybridize to at least one SNP in a 16S rRNA gene in the sample as broadly described above; or an array of oligonucleotide probes for identifying at least one yeast organism or filamentous fungi in a sample or classifying at least one yeast organism or filamentous fungi in the sample, said probes comprising oligonucleotides which hybridize to at least one SNP in a 18S rRNA gene in the sample as broadly described above.

According to a twenty-fourth aspect of the present invention, there is provided a microarray comprising oligonucleotide probes for identifying at least one bacterium in a sample or classifying bacteria in the sample, said probes comprising oligonucleotides which hybridize to at least one SNP in a 16S rRNA gene in the sample as broadly described above; or a microarray comprising oligonucleotide probes for identifying at least one yeast organism or filamentous fungi in a sample or classifying at least one yeast organism or filamentous fungi in the sample, said probes comprising oligonucleotides which hybridize to at least one SNP in a 18S rRNA gene in the sample as broadly described above.

According to a twenty-fifth aspect of the present invention, there is provided a biochip comprising a solid substrate and at least one oligonucleotide probe for identifying at least one bacterium in a sample or classifying bacteria in the sample, said at least one probe comprising an oligonucleotide which hybridize to at least one SNP in a 16S rRNA gene in the sample as broadly described above; or a biochip comprising a solid substrate and at least one oligonucleotide probe for identifying at least one yeast organism or filamentous fungi in a sample or classifying at least one yeast organism or filamentous fungi in the sample, said at least one probe comprising an oligonucleotide which hybridize to at least one SNP in a 18S rRNA gene in the sample as broadly described above.

According to a twenty-sixth aspect of the present invention, there is provided a kit or assay for identifying at least one bacterium in a sample or classifying bacteria in the sample, said kit or assay comprising: the at least one probe, tool or reagent as described above; the array of oligonucleotide probes as described above; the microarray as described above; and/or the biochip as described above; or a kit or assay for identifying at least one yeast organism or filamentous fungi in a sample or classifying at least one yeast organism or filamentous fungi in the sample, said kit or assay comprising: the at least one probe, tool or reagent as described above; the array of oligonucleotide probes as described above; the microarray as described above; and/or the biochip as described above.

According to a twenty-seventh aspect of the present invention, there is provided a method of identifying, partially identifying, classifying or diagnosing an infection in a subject. In one embodiment of the twenty-seventh aspect, said infection is a bacterial, yeast organism or filamentous fungi infection, said method comprising assaying a biological sample obtained from the subject for a property of at least one bacterial 16S rRNA gene or gene product or a portion thereof or at least one yeast organism or filamentous fungi 18S rRNA gene or gene product or a portion thereof, wherein said assay comprises detecting at least one single nucleotide polymorphism (SNP) in the at least one bacterial 16S rRNA gene or gene product or a portion thereof or at least one yeast organism or filamentous fungi 18S rRNA gene or gene product or a portion thereof, wherein the at least one SNP in the bacterial 16S rRNA gene or gene product or a portion thereof is at a position corresponding to at least one of positions 273, 378, 412, 440, 488, 647, and 653 of the 16S rRNA gene set forth in SEQ ID NO: 1; or wherein the at least one SNP in the bacterial 16S rRNA gene or gene product or a portion thereof is in or corresponds to the 16S rRNA gene set forth in SEQ ID NO: 43; or wherein the at least one bacteria, yeast organism or filamentous fungi in the sample is identified, partially identified, classified or diagnosed based on the presence or absence of the at least one SNP.

In another embodiment of the twenty-seventh aspect, said infection is a bacterial, yeast organism or filamentous fungi infection, said method comprising assaying a biological sample obtained from the subject for a property of at least one bacterial 16S rRNA gene or gene product or a portion thereof or at least one yeast organism or filamentous fungi 18S rRNA gene or gene product or a portion thereof, wherein said assay comprises detecting at least one single nucleotide polymorphism (SNP) in the at least one bacterial 16S rRNA gene or gene product or a portion thereof or at least one yeast organism or filamentous fungi 18S rRNA gene or gene product or a portion thereof, wherein the at least one SNP in the bacterial 16S rRNA gene or gene product or a portion thereof is at a position corresponding to at least one of positions 273, 378, 412, 440, 488, 647, 653, 737, 755, 762 and 776 of the 16S rRNA gene set forth in SEQ ID NO: 1;

wherein the at least one bacteria, yeast organism or filamentous fungi in the sample is identified, partially identified, classified or diagnosed based on the presence or absence of the at least one SNP.

Features of the first to twenty-seventh aspects of the present invention, where appropriate, may be as described below.

In one embodiment, said at least one SNP in the at least a portion of the bacterial 16S rRNA gene or gene product is selected from SNPs at positions corresponding to at least one of positions 273, 378, 412, 440, 488, 647, 653, 737, 755, 762 and 776 of the 16S rRNA gene as set forth in SEQ ID NO:1. In some embodiments, more than one SNP may be used in the methods of the present invention. For example, at least two SNPs, at least three SNPs, at least four SNPS, at least five SNPs, at least six SNPs, at least seven SNPs, at least eight SNPs, at least nine SNPs, at least ten SNPs, or even at least eleven SNPs may be used.

In one embodiment, said at least one SNP in the at least a portion of the bacterial 16S rRNA gene or gene product is selected from SNPs at positions corresponding to positions 273, 378, 412, 440, 488, 647 and 653 of the 16S rRNA gene as set forth in SEQ ID NO:1. In some embodiments, more than one SNP may be used in the methods of the present invention. For example, at least two SNPs, at least three SNPs, at least four SNPS, at least five SNPs, at least six SNPs, or even at least seven SNPs may be used.

In another embodiment, said at least one SNP in the at least a portion of the bacterial 16S rRNA gene or gene product may be in or correspond to the 16S rRNA gene as set forth in SEQ ID NO: 43. The at least one SNP in the at least a portion of the bacterial 16S rRNA gene or gene product set forth in SEQ ID NO: 43 may be at a position corresponding to at least one of positions 746, 764, 771, or 785 of the 16S rRNA gene set forth in SEQ ID NO: 43 (or positions 737, 755, 762, or 776 of the 16S rRNA gene as set forth in SEQ ID NO:1). At least one said SNP, at least two said SNPs, at least three said SNPs or at least four said SNPs may be used.

In another embodiment, the at least one SNP in the at least a portion of the yeast organism or filamentous fungi 18S rRNA gene or gene product may be in or correspond to the 18S rRNA gene set forth in SEQ ID NO: 37. The at least one SNP in the at least a portion of the yeast organism or filamentous fungi 18S rRNA gene or gene product may be at a position corresponding to at least one of positions 343, 371, 388, 416, and 467 of the 18S rRNA gene set forth in SEQ ID NO: 37. At least one said SNP, at least two said SNPs, at least three said SNPs, at least four said SNPs or at least five said SNPs may be used.

In a further embodiment, said method comprises analysing at least a portion of a bacterial 16S rRNA gene or gene product from the sample, or at least a portion of a yeast organism or filamentous fungi 18S rRNA gene or gene product from the sample, for the presence or absence of:
single nucleotide polymorphisms in the bacterial 16S rRNA gene at a position corresponding to positions 273, 378, 412, 440, 488, 647, and 653 of the 16S rRNA gene set forth in SEQ ID NO: 1; or
single nucleotide polymorphisms in the bacterial 16S rRNA gene a position corresponding to positions 746, 764, 771, and 785 of the 16S rRNA gene set forth in SEQ ID NO: 43; or
single nucleotide polymorphisms in the yeast organism or filamentous fungi 18S rRNA gene at a position corresponding to positions 343, 371, 388, 416, and 467 of the 18S rRNA gene set forth in SEQ ID NO: 37.

In a further embodiment, said method comprises analysing at least a portion of a bacterial 16S rRNA gene or gene product from the sample, or at least a portion of a yeast organism or filamentous fungi 18S rRNA gene or gene product from the sample, for the presence or absence of:
single nucleotide polymorphisms in the at least a portion of the bacterial 16S rRNA gene or gene product at a position corresponding to at least four of positions 273, 378, 412, 440, 488, 647, 653, 737, 755, 762 and 776 of the 16S rRNA gene set forth in SEQ ID NO: 1; or
single nucleotide polymorphisms in the yeast organism or filamentous fungi 18S rRNA gene at a position corresponding to positions 343, 371, 388, 416, and 467 of the 18S rRNA gene set forth in SEQ ID NO: 37.

In some embodiments, the bacterium or bacteria is or are selected from among mammalian (e.g., human) associated bacteria, soil associated bacteria and water associated bacteria. In particular embodiments, the bacterium or bacteria may be a sepsis-associated bacterium or bacteria.

In some particular embodiments, the bacterium or bacteria is or are selected from among at least one of: *Acinetobacter* spp.; *Actinobaccillus* spp.; *Actinomadura* spp.; *Actinomyces* spp.; *Actinoplanes* spp.; *Aeromonas* spp.; *Agrobacterium* spp.; *Alistipes* spp.; *Anaerococcus* spp.; *Arthrobacter* spp.; *Bacillus* spp.; *Bacteroides* spp.; *Brucella* spp.; *Bulleidia* spp.; *Burkholderia* spp.; *Cardiobacterium* spp.; *Citrobacter* spp.; *Clostridium* spp.; *Cornyebacterium* spp.; *Dermatophilus* spp.; *Dorea* spp; *Enterobacter* spp.; *Enterococcus* spp.; *Erysipelothrix* spp.; *Escherichia* spp.; *Eubacterium* spp.; *Ewardsiella* spp.; *Faecalibacterium* spp.; *Filifactor* spp.; *Finegoldia* spp.; *Flavobacterium* spp.; *Francisella* spp.; *Gallicola* spp.; *Haemophilus* spp.; *Helococcus* spp.; *Holdemania* spp.; *Hyphomicrobium* spp.; *Klebsiella* spp.; *Lactobacillus* spp.; *Legionella* spp.; *Listeria* spp.; *Methylobacterium* spp.; *Micrococcus* spp.; *Micromonospora* spp.; *Mobiluncus* spp.; *Moraxella* spp.; *Morganella* spp.; *Mycobacterium* spp.; *Neisseria* spp.; *Nocardia* spp.; *Paenibacillus* spp.; *Parabacteroides* spp.; *Pasteurella* spp.; *Peptoniphilus* spp.; *Peptostreptococcus* spp.; *Planococcus* spp.; *Planomicrobium* spp.; *Plesiomonas* spp.; *Porphyromonas* spp.; *Prevotella* spp.; *Propionibacterium* spp.; *Proteus* spp.; *Providentia* spp.; *Pseudomonas* spp.; *Ralstonia* spp.; *Rhodococcus* spp.; *Roseburia* spp.; *Ruminococcus* spp.; *Salmonella* spp.; *Sedimentibacter* spp.; *Serratia* spp.; *Shigella* spp.; *Solobacterium* spp.; *Sphingomonas* spp.; *Staphylococcus* spp.; *Stenotrophomonas* spp.; *Streptococcus* spp.; *Streptomyces* spp.; *Tissierella* spp.; *Vibrio* spp.; and *Yersinia* spp.

In some more particular embodiments, the bacterium or bacteria is or are selected from among at least one of: *Acinetobacter baumannii*; *Acinetobacter calcoaceticus*; *Bacteroides fragilis*; *Bacteroides vulgatus*; *Citrobacter freundii*; *Enterobacter aerogenes*; *Enterobacter cloacae*; *Enterococcus avium*; *Enterococcus faecalis*; *Enterococcus faecium*; *Escherichia coli*; *Klebsiella oxytoca*; *Klebsiella pneumoniae*; *Proteus mirabilis*; *Pseudomonas aeruginosa*; *Serratia marcescens*; *Staphylococcus aureus*; *Staphylococcus epidermidis*; *Staphylococcus hominis*; *Staphylococcus saprophyticus*; *Stenotrophomonas maltophilia*; *Streptococcus agalactiae*; *Streptococcus anginosus*; *Streptococcus constellatus*; *Streptococcus intermedius*; *Streptococcus milleri*; *Streptococcus mitis*; *Streptococcus mutans*; *Streptococcus oralis*; *Streptococcus pneumoniae*; *Streptococcus pyogenes*; *Streptococcus sanguinis*; and
*Streptococcus sobrinus*.

In particular embodiments, the bacterium or bacteria is or are selected from among at least one of: *Acinetobacter calcoaceticus*; *Enterobacter aerogenes*; *Enterobacter cloacae*; *Enterococcus faecalis*; *Enterococcus faecium*; *Escherichia coli*; *Klebsiella pneumoniae*; *Proteus mirabilis*;

*Pseudomonas aeruginosa; Serratia marcescens; Staphylococcus aureus; Staphylococcus epidermidis; Streptococcus agalactiae; Streptococcus pneumoniae*; and *Streptococcus pyogenes*.

In particular embodiments, the bacterium or bacteria is or are selected from among at least one of: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae; Streptococcus pyogenes; Listeria monocytogenes; Clostridium perfringens; Corynebacterium jeikeium; Bacteroides fragilis; Neisseria meningitides; Haemophilus influenzae; Salmonella* sp.; and *Staphylococcus epidermidis*. In another embodiment, the bacterium or bacteria is or are selected from among at least one of: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae; Streptococcus pyogenes; Listeria monocytogenes; Clostridium perfringens; Corynebacterium jeikeium; Bacteroides fragilis; Neisseria meningitides; Haemophilus influenzae; Salmonella* sp.; *Staphylococcus epidermidis; Bacillus anthracis, Clostridium botulinum, Yersinia pestis, Francisella tularensis, Vibrio cholerae*, and *Burkholderia pseudomallei*.

In one embodiment the bacterium or bacteria is a Security Sensitive Biological Agent (SSBA). The SSBA may be a Tier 1 agent or a Tier 2 agent. Exemplary Tier 1 agents include one or more of: *Bacillus anthracis* (Anthrax), and *Yesinia pestis* (Plague). Exemplary Tier 2 agents include one or more of: *Clostridium botulinum* (botulism, especially toxin producing strains); *Francisella tularensis* (Tularaemia); *Salmonella Typhi* (typhoid), and *Vibrio cholerae* (especially Cholera serotypes 01 or 0139). In one embodiment the bacterium or bacteria is or are selected from among at least one of the group consisting of: *Bacillus anthracis, Clostridium botulinum, Yersinia pestis, Francisella tularensis, Vibrio cholerae*, and *Burkholderia pseudomallei*.

In one embodiment the yeast organism may be selected from among at least one of: *Candida* spp., *Cryptococcus* spp and *Rhodotorula* spp. Exemplary *Candida* spp. may include at least one of *Candida albicans, Candida tropicalis, Candida stellatoidea, Candida krusei, Candida parapsilosis, Candida glabrata, Candida guilliermondii, Candida viswanathii, Candida auris* and *Candida lusitaniae*. Exemplary *Cryptococcus* spp. may include at least one of *Cryptococcus neoformans* and *Cryptococcus gattii*. An exemplary *Rhodotorula* spp. may be *Rhodotorula mucilaginosa*.

In one embodiment the filamentous fungi may be selected from at least one of: *Aspergillus* spp. and *Fusarium* spp. Exemplary *Fusarium* spp. may include at least one of *Fusarium solani, Fusarium oxysporum, Fusarium verticillioides, Fusarium proliferatum, Fusarium avenaceum, Fusarium bubigeum, Fusarium culmorum, Fusarium graminearum, Fusarium langsethiae, Fusarium poae, Fusarium sporotrichioides, Fusarium tricinctum* and *Fusarium virguliforme*; especially at least one of *Fusarium solani, Fusarium oxysporum, Fusarium verticillioides* and *Fusarium proliferatum*. Exemplary *Aspergillus* spp. may include at least one of *Aspergillus fumigatus, Aspergillus flavus, Aspergillus clavatus, Aspergillus lentulus, Aspergillus terreus*, and *Aspergillus nidulans*; especially at least one of *Aspergillus fumigatus, Aspergillus flavus*, and *Aspergillus clavatus*; more especially *Aspergillus fumigatus*.

In one embodiment, the yeast organism or filamentous fungi is at least one of the group consisting of: *Candida albicans, Candida tropicalis, Candida parapsilosis, Candida glabrata, Fusarium* sp., *Aspergillus fumigatus*, and *Cryptococcus neoformans*.

In one embodiment, the bacteria, yeast organism or filamentous fungi is a human pathogen.

In some embodiments, the methods of the present invention may be used to analyse blood from a subject with systemic inflammatory response syndrome (SIRS) to determine the origin of the SIRS (for example bacteria, yeast organism or filamentous fungi). In other embodiments, the methods of the present invention may be used to determine whether a subject has sepsis having a bacterial, yeast organism or filamentous fungi infectious origin. In both embodiments, the methods of the present invention may be used to determine the presence of, differentiate and/or identify bacteria, yeast organism or filamentous fungi present in the sample.

SIRS is an overwhelming whole body reaction that may have an infectious aetiology or non-infectious aetiology (i.e., infection-negative SIRS, or inSIRS). Sepsis is SIRS that occurs during infection. Sepsis in this instance is diagnosed by a clinician (when there is suspected infection) or through culture of an organism. Both SIRS and sepsis are defined by a number of non-specific host response parameters including changes in heart and respiratory rate, body temperature and white cell counts (Levy et al., 2003; Reinhart et al., 2012).

In some embodiments, the at least one SNP or at least one probe, tool or reagent may be used to classify bacteria in a sample as Gram-positive bacterium or bacteria or Gram-negative bacterium or bacteria.

For example, in some embodiments, the bacterium or bacteria may be classified as Gram-positive based on any one of the above SNPs, especially at least one of positions 273, 378, 412, 440, 488, 647, and 653 of the 16S rRNA gene set forth in SEQ ID NO: 1. In one such embodiment, the bacteria or bacterium may be classified based on SNPs at positions corresponding to positions 273 and 653 of the 16S rRNA gene as set forth in SEQ ID NO:1, wherein the bacterium or bacteria is determined to be Gram-positive when there is an A at position 273 and a T at position 653.

For example, in another embodiment, the bacterium or bacteria may be classified as Gram-positive based on at least one SNP at a position corresponding to position 440 of the 16S rRNA gene as set forth in SEQ ID NO:1, wherein the bacterium or bacteria is determined to be Gram-positive when there is a T at position 440. Conversely, wherein the bacterium or bacteria is determined to be Gram-negative when there is not a T at position 440.

In yet other embodiments, the at least one SNP or at least one probe, tool or reagent may be used to classify groups of bacteria, yeast organisms or filamentous fungi in a sample.

For example, in some embodiments, the bacteria may be classified as belonging to a particular genus based on at least one SNP selected from the above SNPs. In one such embodiment, the bacteria may be classified as belonging to a particular genus based on at least one SNP selected from SNPs at positions corresponding to positions 412 and 647 of the 16S rRNA gene as set forth in SEQ ID NO:1. For example, the bacterium or bacteria in a sample may be classified as belonging to the *Staphylococcus* genus when there is a T at position 412. For example, the bacterium or bacteria in a sample may be classified as belonging to the *Enterococcus* genus when there is a G at position 647.

In yet other embodiments, the at least one SNP or at least one probe, tool or reagent may be used to identify a bacterium in a sample as described above.

For example, the bacterium *Enterobacter cloacae* may be identified in a sample based on at least one SNP at a position corresponding to position 653 of the 16S rRNA gene as set forth in SEQ ID NO:1, wherein the bacterium *Enterobacter cloacae* is identified when there is a G at position 653.

For example, bacterium selected from *Streptococcus pneumoniae, Streptococcus agalactiae* and *Streptococcus pyogenes* may be identified in a sample based on SNPs at positions corresponding to positions 378 and 488 of the 16S rRNA gene as set forth in SEQ ID NO:1, wherein the bacterium is: *Streptococcus pneumoniae* when there is an A at position 378 and a T at position 488; *Streptococcus agalactiae* when there is an A at position 378 and an A 488; and *Streptococcus pyogenes* when there is a G at position 378 and an A at position 488.

For example, in one embodiment, bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in a sample based on SNPs at positions corresponding to positions 273, 378, 412, 440, 488, 647 and 653 of the 16S rRNA gene as set forth in SEQ ID NO:1, wherein the bacterium is: *Acinetobacter calcoaceticus* when there is an A at positions 273, 440 and 647; *Enterobacter cloacae* when there is a G at position 653; *Escherichia coli* when there is a T at position 273 and a T at position 653; *Klebsiella pneumoniae* when there is a T at position 273, a C at positions 488 and 647 and an A at position 653; *Proteus mirabilis* when there is a C at positions 440 and 488 and a T at position 647; *Pseudomonas aeruginosa* when there is an A at position 440 and a T at position 647; *Streptococcus agalactiae* when there is an A at positions 378, 488 and 647; *Streptococcus pneumoniae* when there is T at positions 488 and 647; and *Streptococcus pyogenes* when there is G at position 378 and A at positions 488 and 647.

For example, in another embodiment, bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in a sample based on the presence of SNPs set forth in the following table:

TABLE 1

| Bacterial species | SNP position in the 16S rRNA gene as set forth in SEQ ID NO: 1 | | | | | | |
|---|---|---|---|---|---|---|---|
| | 273 | 378 | 412 | 440 | 488 | 647 | 653 |
| *Escherichia coli* | T | G | A | C | C | C | T |
| *Streptococcus pneumoniae* | A | A | A | T | T | T | T |
| *Streptococcus agalactiae* | A | A | A | T | A | A | T |
| *Streptococcus pyogenes* | A | G | A | T | A | A | T |
| *Proteus mirabilis* | T | G | A | C | C | T | A |
| *Enterobacter cloacae* | T | G | A | C | C | C | G |
| *Klebsiella pneumoniae* | T | G | A | C | C | C | A |
| *Pseudomonas aeruginosa* | A | G | A | A | C | T | A |
| *Acinetobacter calcoaceticus* | A | G | A | A | C | A | A |

For example, in another embodiment, bacterium selected from among *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella* sp., and *Staphylococcus epidermidis* may be identified in a sample based on the presence of SNPs set forth in the following table:

TABLE 2

| Bacterial species | SNP position in the 16S rRNA gene as set forth in SEQ ID NO: 1 | | | | | | | | | | |
|---|---|---|---|---|---|---|---|---|---|---|---|
| | 273 | 378 | 412 | 440 | 488 | 647 | 653 | 737 | 755 | 762 | 776 |
| *Escherichia coli* | T | G | A | C | C | C | T | C | G | T | G |
| *Streptococcus pneumoniae* | A | A | A | T | T | T | T | C | G | C | G |
| *Streptococcus agalactiae* | A | A | A | T | A | A | T | C | G | C | G |
| *Streptococcus pyogenes* | A | G | A | T | A | A | T | C | G | T | G |
| *Proteus mirabilis* | T | G | A | C | C | T | A | C | G | T | G |
| *Enterobacter cloacae* | T | G | A | C | C | C | G | C | G | T | G |
| *Klebsiella pneumoniae* | T | G | A | C | C | C | A | C | G | T | G |
| *Pseudomonas aeruginosa* | A | G | A | A | C | T | A | A | A | T | G |
| *Acinetobacter calcoaceticus* | A | G | A | A | C | A | A | A | G | T | A |
| *Enterococcus faecalis* | A | A | A | T | T | G | T | C | G | C | G |
| *Listeria monocytogenes* | A | A | A | T | T | A | G | C | G | T | G |

TABLE 2-continued

| Bacterial species | SNP position in the 16S rRNA gene as set forth in SEQ ID NO: 1 | | | | | | | | | | |
|---|---|---|---|---|---|---|---|---|---|---|---|
| | 273 | 378 | 412 | 440 | 488 | 647 | 653 | 737 | 755 | 762 | 776 |
| *Staphylococcus aureus* | A | G | T | T | C | A | T | T | G | T | G |
| *Clostridium perfringens* | A | G | T | C | C | T | A | C | G | C | G |
| *Corynebacterium jeikeium* | A | G | T | C | C | C | A | C | G | A | G |
| *Bacteroides fragilis* | A | G | T | T | A | C | T | C | A | C | T |
| *Neisseria meningitidis* | A | G | A | T | T | G | C | T | G | C | T |
| *Haemophilus influenzae* | A | G | A | C | C | G | A | C | G | C | G |
| *Serratia marcescens* | T | G | A | C | C | C | A | C | G | T | G |
| *Salmonella* sp. | A | G | A | C | C | C | T | C | G | T | G |
| *Staphylococcus epidermidis* | C | G | A | C | T | C | T | T | G | T | G |

In another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 746, 764, 771, or 785 of the 16S rRNA gene as set forth in SEQ ID NO:43, wherein the bacterium is: *Bacillus anthracis* when there is a T at position 746, A at position 764, C at position 771 and G at position 785; *Clostridium botulinum* type A or *Clostridium botulinum* type B when there is a T at position 746, G at position 764, C at position 771 and T at position 785; *Clostridium botulinum* type C when there is a T at position 746, A at position 764, T at position 771 and T at position 785; *Clostridium botulinum* type D when there is a C at position 746, A at position 764, T at position 771 and T at position 785; *Clostridium botulinum* type G when there is a T at position 746, G at position 764, C at position 771 and G at position 785; *Yersinia pestis* when there is a C at position 746, G at position 764, T at position 771 and G at position 785; *Francisella tularensis* when there is a T at position 746, A at position 764, G at position 771 and G at position 785; *Vibrio cholerae* when there is a C at position 746, A at position 764, T at position 771 and G at position 785; and *Burkholderia pseudomallei* when there is a C at position 746, G at position 764, C at position 771 and G at position 785.

For example, in another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on the presence of SNPs set forth in the following table:

TABLE 3

| Bacterial species | SNP position in the 16S rRNA gene as set forth in SEQ ID NO: 43 | | | |
|---|---|---|---|---|
| | 746 | 764 | 771 | 785 |
| *Bacillus anthracis* | T | A | C | G |
| *Clostridium botulinum* type A | T | G | C | T |
| *Clostridium botulinum* type B | T | G | C | T |
| *Clostridium botulinum* type C | T | A | T | T |
| *Clostridium botulinum* type D | C | A | T | T |
| *Clostridium botulinum* type G | T | G | C | G |
| *Yersinia pestis* | C | G | T | G |
| *Francisella tularensis* | T | A | G | G |

TABLE 3-continued

| Bacterial species | SNP position in the 16S rRNA gene as set forth in SEQ ID NO: 43 | | | |
|---|---|---|---|---|
| | 746 | 764 | 771 | 785 |
| *Vibrio cholerae* | C | A | T | G |
| *Burkholderia pseudomallei* | C | G | C | G |

The cumulative discriminatory index of the four SNPs used to identify the above organisms are 0.667 for 1 SNP; 0.889 for 2 SNPs; 0.944 for 3 SNPs; and 0.972 for 4 SNPs.

Position 746 of the 16S rRNA gene set forth in SEQ ID NO:43 corresponds to position 737 of the 16S rRNA gene set forth in SEQ ID NO:1. Position 764 of the 16S rRNA gene set forth in SEQ ID NO:43 corresponds to position 755 of the 16S rRNA gene set forth in SEQ ID NO:1. Position 771 of the 16S rRNA gene set forth in SEQ ID NO:43 corresponds to position 762 of the 16S rRNA gene set forth in SEQ ID NO:1. Position 785 of the 16S rRNA gene set forth in SEQ ID NO:43 corresponds to position 776 of the 16S rRNA gene set forth in SEQ ID NO:1.

Therefore, in another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 737, 755, 762, or 776 of the 16S rRNA gene as set forth in SEQ ID NO:1, wherein the bacterium is: *Bacillus anthracis* when there is a T at position 737, A at position 755, C at position 762 and G at position 776; *Clostridium botulinum* type A or *Clostridium botulinum* type B when there is a T at position 737, G at position 755, C at position 762 and T at position 776; *Clostridium botulinum* type C when there is a T at position 737, A at position 755, T at position 762 and T at position 776; *Clostridium botulinum* type D when there is a C at position 737, A at position 755, T at position 762 and T at position 776; *Clostridium botulinum* type G when there is a T at position 737, G at position 755, C at position 762 and G at position 776; *Yersinia pestis* when there is a C at position 737, G at position 755, T at position 762 and G at position 776; *Francisella tularensis* when there is a T at position 737, A at position 755, G at position 762 and G at position 776; *Vibrio cholerae* when there is a C at position 737, A at position 755, T at position 762 and G at position 776; and *Burkholderia pseudomallei* when there is a C at position 737, G at position 755, C at position 762 and G at position 776.

In another embodiment, yeast organism or filamentous fungi selected from among *Candida albicans, Candida tropicalis, Candida parapsilosis, Candida glabrata, Fusarium* spp., *Aspergillus fumigatus,* and *Cryptococcus* neoformans may be identified in a sample based on SNPs at positions corresponding to positions 343, 371, 388, 416, and 467 of the 18S rRNA gene set forth in SEQ ID NO: 37, wherein the yeast organism or filamentous fungi is: *Candida albicans* when there is a C at position 343, A at position 371, T at position 388, G at position 416 and G at position 467; *Candida tropicalis* when there is a C at position 343, A at position 371, C at position 388, G at position 416 and C at position 467; *Candida parapsilosis* when there is a C at position 343, A at position 371, C at position 388, G at position 416 and G at position 467; *Candida glabrata* when there is a T at position 343, A at position 371, C at position 388, G at position 416 and G at position 467; *Fusarium* spp. when there is a C at position 343, C at position 371, T at position 388, T at position 416 and G at position 467; *Aspergillus fumigatus* when there is a C at position 343, C at position 371, T at position 388, C at position 416 and G at position 467; and *Cryptococcus neoformans* when there is a C at position 343, A at position 371, T at position 388, T at position 416 and G at position 467.

For example, in another embodiment, yeast organism or filamentous fungi selected from among *Candida albicans*, *Candida tropicalis*, *Candida parapsilosis*, *Candida glabrata*, *Fusarium* spp., *Aspergillus fumigatus*, and *Cryptococcus neoformans* may be identified in a sample based on the presence of SNPs set forth in the following table:

TABLE 4

| Yeast organism or filamentous fungi species | SNP position in the 18S rRNA gene as set forth in SEQ ID NO: 37 | | | | |
|---|---|---|---|---|---|
| | 343 | 371 | 388 | 416 | 467 |
| Candida albicans | C | A | T | G | G |
| Candida tropicalis | C | A | C | G | C |
| Candida parapsilosis | C | A | C | G | G |
| Candida glabrata | T | A | C | G | G |
| Fusarium sp. | C | C | T | T | G |
| Aspergillus fumigatus | C | C | T | C | G |
| Cryptococcus neoformans | C | A | T | T | G |

The bacteria, yeast organism or filamentous fungi may be partially identified or classified based on one or more of the above SNPs.

In one embodiment nucleic acid is extracted from the sample prior to analysis in the methods of the invention (especially in the first and second aspects). In another embodiment, the step of analysing in the methods (especially in the first and second aspects) may comprise amplification of nucleic acid. The nucleic acid may be amplified by any method known in the art including, but not limited to polymerase chain reaction (PCR), ligase chain reaction (LCR) and reverse transcription-polymerase chain reaction (RT-PCR) using one or more oligonucleotides/primers that will amplify transcribed RNA.

The SNPs may be analysed by any method known in the art including, but not limited to: high resolution melt analysis, 5' nuclease digestion (including 5' nuclease digestion), molecular beacons, oligonucleotide ligation, microarray, restriction fragment length polymorphism; antibody detection methods; direct sequencing or any combination thereof. In one embodiment, the step of analysing in the methods (especially in the first and second aspects of the invention) comprises determining the presence or the absence of the at least one SNP using high resolution melt analysis, 5' nuclease digestion, molecular beacons, oligonucleotide ligation, microarray, restriction fragment length polymorphism, antibody detection methods; direct sequencing or any combination thereof. The SNPs may be detected by any method known in the art including, but not limited to: polymerase chain reaction (PCR); ligase chain reaction (LCR); hybridization analysis; high-resolution melt analysis; digestion with nucleases, including 5' nuclease digestion; molecular beacons; oligonucleotide ligations; microarray; restriction fragment length polymorphism; antibody detection methods; direct sequencing; or any combination thereof.

For example, in some embodiments, the identifying of bacterium or classifying of bacteria may further be based on DNA melting characteristics of the SNPs as broadly described above and their surrounding DNA sequences, preferably high-resolution melt analysis.

For example, in some such embodiments, the methods of the present invention may further include high-resolution melt (HRM) analysis to further analyse the DNA melting characteristics of the SNPs as broadly described above and their surrounding DNA sequences. In a particular embodiment, the HRM analysis may include forming a DNA amplification product (i.e., amplicon) containing at least one of the SNPs and at least one intercalating fluorescent dye and heating the DNA amplification product through its melting temperature ($T_m$). The HRM is monitored in real-time using the fluorescent dye incorporated into the DNA amplification product. The level of fluorescence is monitored as the temperature increases with the fluorescence reducing as the amount of double-stranded DNA reduces. Changes in fluorescence and temperature can be plotted in a graph known as a melt curve.

As a skilled addressee will understand, the $T_m$ of the DNA amplification product at which the two DNA strands separate is predictable, being dependent on the sequence of the nucleotide bases forming the DNA amplification product. Accordingly, it is possible to differentiate between DNA amplification products including a DNA amplification product containing a polymorphism (i.e., a SNP or SNPs) as the melt curves will appear different. Indeed, in some embodiments, it is possible to differentiate between DNA amplification products containing the same polymorphism based on differences in the surrounding DNA sequences.

For example, bacterium selected from among *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes* may be identified in a sample based on the presence of SNPs set forth in the following table and DNA melting characteristics of the SNPs and their surrounding DNA sequences:

TABLE 5

| Bacterial species | SNP position in the 16S rRNA gene as set forth in SEQ ID NO: 1 | | | | | | |
|---|---|---|---|---|---|---|---|
| | 273 | 378 | 412 | 440 | 488 | 647 | 653 |
| Escherichia coli | T | G | A | C | C | C | T |
| Staphylococcus aureus | A | G | T | T | C | A | T |
| Staphylococcus epidermidis | A | G | T | T | C | A | T |
| Streptococcus pneumoniae | A | A | A | T | T | T | T |
| Streptococcus agalactiae | A | A | A | T | A | A | T |

TABLE 5-continued

| | SNP position in the 16S rRNA gene as set forth in SEQ ID NO: 1 | | | | | | |
|---|---|---|---|---|---|---|---|
| Bacterial species | 273 | 378 | 412 | 440 | 488 | 647 | 653 |
| Streptococcus pyogenes | A | G | A | T | A | A | T |
| Enterococcus faecalis | A | A | A | T | T | G | T |
| Enterococcus faecium | A | A | A | T | T | G | T |
| Proteus mirabilis | T | G | A | C | C | T | A |
| Serratia marcescens | T | G | A | C | T | C | A |
| Enterobacter aerogenes | T | G | A | C | T | C | A |
| Enterobacter cloacae | T | G | A | C | C | C | G |
| Klebsiella pneumoniae | T | G | A | C | C | C | A |
| Pseudomonas aeruginosa | A | G | A | A | C | T | A |
| Acinetobacter calcoaceticus | A | G | A | A | C | A | A |

For example, bacterium selected from among *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella sp., Staphylococcus epidermidis* may be identified in a sample based on the presence of SNPs set forth in Table 2 and DNA melting characteristics of the SNPs and their surrounding DNA sequences.

In one embodiment, bacteria selected from *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes* may be identified in a sample based on SNPs at positions corresponding to positions 273, 378, 412, 440, 488, 647 and 653 of the 16S rRNA gene as set forth in SEQ ID NO:1 and high-resolution melt curve analysis of the SNPs and their surrounding DNA.

For example, the bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in the sample based on the SNP positions as described above and/or high-resolution melt curve analysis of the SNPs and their surrounding DNA.

In some embodiments. the bacterium selected from *Staphylococcus aureus; Staphylococcus epidermidis; Enterococcus faecalis; Enterococcus faecium; Serratia marcescens*; and *Enterobacter aerogenes* may be individually identified in a sample based on SNPs at positions corresponding to positions 412, 440, 488 and 647 of the 16S rRNA gene as set forth in SEQ ID NO:1, wherein: *Staphylococcus aureus* and *Staphylococcus epidermidis* may be identified when there is a T at position 412 and then further distinguished from one another based on high-resolution melt curve analysis of the DNA surrounding the SNP at position 412; *Enterococcus faecalis* and *Enterococcus faecium* may be identified when there is a G at position 647 and then further distinguished from one another based on high-resolution melt curve analysis of the DNA surrounding the SNP at position 647; *Serratia marcescens* and *Enterobacter aerogenes* may be identified when there is a C at positions 440 and 647 and a T at position 488 and may then be further distinguished from one another based on high-resolution melt curve analysis of the DNA surrounding the SNPs at any one of positions 440, 488 and 647.

In other embodiments, the bacterium selected from *Enterococcus faecalis; Enterococcus faecium; Streptococcus agalactiae*; and *Streptococcus pyogenes* may be identified in a sample based on at least one SNP at a position corresponding to position 378 of the 16S rRNA gene as set forth in SEQ ID NO:1 and high-resolution melt curve analysis of the DNA surrounding the SNP at position 378.

For example, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on the presence of SNPs set forth in the following table and DNA melting characteristics of the SNPs and their surrounding DNA sequences:

TABLE 6

| | SNP position in the 16S rRNA gene as set forth in SEQ ID NO: 43 | | | |
|---|---|---|---|---|
| Bacterial species | 746 | 764 | 771 | 785 |
| Bacillus anthracis | T | A | C | G |
| Clostridium botulinum type A | T | G | C | T |
| Clostridium botulinum type B | T | G | C | T |
| Clostridium botulinum type C | T | A | T | T |
| Clostridium botulinum type D | C | A | T | T |
| Clostridium botulinum type G | T | G | C | G |
| Yersinia pestis | C | G | T | G |
| Francisella tularensis | T | A | G | G |
| Vibrio cholerae | C | A | T | G |
| Burkholderia pseudomallei | C | G | C | G |

As noted above, position 746 of the 16S rRNA gene set forth in SEQ ID NO:43 corresponds to position 737 of the 16S rRNA gene set forth in SEQ ID NO:1. Position 764 of the 16S rRNA gene set forth in SEQ ID NO:43 corresponds to position 755 of the 16S rRNA gene set forth in SEQ ID NO:1. Position 771 of the 16S rRNA gene set forth in SEQ ID NO:43 corresponds to position 762 of the 16S rRNA gene set forth in SEQ ID NO:1. Position 785 of the 16S rRNA gene set forth in SEQ ID NO:43 corresponds to position 776 of the 16S rRNA gene set forth in SEQ ID NO:1.

In one embodiment, bacteria selected from *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 746, 764, 771, or 785 of the 16S rRNA gene as set forth in SEQ ID NO:43 (or positions 737, 755, 762, or 776 of the 16S rRNA gene as set forth in SEQ ID NO:1) and high-resolution melt curve analysis of the SNPs and their surrounding DNA.

For example, the bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in the sample based on the SNP positions as described above and/or high-resolution melt curve analysis of the SNPs and their surrounding DNA.

In another example, yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in a sample based on the presence of SNPs set forth in the following table and DNA melting characteristics of the SNPs and their surrounding DNA sequences:

TABLE 7

| Yeast organism or | SNP position in the 18S rRNA gene as set forth in SEQ ID NO: 37 | | | | |
|---|---|---|---|---|---|
| filamentous fungi species | 343 | 371 | 388 | 416 | 467 |
| *Candida albicans* | C | A | T | G | G |
| *Candida tropicalis* | C | A | C | G | C |
| *Candida parapsilosis* | C | A | C | G | G |
| *Candida glabrata* | T | A | C | G | G |
| *Fusarium* sp. | C | C | T | T | G |
| *Aspergillus fumigatus* | C | C | T | C | G |
| *Cryptococcus neoformans* | C | A | T | T | G |

In one embodiment, yeast organism or filamentous fungi selected from *Candida albicans, Candida tropicalis, Candida parapsilosis, Candida glabrata, Fusarium* spp., *Aspergillus fumigatus*, and *Cryptococcus neoformans* may be identified in a sample based on SNPs at positions corresponding to positions 343, 371, 388, 416, and 467 of the 18S rRNA gene set forth in SEQ ID NO: 37 and high-resolution melt curve analysis of the SNPs and their surrounding DNA.

For example, the yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in the sample based on the SNP positions as described above and/or high-resolution melt curve analysis of the SNPs and their surrounding DNA.

In some embodiments, nucleic acid may be extracted from the sample prior to analysis, identifying, classifying and/or diagnosing. Generally, the analysis, identifying, classifying and/or diagnosing may include amplification of the nucleic acid. In some embodiments, the analysis, identifying, classifying and/or diagnosing may further include administering a therapeutic agent to the subject, such as, e.g., an antibiotic. In another embodiment, a method of treatment (for example as in the third aspect of the present invention) may further comprise the step of determining whether the at least one bacteria, yeast organism or filamentous fungi is resistant to a therapeutic agent.

In one embodiment, any suitable sample may be used in the methods of the present invention. Exemplary samples may comprise sputum, saliva, blood, cerebrospinal fluid or urine samples.

The probe, tool or reagent may be, but is not limited to, an oligonucleotide, a primer, a nucleic acid, a polynucleotide, DNA, cDNA, RNA, a peptide or a polypeptide. These may be, for example, single stranded or double stranded, naturally occurring, isolated, purified, chemically modified, recombinant or synthetic.

The probe, tool or reagent may be, but is not limited to, an antibody or other type of molecule or chemical entity capable of specifically binding, detecting or identifying at least a portion of a 16S rRNA gene or an 18S rRNA gene in a sample containing at least one SNP.

The probe, tool or reagent may be any number or combination of the above, and the number and combination will depend on a desired result to be achieved—e.g., detection of SNP at a genomic level (genotyping) or at the RNA transcription level.

The probe, tool or reagent may be isolated. The probe, tool or reagent may be detectably labelled. A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In particular embodiments, the at least one probe, tool or reagent is for specifically binding, detecting or identifying of a SNP at the genomic level or transcription level, preferably the former.

In preferred embodiments, the at least one probe, tool or reagent is for specifically binding, detecting or identifying at least a portion of a 16S rRNA or a 18S rRNA gene or gene product in a sample containing at least one SNP as set forth in any one of Tables 1 to 7.

When identifying, partially identifying, classifying a bacterium, yeast organism or filamentous fungi, or identifying, partially identifying or diagnosing a bacterial, yeast organism or filamentous fungi infection a single probe (especially primer) may be used with each sample, or multiple probes (especially primers) may be used with each sample (i.e. in one pot). Such probes (especially primers) can be added to the raw solution obtained from amplification (such as PCR).

In one embodiment, the at least one probe, tool or reagent may comprise two primers, each of which hybridizes to at least a portion of a bacterial 16S rRNA gene (or gene product) or to at least a portion of a yeast organism or filamentous fungi 18S rRNA gene (or gene product), containing a SNP as defined above. In another embodiment, the at least one probe, tool or reagent may comprise a probe that hybridizes to at least a portion of a bacterial 16S rRNA gene or gene product or to at least a portion of a yeast organism or filamentous fungi 18S rRNA gene or gene product containing a SNP as defined above.

In one embodiment, said at least one probe, tool or reagent comprises an oligonucleotide having (or comprising or consisting of) a nucleotide sequence having at least 90%, at least 91%, at least 92%, at least 93%, at least 94%, at least 95%, at least 96%, at least 97%, at least 98%, at least 99% or 100% sequence homology or identity with the sequence as set forth in at least one of SEQ ID Nos 16-35 and 53-57. Said probe, tool or reagent may be a primer. Said probe, tool or reagent may comprise an oligonucleotide having a nucleotide sequence as set forth in at least one of SEQ ID NOs: 16-35 and 53-57.

In one aspect, the present invention provides at least one isolated probe, tool or reagent, wherein said at least one isolated probe, tool or reagent comprises an oligonucleotide having (or comprising or consisting of) a nucleotide sequence having at least 90%, at least 91%, at least 92%, at least 93%, at least 94%, at least 95%, at least 96%, at least 97%, at least 98%, at least 99% or 100% sequence homology or identity with the sequence as set forth in at least one of SEQ ID Nos 16-35 and 53-57. Said probe, tool or reagent may be a primer.

Suitable primers for identification of SNPs in the 16S rRNA sequence set forth in SEQ ID NO. 43 (especially for identification of the SNPs in Table 3) may be as shown in the Table below.

TABLE 8

| Forward primer sequence | Reverse primer sequence |
|---|---|
| 5'GTGTAGCGGTGAAAT GCGTAGAG 3' (SEQ ID NO. 56) | 5'TCGTTTACCGTGGACT ACCAGGG 3' (SEQ ID NO. 57) |

Suitable primers for identification of SNPs in the 18S rRNA sequence set forth in SEQ ID NO. 37 (especially for identification of the SNPs in Table 4) may be as shown in the Table below.

TABLE 9

| Forward primer sequence | Reverse primer sequence |
|---|---|
| 5'CATCCAAGGAAGGCAGCA GGCGCG 3' (SEQ ID NO. 53) | 5'GTTCAACTACGAGCTTTT TAAC 3' (SEQ ID NO. 54) |
| | 5'GTTCGACTACGAGCTTTT TAAC 3' (SEQ ID NO. 55) |

Any of the features described herein can be combined in any combination with any one or more of the other features described herein within the scope of the invention.

The above largely discusses the use of 16S rRNA and 18S rRNA genes. However, the above may also be applicable to 16S rRNA and to 18S rRNA and to other 16S rRNA and 18S rRNA gene products. Accordingly in some embodiments (and where appropriate), references to 16S rRNA gene and 18S rRNA gene above and below may be replaced with 16S rRNA gene product (or 16S rRNA) and 18S rRNA gene product (or 18S rRNA).

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which:

FIGS. 1A-1N are a CLUSTALW sequence alignment of the representative genes encoding 16S rRNA molecules from the following bacterial species: *Acinetobacter calcoaceticus* (SEQ ID NO: 15); *Enterobacter aerogenes* (SEQ ID NO: 11); *Enterobacter cloacae* (SEQ ID NO: 12); *Enterococcus faecalis* (SEQ ID NO: 7); *Enterococcus faecium* (SEQ ID NO: 8); *Escherichia coli* (SEQ ID NO: 1); *Klebsiella pneumoniae* (SEQ ID NO: 13); *Proteus mirabilis* (SEQ ID NO: 9); *Pseudomonas aeruginosa* (SEQ ID NO: 14); *Serratia marcescens* (SEQ ID NO: 10); *Staphylococcus aureus* (SEQ ID NO: 2); *Staphylococcus epidermidis* (SEQ ID NO: 3); *Streptococcus agalactiae* (SEQ ID NO: 5); *Streptococcus pneumoniae* (SEQ ID NO: 4); and *Streptococcus pyogenes* (SEQ ID NO: 6). Variable sequences, as determined by the CLUSTALW alignment were removed. The SNPs at positions corresponding to positions 273, 378, 412, 440, 488, 647 and 653 of the 16S rRNA gene from *E. coli* as set forth in SEQ ID NO:1 are highlighted together with the corresponding nucleotide in the aligned sequences.

Figure 13:
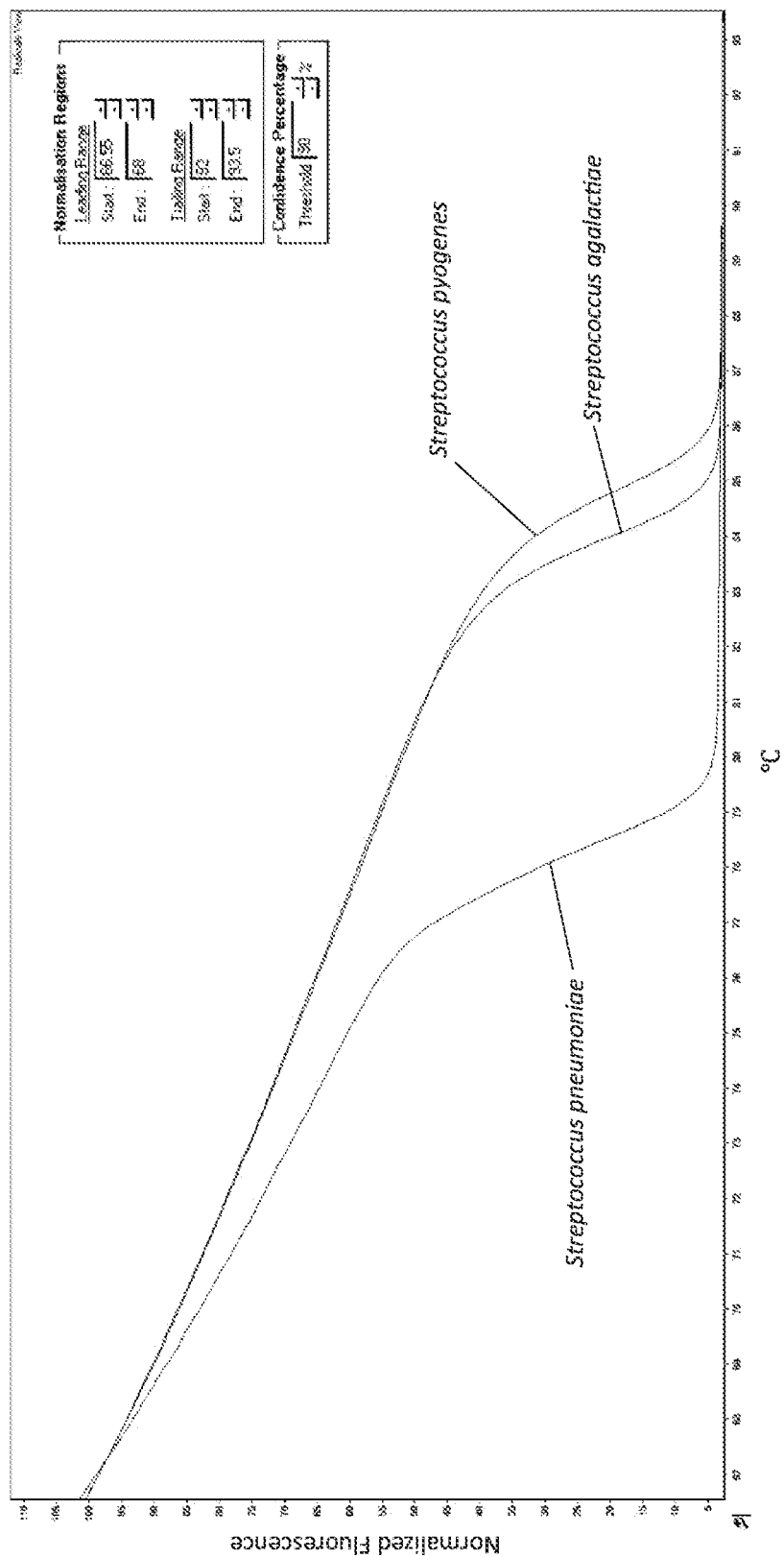

FIG. 13 shows a normalised HRM curves plot for *Streptococcus pneumonaie, Streptococcus agalactiae* and *Streptococcus pyogenes* for amplicons containing a SNP at a position corresponding to position 412 in the 16S rRNA gene as set forth in SEQ ID NO:1.

| KEY TO SEQUENCE LISTING |
| --- |
| SEQ ID NO: 1: *Escherichia coli* 16S rRNA gene (Genbank accession NR_102804.1); |
| SEQ ID NO: 2: *Staphylococcus aureus* 16S rRNA gene (Genbank accession NR_075000.1); |
| SEQ ID NO: 3: *Staphylococcus epidermidis* 16S rRNA gene (Genbank accession NR_074995.1); |
| SEQ ID NO: 4: *Streptococcus pneumoniae* 16S rRNA gene (Genbank accession NR_074564.1); |
| SEQ ID NO: 5: *Streptococcus agalactiae* 16S rRNA gene (Genbank accession NR_040821.1); |
| SEQ ID NO: 6: *Streptococcus pyogenes* 16S rRNA gene (Genbank accession NR_074091.1); |
| SEQ ID NO: 7: *Enterococcus faecalis* 16S rRNA gene (Genbank accession NR_074637.1); |
| SEQ ID NO: 8: *Enterococcus faecium* 16S rRNA gene (Genbank accession NR_042054.1); |
| SEQ ID NO: 9: *Proteus mirabilis* 16S rRNA gene (Genbank accession NR_074898.1); |
| SEQ ID NO: 10: *Serratia marcescens* 16S rRNA gene (Genbank accession NR_041980.1); |
| SEQ ID NO: 11: *Enterobacter aerogenes* 16S rRNA gene (Genbank accession NR_024643.1); |
| SEQ ID NO: 12: *Enterobacter cloacae* 16S rRNA gene (Genbank accession NR_028912.1); |
| SEQ ID NO: 13: *Klebsiella pneumoniae* 16S rRNA gene (Genbank accession NR_036794.1); |
| SEQ ID NO: 14: *Pseudomonas aeruginosa* 16S rRNA gene (Genbank accession NR_074828.1); |
| SEQ ID NO: 15: *Acinetobacter calcoaceticus* 16S rRNA gene (Genbank accession AB302132.1); |
| SEQ ID NO: 16: Forward Primer (CCTCTTGCCATCGGATGTG); |
| SEQ ID NO: 17: Reverse Primer (CCAGTGTGGCTGGTCATCCT); |
| SEQ ID NO: 18: Forward Primer (CCTACGGGAGGCAGCAGTAG); |
| SEQ ID NO: 19: Forward Primer (GGGAGGCAGCAGTAGGGAAT); |
| SEQ ID NO: 20: Reverse Primer (CGATCCGAAAACCTTCTTCACT); |
| SEQ ID NO: 21: Forward Primer (AAGACGGTCTTGCTGTCACTTATAGA); |
| SEQ ID NO: 22: Reverse Primer (CTATGCATCGTTGCCTTGGTAA); |

| KEY TO SEQUENCE LISTING |
| --- |
| SEQ ID NO: 23: Forward Primer (TGCCGCGTGAATGAAGAA); |
| SEQ ID NO: 24: Forward Primer (GCGTGAAGGATGAAGGCTCTA); |
| SEQ ID NO: 25: Forward Primer (TGATGAAGGTTTTCGGATCGT); |
| SEQ ID NO: 26: Reverse Primer (TGATGTACTATTAACACATCAACCTTCCT); |
| SEQ ID NO: 27: Reverse Primer (AACGCTCGGATCTTCCGTATTA); |
| SEQ ID NO: 28: Reverse Primer (CGCTCGCCACCTACGTATTAC); |
| SEQ ID NO: 29: Forward Primer (GTTGTAAGAGAAGAACGAGTGTGAGAGT); |
| SEQ ID NO: 30: Reverse Primer (CGTAGTTAGCCGTCCCTTTCTG); |
| SEQ ID NO: 31: Forward Primer (GCGGTTTGTTAAGTCAGATGTGAA); |
| SEQ ID NO: 32: Forward Primer (GGTCTGTCAAGTCGGATGTGAA); |
| SEQ ID NO: 33: Forward Primer (TCAACCTGGGAACTCATTCGA); |
| SEQ ID NO: 34: Reverse Primer (GGAATTCTACCCCCCTCTACGA); |
| SEQ ID NO: 35: Reverse Primer (GGAATTCTACCCCCCTCTACAAG); |
| SEQ ID NO: 36: *Aspergillus fumigatus* strain MJ-X6 18S ribosomal RNA gene, complete sequence (GenBank accession HM590663.1); |
| SEQ ID NO: 37: *Candida albicans* 18S ribosomal RNA gene, complete sequence (GenBank accession AF114470.1); |
| SEQ ID NO: 38: *Candida glabrata* strain SZ2 18S ribosomal RNA gene, partial sequence (GenBank accession KT229542.1); |
| SEQ ID NO: 39: *Candida parapsilosis* 18S ribosomal RNA gene, partial sequence (GenBank accession DQ218328.1); |
| SEQ ID NO: 40: *Candida tropicalis* 18S ribosomal RNA genes, partial sequence (GenBank accession AH009771.2); |
| SEQ ID NO: 41: *Cryptococcus neoformans* var. grubii H99 18S ribosomal RNA IRNA (GenBank accession/NCBI Reference Sequence: XR_001045463.1); |
| SEQ ID NO: 42: *Fusarium* sp. strain Z10 18S ribosomal RNA gene, partial sequence (GenBank accession MF973465.1); |
| SEQ ID NO: 43: *Bacillus anthracis* strain 2000031664 16S ribosomal RNA gene, partial sequence (GenBank accession AY138383.1); |
| SEQ ID NO: 44: *Burkholderia pseudomallei* 16S rRNA gene (GenBank accession AJ131790.1); |
| SEQ ID NO: 45: *Clostridium botulinum* type A rrn gene for 16S RNA (GenBank accession X68185.1); |

-continued

KEY TO SEQUENCE LISTING

SEQ ID NO: 46: *Clostridium botulinum* type B rrn gene for 16S RNA (GenBank accession X68186.1);

SEQ ID NO: 47: *Clostridium botulinum* type C rrn gene for 16S lRNA (GenBank accession X68315.1);

SEQ ID NO: 48: *Clostridium botulinum* type D rrn gene for 16S RNA (GenBank accession X68187.1);

SEQ ID NO: 49: *Clostridium botulinum* type G rrn gene for 16S lRNA (GenBank accession X68317.1);

SEQ ID NO: 50: *Francisella tularensis* strain B-38 16S ribosomal RNA, partial sequence (GenBank accession/NCBI Reference Sequence: NR_029362.1);

SEQ ID NO: 51: *Vibrio cholerae* strain DL2 16S ribosomal RNA gene, partial sequence (GenBank accession MG062858.1);

SEQ ID NO: 52: *Yersinia pestis* 16S rRNA gene, isolate: SS-Yp-116 (GenBank accession AJ232238.1);

SEQ ID NO: 53: Forward Primer (CATCCAAGGAAGGCAGCAGGCGCG);

SEQ ID NO: 54: Reverse Primer (GTTCAACTACGAGCTTTTTAAC);

SEQ ID NO: 55: Reverse Primer (GTTCGACTACGAGCTTTTTAAC);

SEQ ID NO: 56: Forward Primer (GTGTAGCGGTGAAATGCGTAGAG);

SEQ ID NO: 57: Reverse Primer (TCGTTTACCGTGGACTACCAGGG).

DETAILED DESCRIPTION

1. Definitions

Unless defined otherwise, all technical and scientific terms used herein have the same meaning as commonly understood by those of ordinary skill in the art to which the invention belongs. Although any methods and materials similar or equivalent to those described herein can be used in practice or testing of the present invention, preferred methods and materials are described. For the purposes of the present invention, the following terms are defined below.

The articles "a" and "an" are used herein to refer to one or to more than one (i.e., to at least one) of the grammatical objection of the article. By way of example, "an element" means one element or more than one element.

"Amplification product" or "amplicon" refers to a nucleic acid product generated by nucleic acid amplification techniques.

The term "biological sample" as used herein refers to a sample that may be extracted, untreated, treated, diluted or concentrated from a patient or subject. Suitably, the biological sample is selected from any part of a patient or subject's body, including, but not limited to, hair, skin, nails, tissues or bodily fluids such as sputum, saliva, cerebrospinal fluid, urine and blood.

In the present specification and claims (if any), the word "comprising" and its derivatives including "comprises" and "comprise" include each of the stated integers but does not exclude the inclusion of one or more further integers.

As used herein, "corresponding" nucleic acid positions or nucleotides refer to positions or nucleotides that occur at aligned loci of two or more nucleic acid molecules. Related or variant polynucleotides can be aligned by any method known to those of skill in the art. Such methods typically maximise matches, and include methods such as using manual alignments and by using the numerous alignment programs available (e.g., BLASTN) and others known to those of skill in the art. By aligning the sequences of polynucleotides, one skilled in the art can identify corresponding nucleotides or positions using identical nucleotides as guides. For example, by aligning sequences of the gene encoding the *E. coli* 16S rRNA (set forth in SEQ ID NO:1) with a gene encoding a 16S rRNA from another species, one of skill in the art can identify corresponding positions and nucleotides using conserved nucleotides as guides.

By "gene" is meant a unit of inheritance that occupies a specific locus on a genome and consists of transcriptional and/or translational regulatory sequences and/or a coding region and/or non-translated sequences (i.e., introns, 5' and 3' untranslated sequences).

By "gene product" is meant a product of the gene. For example, a gene product of the 16S rRNA gene includes 16S rRNA. Similarly, a gene product of the 18S rRNA gene includes 18S rRNA. Gene products also include, for example, cDNA sequences derived from the rRNA sequences. Gene products may also include products of the rRNA in which a SNP in the rRNA gene would result in a corresponding change in the product.

"Homology" refers to the percentage number of nucleic acids or amino acids that are identical or constitute conservative substitutions. Homology can be determined using sequence comparison programs such as GAP (Deveraux et al. 1984), which is incorporated herein by reference. In this way, sequences of a similar or substantially different length to those cited herein could be compared by insertion of gaps into the alignment, such gaps being determined, for example, by the comparison algorithm used by GAP.

"Hybridization" is used herein to denote the pairing of complementary nucleotide sequences to produce a DNA-DNA hybrid or a DNA-RNA hybrid. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. The nucleotide symbols are set forth in the following table:

TABLE 10

Nucleotide Symbols

| Symbol | Description |
| --- | --- |
| A | Adenosine |
| C | Cytidine |
| G | Guanosine |
| T | Thymidine |
| U | Uridine |
| M | Amino (adenosine, cytosine) |
| K | Keto (guanosine, thymidine) |
| R | Purine (adenosine, guanosine) |
| Y | Pyrimidine (cytosine, thymidine) |
| N | Any nucleotide |

By "isolated" is meant material that is substantially or essentially free from components that normally accompany it in its native state.

The term "oligonucleotide" as used herein refers to a polymer composed of a multiplicity of nucleotide residues (deoxynucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length generally from about 10 to 30 nucleotide residues, but the term can refer to molecules of any length, although the term "polynucleotide" or "nucleic acid" is typically used for large oligonucleotides.

The terms "patient" and "subject" are used interchangeably and refer to patients and subjects of human or other mammal and includes any individual being examined or treated using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., koalas, bears, wild cats, wild dogs, wolves, dingoes, foxes and the like).

The term "polymorphism" as used herein refers to a difference in the nucleotide or amino acid sequence of a given region as compared to a nucleotide or amino acid sequence in a homologous-region of another individual, in particular, a difference in the nucleotide or amino acid sequence of a given region which differs between individuals of the same species. A polymorphism is generally defined in relation to a reference sequence. Polymorphisms include single nucleotide differences, differences in more than one nucleotide, and single or multiple nucleotide insertions, inversions and deletions; as well as single amino acid differences, differences in sequence of more than one amino acid, and single or multiple amino acid insertions, inversions and deletions. A "polymorphic site" is the locus at which variation occurs. It shall be understood that where a polymorphism is present in a nucleic acid sequence, and reference is made to the presence of a particular base or bases at a polymorphic site, the present invention encompasses the complementary base or bases on the complementary strand at that site.

The term "polynucleotide" or "nucleic acid" as used herein designates mRNA, RNA, rRNA, cRNA, cDNA, or DNA. The term typically refers to oligonucleotides greater than 30 nucleotides residues in length.

By "primer" it is meant an oligonucleotide which, when paired with a strand of DNA, is capable of initiating the synthesis of a primer extension product in the presence of a suitable polymerizing agent. The primer is preferably a single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotides to several kilobases or more. Primers can be selected to be "substantially complementary" to the sequence on the template to which it is designed to hybridize and serve as a site for the initiation of synthesis. By "substantially complementary" it is meant that the primer is sufficiently complementary to hybridize with a target polynucleotide. In some embodiments, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labelled directly or indirectly.

The term "sepsis" is used herein in accordance with its normal meaning in clinical medicine, and includes, for example systemic and/or blood-borne infections, such as bacterial infections.

The term "sepsis-associated bacteria" refers to bacteria that have been identified as being able to cause sepsis in a subject, or have been identified in the blood of a subject with sepsis. "Mammalian (e.g., human) sepsis-associated bacteria" therefore refers to bacteria that have been identified as being able to cause sepsis in a mammalian (e.g., human) subject, or have been identified in the blood of a mammalian (e.g., human) subject with sepsis.

Examples of mammalian (e.g., human) sepsis-associated bacteria include *Acinetobacter baumannii, Actinobacillus hominis, Actinomyces massiliensis, Aeromonas hydrophila, Bacillus anthracis, Bacteroides fragilis, Brucella abortus, Burkholderia cepacia, Campylobacter coli, Campylobacter fetus, Campylobacter jejuni, Campylobacter lari, Cardiobacterium valvarum, Chlamydia trachomatis, Chlamydophila abortus, Chlamydophila pneumoniae, Citrobacter freundii, Clostridium difficile, Clostridium perfringens, Corynebacterium diphtheriae, Corynebacterium jeikeium, Corynebacterium urealyticum, Dermatophilus congolensis, Edwardsiella tarda, Enterobacter aerogenes, Enterobacter cloacae, Enterococcus faecalis, Enterococcus faecium, Erysipelothrix rhusiopathiae, Escherichia coli, Eubacterium desmolans, Flavobacterium ceti, Haemophilus ducreyi, Haemophilus influenzae, Haemophilus parahaemolyticus, Haemophilus parainfluenzae, Helicobacter cinaedi, Helicobacter pylori, Klebsiella oxytoca, Klebsiella pneumonia, Lactobacillus intestinalis, Legionella pneumophila, Leptospira interrogans, Listeria monocytogenes, Micrococcus luteus, Mobiluncus curtisii, Moraxella catarrhalis, Morganella morganii, Mycobacterium tuberculosis, Neisseria gon-* orrhoeae, Neisseria meningitidis, Nocardia asteroids, Nocardia brasiliensis, Pasteurella multocida, Peptostreptococcus stomatis, Porphyromonas gingivalis, Prevotella buccae, Prevotella intermedia, Prevotella melaninogenica, Proteus mirabilis, Providencia alcalifaciens, Pseudomonas aeruginosa, Rhodococcus equi, Salmonella enterica, Serratia marcescens, Shigella dysenteriae, Shigella sonnei, Staphylococcus aureus, Staphylococcus epidermidis, Staphylococcus haemolyticus, Staphylococcus hominis, Staphylococcus saprophyticus, Stenotrophomonas maltophila, Streptococcus agalactiae, Streptococcus anginosus, Streptococcus bovis, Streptococcus constellatus, Streptococcus dysgalactiae, Streptococcus intermedins, Streptococcus mitis, Streptococcus mutans, Streptococcus oralis, Streptococcus pneumoniae, Streptococcus pyogenes, Streptococcus sanguinis, Streptococcus sobrinus, Streptomyces amulatus, Streptomyces somaliensis, Veillonella atypica, Veillonella denticariosi, Veillonella dispar, Veillonella parvula, Veillonella rogosae, Vibrio cholerae, Yersinia enterocolitica and Yersinia pestis.

As used herein, "sepsis" is defined as SIRS with a presumed or confirmed infectious process. Confirmation of infectious process can be determined using microbiological culture or isolation of the infectious agent. From an immunological perspective, sepsis may be seen as a systemic response to microorganisms or systemic infection.

"Systemic Inflammatory Response Syndrome (SIRS)," as used herein, refers to a clinical response arising from a non-specific insult with two or more of the following measurable clinical characteristics; a body temperature greater than 38° C. or less than 36° C., a heart rate greater than 90 beats per minute, a respiratory rate greater than 20 per minute, a white blood cell count (total leukocytes) greater than 12,000 per mm$^3$ or less than 4,000 per mm$^3$, or a band neutrophil percentage greater than 10%. From an immunological perspective, it may be seen as representing a systemic response to insult (e.g., major surgery) or systemic inflammation. As used herein, therefore, "infection-negative SIRS (inSIRS)" includes the clinical response noted above but in the absence of an identifiable infectious process.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which identical nucleic acid base (e.g., A, T, C, G) occurs in both sequence to yield the number of matched positions, dividing the number of matched positions by the total number of positions in the window of comparison (i.e., the window size), and multiplying the result by 100 to yield the percentage of sequence identity (% seq. identity).

As used herein, the term single nucleotide polymorphism (SNP) refers to nucleotide sequence variations that occur when a single nucleotide (A, T, C or G) in the genome sequence is altered (such as via substitutions, addition or deletion). SNPs can occur in both coding (gene) and non-coding regions of the genome such as the genome of a prokaryotic or eukaryotic microorganism.

As used herein, the terms "treatment", "treating" and the like, refer to obtaining a desired pharmacological and/or physiological effect. The effect may be prophylactic in terms of completely or partially preventing an infection, condition or symptom thereof and/or may be therapeutic in terms of a partial or complete cure for an infection, condition and/or adverse affect attributable to the infection or condition.

"Treatment" as used herein covers any treatment of an infection or condition in a mammal (e.g., a human), and includes: (a) inhibiting the infection or condition, i.e., arresting its development; and (b) relieving the infection or condition, i.e., causing regression of the infection or condition.

2. Polymorphisms of the Invention

The present invention is based in part on the determination that SNPs within the 16S rRNA gene (and thus within the 16S rRNA molecule) of bacteria can be used to identify individual species of bacterium and/or classify bacteria based on genus or as Gram-positive or Gram-negative. The present invention is also based in part on the determination that SNPs within the 18S rRNA gene (and thus within the 18S rRNA molecule) can be used to identify, partially identify or classify yeast organisms or filamentous fungi.

2.1 Classification of Bacteria Using SNPs in 16S rRNA

The present invention provides methods for classifying bacterial species based on genus as well as methods for determining the Gram status of bacteria in a sample, i.e., determining whether the bacteria are Gram-positive or Gram-negative.

As demonstrated herein, polymorphisms at nucleotide positions of the gene encoding 16S rRNA (and thus of the 16S rRNA molecule itself) that correspond to positions 273 and 653 of the *E. coli* 16S rRNA gene as set forth in SEQ ID NO:1 can be used to determine the gram status of a selection of bacterial species within a sample, particularly including mammalian (e.g., human) pathogens (including the most commonly found bacterial species isolated by blood culture (Karlowsky et al. 2004)).

Most particularly and as shown in FIG. 1, the present invention provides methods for classifying bacterial species selected from among: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes.*

For example, the method for determining the Gram status of one of the bacterium listed in the above paragraph in a sample includes analysing nucleic acid from the sample for SNPs in the 16S rRNA gene (or 16S rRNA or DNA copy thereof) at positions corresponding to positions 273 and 653 of the 16S rRNA gene set forth in SEQ ID NO:1, wherein an A at position 273 and a T at position 653 indicates that the bacterium in the sample is Gram-positive.

Another method for determining the Gram status of one of the above said bacterium in a sample, includes analysing nucleic acid from the sample for SNPs in the 16S rRNA gene (or 16S rRNA or DNA copy thereof) at position 440 of the 16S rRNA gene set forth in SEQ ID NO:1, wherein a T at position 440 indicates that the bacterium in the sample is Gram-positive.

The method for classifying at least one of the above said bacterium in a sample as belonging to a particular genus includes analysing nucleic acid from the sample for SNPs in the 16S rRNA gene (or 16S rRNA or DNA copy thereof) at positions corresponding to positions 412 and 647 of the 16S rRNA gene set forth in SEQ ID NO:1, wherein: a T at position 412 indicates that the bacterium belongs to *Staphylococcus* genus; or a G at position 647 indicates that the bacterium belongs to the *Enterococcus* genus.

2.2 Identification of Bacteria Using SNPs in 16S rRNA and Yeast Organisms and Filamentous Fungi Using 18S rRNA The present invention also provides methods for identifying bacterium in a sample.

As demonstrated herein, polymorphisms at nucleotide positions of the gene encoding 16S rRNA (and thus of the 16S rRNA molecule itself) that correspond to any one of positions 273, 378, 412, 440, 488, 647 and 653 of the *E. coli* 16S rRNA gene as set forth in SEQ ID NO:1 can be used to identify bacterium within a sample, particularly including mammalian (e.g., human) pathogens (including the most commonly found bacterial species isolated by blood culture (Karlowsky et al. 2004)).

In one embodiment, and as shown in FIG. 1, the present invention provides methods for identifying bacterium selected from among: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes*.

The general rules for identifying the above bacterial species within a sample using the above SNPs are depicted in Table 1 and/or Table 5.

From the above bacteria, the bacterium *Enterobacter cloacae* can be identified in a sample by analysing nucleic acid from the sample for an SNP in the 16S rRNA gene (or 16S rRNA or DNA copy thereof) at a position corresponding to position 653 of the 16S rRNA gene set forth in SEQ ID NO:1, wherein a G at position 653 indicates that the bacterium is *Enterobacter cloacae*.

From the above bacteria, bacterium selected from *Streptococcus agalactiae, Streptococcus pneumoniae* and *Streptococcus pyogenes* can be identified in a sample by analysing nucleic acid from the sample for SNPs in the 16S rRNA gene (or 16S rRNA or DNA copy thereof) at positions corresponding to positions 378 and 488 of the 16S rRNA gene set forth in SEQ ID NO:1, wherein: an A at position 378 and a T at position 488 indicate that the bacterium is *Streptococcus pneumoniae*; an A at positions 378 and 488 indicate that the bacterium is *Streptococcus agalactiae*; and a G at position 378 and an A at position 488 indicate that the bacterium is *Streptococcus pyogenes*.

From the above bacteria, the method can identify bacterium selected from *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* in a sample by analysing nucleic acid from the sample for SNPs in the 16S rRNA gene (or 16S rRNA or DNA copy thereof) at positions corresponding to positions 273, 378, 412, 440, 488, 647 and 653 of the 16S rRNA gene set forth in SEQ ID NO:1, wherein: an A at positions 273, 440 and 647 indicates that the bacterium is *Acinetobacter calcoaceticus*; a G at position 653 indicates that the bacterium is *Enterobacter cloacae*; a T at positions 273 and 653 indicates that the bacterium is *E. coli*; a T at position 273, a C at positions 488 and 647 and an A at position 653 indicates that the bacterium is *Klebsiella pneumoniae*; a C at positions 440 and 488 and a T at position 647 indicates that the bacterium is *Proteus mirabilis*; an A at position 440 and a T at position 647 indicates that the bacterium is *Pseudomonas aeruginosa*; an A at positions 378, 488 and 647 indicates that the bacterium is *Streptococcus agalactiae*; a T at positions 488 and 647 indicates that the bacterium is *Streptococcus pneumoniae*; and a G at position 378 and an A at positions 488 and 647 indicates that the bacterium is *Streptococcus pyogenes*.

In addition to the above, the methods of the present invention can also be used to identify the presence of the following bacterium in a sample: *Staphylococcus aureus; S. epidermidis; Enterococcus faecalis; Enterococcus faecium; Serratia marcescens*; and *Enterobacter aerogenes*. The methods again include analysing nucleic acid from the sample for SNPs in the 16S rRNA gene (or 16S rRNA or DNA copy thereof) at positions corresponding to any one of positions 273, 378, 412, 440, 488, 647 and 653 of the 16S rRNA gene set forth in SEQ ID NO:1, wherein: a T at position 412 indicates that the sample includes the bacterium *Staphylococcus aureus* and/or *S. epidermidis*; a G at position 647 indicates that the sample includes the bacterium *Enterococcus faecalis* and/or *Enterococcus faecium*; and a C at positions 440 and 647 and a T at position 488 indicates that the sample includes the bacterium *Serratia marcescens* and/or *Enterobacter aerogenes*.

Further to the above, methods of the present invention can also be used to identify each of *Staphylococcus aureus; S. epidermidis; Enterococcus faecalis; Enterococcus faecium; Serratia marcescens*; and *Enterobacter aerogenes* in a sample. The methods include further analysing the nucleic acid from the sample with high-resolution melt analysis (see 3.8, below). High-resolution melt analysis allows nucleic acid sequences from different bacterium but containing the same SNP(s) to be differentiated from one another based upon variations in the surrounding nucleotide bases.

In another embodiment, the present invention provides methods for identifying bacterium selected from among: *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella* sp., and *Staphylococcus epidermidis*. The general rules for identifying the above bacterial species within a sample using the above SNPs are depicted in Table 2.

Similarly, as demonstrated herein, polymorphisms at nucleotide positions of the gene encoding 16S rRNA (and thus of the rRNA molecule itself) that correspond to positions 746, 764, 771, or 785 of the *Bacillus anthracis* 16S rRNA gene as set forth in SEQ ID NO:43 (or positions 737, 755, 762, or 776 of the 16S rRNA gene as set forth in SEQ ID NO:1) can be used to identify bacterium within a sample, particularly including mammalian (e.g., human) pathogens (including pathogens known as Security Sensitive Biological Agents).

In one embodiment, there is provided methods for identifying bacterium selected from among: *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei*.

The general rules for identifying the above bacterial species within a sample using the above SNPs are depicted in Table 3 and/or Table 6.

From the above bacteria, the bacterium *Bacillus anthracis* can be identified in a sample by analysing nucleic acid from the sample for an SNP in the 16S rRNA gene (or 16S rRNA or DNA copy thereof) of SEQ ID NO. 43, where a T at position 746, A at position 764, C at position 771 and G at position 785 indicates that the bacterium is *Bacillus anthracis*.

From the above bacteria, bacterium selected from *Clostridium botulinum* type A or *Clostridium botulinum* type B can be identified in a sample by analysing nucleic acid from the sample for an SNP in the 16S rRNA gene (or 16S rRNA or DNA copy thereof) of SEQ ID NO. 43, where a T at position 746, G at position 764, C at position 771 and T at position 785 indicates that the bacterium is *Clostridium botulinum* type A or *Clostridium botulinum* type B.

From the above bacteria, the bacterium *Clostridium botulinum* type C can be identified in a sample by analysing nucleic acid from the sample for an SNP in the 16S rRNA gene (or 16S rRNA or DNA copy thereof) of SEQ ID NO. 43, where a T at position 746, A at position 764, T at position 771 and T at position 785 indicates that the bacterium is *Clostridium botulinum* type C.

From the above bacteria, the bacterium *Clostridium botulinum* type D can be identified in a sample by analysing nucleic acid from the sample for an SNP in the 16S rRNA gene (or 16S rRNA or DNA copy thereof) of SEQ ID NO. 43, where a C at position 746, A at position 764, T at position 771 and T at position 785 indicates that the bacterium is *Clostridium botulinum* type D.

From the above bacteria, the bacterium *Clostridium botulinum* type G can be identified in a sample by analysing nucleic acid from the sample for an SNP in the 16S rRNA gene (or 16S rRNA or DNA copy thereof) of SEQ ID NO. 43, where a T at position 746, G at position 764, C at position 771 and G at position 785 indicates that the bacterium is *Clostridium botulinum* type G.

From the above bacteria, the bacterium *Yersinia pestis* can be identified in a sample by analysing nucleic acid from the sample for an SNP in the 16S rRNA gene (or 16S rRNA or DNA copy thereof) of SEQ ID NO. 43, where a C at position 746, G at position 764, T at position 771 and G at position 785 indicates that the bacterium is *Yersinia pestis*.

From the above bacteria, the bacterium *Francisella tularensis* can be identified in a sample by analysing nucleic acid from the sample for an SNP in the 16S rRNA gene (or 16S rRNA or DNA copy thereof) of SEQ ID NO. 43, where a T at position 746, A at position 764, G at position 771 and G at position 785 indicates that the bacterium is *Francisella tularensis*.

From the above bacteria, the bacterium *Vibrio cholerae* can be identified in a sample by analysing nucleic acid from the sample for an SNP in the 16S rRNA gene (or 16S rRNA or DNA copy thereof) of SEQ ID NO. 43, where a C at position 746, A at position 764, T at position 771 and G at position 785 indicates that the bacterium is *Vibrio cholerae*.

From the above bacteria, the bacterium *Burkholderia pseudomallei* can be identified in a sample by analysing nucleic acid from the sample for an SNP in the 16S rRNA gene (or 16S rRNA or DNA copy thereof) of SEQ ID NO. 43, where a C at position 746, G at position 764, C at position 771 and G at position 785 indicates that the bacterium is *Burkholderia pseudomallei*.

Further to the above, methods of the present invention may also be used to identify each of *Bacillus anthracis*, *Clostridium botulinum* type A, *Clostridium botulinum* type B, *Clostridium botulinum* type C, *Clostridium botulinum* type D, *Clostridium botulinum* type G, *Yersinia pestis*, *Francisella tularensis*, *Vibrio cholerae* and *Burkholderia pseudomallei* in a sample. The methods include further analysing the nucleic acid from the sample with high-resolution melt analysis (see 3.8, below).

Similarly, as demonstrated herein, polymorphisms at nucleotide positions of the gene encoding 18S rRNA (and thus of the rRNA molecule itself) that correspond to positions 343, 371, 388, 416, and 467 of the *Candida albicans* 18S rRNA gene set forth in SEQ ID NO: 37 can be used to identify bacterium within a sample, particularly including mammalian (e.g., human) pathogens.

In one embodiment, there is provided methods for identifying a yeast organism or filamentous fungi selected from among: *Candida albicans*, *Candida tropicalis*, *Candida parapsilosis*, *Candida glabrata*, *Fusarium* spp., *Aspergillus fumigatus*, and *Cryptococcus neoformans*.

The general rules for identifying the above bacterial species within a sample using the above SNPs are depicted in Table 4 and/or Table 7.

From the above yeast organism or filamentous fungi, the yeast organism *Candida albicans* can be identified in a sample by analysing nucleic acid from the sample for an SNP in the 18S rRNA gene (or 18S rRNA or DNA copy thereof) of SEQ ID NO. 37, where a C at position 343, A at position 371, T at position 388, G at position 416 and G at position 467 indicates that the yeast organism is *Candida albicans*.

From the above yeast organism or filamentous fungi, the yeast organism *Candida tropicalis* can be identified in a sample by analysing nucleic acid from the sample for an SNP in the 18S rRNA gene (or 18S rRNA or DNA copy thereof) of SEQ ID NO. 37, where a C at position 343, A at position 371, C at position 388, G at position 416 and C at position 467 indicates that the yeast organism is *Candida tropicalis*.

From the above yeast organism or filamentous fungi, the yeast organism *Candida parapsilosis* can be identified in a sample by analysing nucleic acid from the sample for an SNP in the 18S rRNA gene (or 18S rRNA or DNA copy thereof) of SEQ ID NO. 37, where a C at position 343, A at position 371, C at position 388, G at position 416 and G at position 467 indicates that the yeast organism is *Candida parapsilosis*.

From the above yeast organism or filamentous fungi, the yeast organism *Candida glabrata* can be identified in a sample by analysing nucleic acid from the sample for an SNP in the 18S rRNA gene (or 18S rRNA or DNA copy thereof) of SEQ ID NO. 37, where a T at position 343, A at position 371, C at position 388, G at position 416 and G at position 467 indicates that the yeast organism is *Candida glabrata*.

From the above yeast organism or filamentous fungi, the yeast organism *Cryptococcus neoformans* can be identified in a sample by analysing nucleic acid from the sample for an SNP in the 18S rRNA gene (or 18S rRNA or DNA copy thereof) of SEQ ID NO. 37, where a C at position 343, A at position 371, T at position 388, T at position 416 and G at position 467 indicates that the yeast organism is *Cryptococcus neoformans*.

From the above yeast organism or filamentous fungi, the filamentous fungi *Fusarium* spp. can be identified in a sample by analysing nucleic acid from the sample for an SNP in the 18S rRNA gene (or 18S rRNA or DNA copy thereof) of SEQ ID NO. 37, where a C at position 343, C at position 371, T at position 388, T at position 416 and G at position 467 indicates that the filamentous fungi is *Fusarium* spp.

From the above yeast organism or filamentous fungi, the filamentous fungi *Aspergillus fumigatus* can be identified in a sample by analysing nucleic acid from the sample for an SNP in the 18S rRNA gene (or 18S rRNA or DNA copy thereof) of SEQ ID NO. 37, where a C at position 343, C at position 371, T at position 388, C at position 416 and G at position 467 indicates that the filamentous fungi is *Aspergillus fumigatus*.

Further to the above, methods of the present invention may also be used to identify each of *Candida albicans*, *Candida tropicalis*, *Candida parapsilosis*, *Candida glabrata*, *Fusarium* spp., *Aspergillus fumigatus*, and *Cryptococcus neoformans* in a sample. The methods include further analysing the nucleic acid from the sample with high-resolution melt analysis (see 3.8, below).

3. Screening for Specific Polymorphisms to Identify and/or Classify Bacteria, Yeast Organisms and Filamentous Fungi According to the Invention Steps/techniques of isolating a biological sample from a subject, processing a biological sample, genomic DNA extraction, RNA extraction, DNA detection and characterisation, RNA detection and characterisation, DNA sequencing, DNA sequence analyses, SNP genotyping studies, RNA location and identification, RNA profiling and RNA screening, RNA sequencing, RNA sequence analyses can be carried out in any suitable way.

Any method known in the art to detect one or more SNPs can be used in the methods described herein to classify and/or identify bacterial species within a sample. In particular embodiments, the methods also facilitate in the narrowing down or, in some cases, confirming of one bacterial species (or yeast organism or filamentous fungi species) over another. Numerous methods are known in the art for determining the nucleotide occurrence at a particular position corresponding to a single nucleotide polymorphism in a sample. The various tools for the detection of polymorphisms include, but are not limited to, DNA sequencing, scanning techniques, hybridization based techniques, extension based analysis, high-resolution melting analysis, incorporation based techniques, restriction enzyme based analysis and ligation based techniques.

The methods according to the present invention can identify polymorphisms described herein within the 16S rRNA or 18S rRNA genes, within the 16S rRNA or 18S rRNA molecule or within DNA copies thereof, and for either strand. In some examples, the methods of detecting the polymorphisms utilise a first step of amplification, and amplification can be from the 16S rRNA or 18S rRNA gene or from DNA copies of the 16S rRNA or 18S rRNA molecule.

The nucleic acid may be from a biological sample from a subject or from an environmental sample, such as an air, soil or water sample, a filtrate, a food or manufactured product, or swap from a surface, such as from a medical instrument or work place surface. The subject may be a human subject or non-human subject, such as a mammalian subject, such as a primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., koalas, bears, wild cats, wild dogs, wolves, dingoes, foxes and the like). Biological samples from a subject may be from any part of the subject's body, including but not limited to bodily fluids such as blood, saliva, sputum, urine, cerebrospinal fluid, faeces, cells, tissue or biopsies. In other examples, the nucleic acid is obtained from cultured cells.

The nucleic acid that is analysed according to the methods of the present invention may be analysed while within the sample, or may first be extracted from the sample, e.g., isolated from the sample prior to analysis. Any method for isolating nucleic acid from a sample can be used in the methods of the present invention, and such methods are well known to those of skill in the art. The extracted nucleic acid can include DNA and/or RNA (including mRNA or rRNA). In some examples, a further step of reverse transcription can be included in the methods prior to analysis. Thus, the nucleic acid to be analysed can include the 16S rRNA gene, 18S rRNA gene, 16S rRNA, 18S rRNA, a DNA copy of the 16S rRNA or the 18S rRNA or any combination thereof. The nucleic acid can also contain portions of the 16S rRNA gene, 18S rRNA gene, 16S rRNA, 18S rRNA or a DNA copy of the 16S rRNA or the 18S rRNA, providing the portions containing the nucleic acid positions that are being analysed for SNPs.

In some instances, the methods include amplification of the nucleic acid. In such instances, suitable nucleic acid amplification techniques are well known to a person or ordinary skill in the art, and include polymerase chain reaction (PCR) as for example described in Ausubel et al., Current Protocols in Molecular Biology (John Wiley & Sons, Inc. 1994-1998, strand displacement amplification (SDA) as for example described in U.S. Pat. No. 5,422,252, rolling circle replication (RCR) as for example described in Liu et al. (1996) and in WO 92/01813 and WO 97/19193, nucleic acid sequence-based amplification (NASBA) as for example described in Sooknanan et al., (1994), ligase chain reaction (LCR), simple sequence repeat analysis (SSR), branched DNA amplification assay (b-DNA), transcription amplification and self-sustained sequence replication, and Q-β replicase amplification as for example described in Tyagi et al. (1996).

Such methods can utilise one or more oligonucleotide probes or primers, including, for example, an amplification primer pair, that selectively hybridize to a target polynucleotide, which contains one or more SNPs. Oligonucleotide probes useful in practicing a method of the invention can include, for example, an oligonucleotide that is complementary to and spans a portion of the target polynucleotide, including the position of the SNP, which the presence of a specific nucleotide at the polymorphic site (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the polymorphic site is complementary to the corresponding nucleotide of the probe.

Primers may be manufactured using any convenient method of synthesis. Examples of such methods may be found in "Protocols for Oligonucleotides and Analogues; Synthesis and Properties", Methods in Molecular Biology Series, Volume 20, Ed. Sudhir Agrawal, Humana ISBN: 0-89603-247-7, 1993. The primers may also be labelled to facilitate detection.

Any method useful for the detection of SNPs can be used in the present invention, and many different methods are known in the art for SNP genotyping (for review see Syvanen, A. C. (2001); Kim, S. and Misra, A., (2007)). Such methodology may consist of the use of three steps in succession, including a "reaction" (e.g., hybridization, ligation, extension and cleavage) followed by "separation" (e.g., solid phase microtitre plates, microparticles or arrays, gel electrophoresis, solution-phase homogenous or semi-homogenous). No single ideal SNP genotyping method exists for all applications, and it is well within the skill of a skilled artisan to determine the most appropriate method given the various parameters, such as sample size and number of SNPs to be analysed.

Example technologies that particularly lend themselves to clinical use and that rely on querying small numbers of SNPs, are fast, sensitive (through amplification of nucleic acid in the sample), one-step, output measured in real-time, able to be multiplexed and automated, comparatively inexpensive, and accurate include, but are not limited to, TaqMan® assays (5' nuclease assay, Applied Biosystems), high-resolution melt analysis, molecular beacon probes such as LUX® (Invitrogen) or Scorpion® probes (Sigma Aldrich), and Template Directed Dye Incorporation (TDI, Perkin Elmer).

For example, TaqMan® (Applied Biosystems) uses a combination of hybridization with allele-specific probes, solution phase homogenous, and fluorescence resonance energy transfer. The TaqMan® assay relies on forward and reverse primers and Taq DNA polymerase to amplify nucleic acid in conjunction with 5'-nuclease activity of Taq DNA polymerase to degrade a labelled probe designed to bind across the SNP site(s). Reaction, separation and detection can all be performed at the same time and results read in real-time as the reaction proceeds. While such an approach does not lend itself to analysing large numbers of SNPs simultaneously it is particularly suitable for querying small numbers of SNPs quickly, sensitively and accurately at a reasonable cost.

Although some methods may be more suitable than others, any method known in the art to detect one or more SNPs can be used in the methods described herein to classify and/or identify bacteria and/or bacterium in a sample. Non-limiting examples of such methods are described below.

3.1 Nucleic Acid Sequencing Techniques

In some embodiments, the polymorphism is identified through nucleic acid sequencing techniques. Specifically, amplification products which span a SNP locus can be sequenced using traditional sequencing methodologies (e.g., the "dideoxy-mediated chain termination method", also known as the "Sanger Method" (Sanger, F., et al. (1975)) and the "chemical degradation method", also known as the "Maxam-Gilbert method" (Maxam, A. M., et al., 1977) both references are herein incorporated by reference to determine the nucleotide occurrence at the SNP loci.

Boyce-Jacino et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target. Other sequencing technologies such as a Denaturing High Pressure Liquid Chromatography or mass spectrometry may also be employed.

In other illustrative examples, the sequencing method comprises a technique known as Pyrosequencing™. The approach is based on the generation of pyrophosphate whenever a deoxynucleotides is incorporated during polymerization of DNA. The generation of pyrophosphate is coupled to a luciferase-catalysed reaction resulting in light emission if the particular deoxynucleotides added is incorporated, yielding a quantitative and distinctive pyrogram. Sample processing includes PCR amplification with a biotinylated primer, isolation of the biotinylated single strand amplicon on streptavidin coated beads (or other solid phase) and annealing of a sequencing primer. Samples are then analysed by a Pyrosequence™, which adds a number of enzymes and substrates required for the indicator reaction, including sulfurylase and luciferase, as well as pyrase for degradation of unincorporated molecules. The sample is then interrogated by addition of the four deoxynucleotides. Light emission can be detected by a charge coupled device (CCD) camera and is proportional to the number of nucleotides incorporated. Results are automatically assigned by pattern recognition.

Alternatively, methods of the invention can identify nucleotide occurrences at polymorphic sites within a nucleic acid using a "micro-sequencing" method. Micro-sequencing methods determine the identity of only a single nucleotide at a "predetermined" site. Such methods have particular utility in determining the presence and identity of polymorphisms in a target polynucleotide. Such micro-sequencing methods, as well as other methods for determining the nucleotide occurrence at a polymorphic site are discussed in U.S. Pat. No. 6,294,336, which is incorporated herein by reference.

Micro-sequencing methods include the Genetic Bit Analysis™ method disclosed in WO 92/15712. Additional, primer-guided, nucleotide incorporation procedures for assaying polymorphic sites in DNA have also been described (Komher, J. S., et al., 1989); Sokolov, B. P., 1990; Syvanen, A. C., et al., 1990; Kuppuswamy, M. N., et al., 1991; Prezant, T. R., et al. 1992; Ugozzoli, L., et al., 1992; Nyren, P., et al. 1993; and WO 89/10414). These methods differ from Genetic Bit Analysis™ in that they all rely on incorporation of labelled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al. 1993).

Further micro-sequencing methods have been provided by U.S. Pat. No. 4,656,127 and French Patent No. 2,650,840 (WO 91/02087) which involve a solution-based method for determining the identity of a nucleotide of a polymorphic site. As in the method of the US patent, a primer is employed that is complementary to allelic sequences immediately 3' to a polymorphic site.

In other illustrative examples, U.S. Pat. No. 5,002,867, for example, describes a method for determining nucleic acid sequences via hybridization with multiple mixtures of oligonucleotide probes. In accordance with such methods, the sequence of a target polynucleotide is determined by permitting the target to sequentially hybridize with sets of probes having an invariant nucleotide at one position, and variant nucleotides at other positions. The method determines the nucleotide sequence of the target by hybridizing the target with a set of probes, and then determining the number of sites that at least one member of the set is capable of hybridizing to the target (i.e., the number of matches). The procedure is typically repeated until each member of a set of probes has been tested.

Alternatively, the template-directed dye-terminator incorporation assay with fluorescence polarization detection (FP-TDI) assay (Chen et al. 1999) is a version of the primer extension assay that is also called mini-sequencing or the single base extension assay (Syvanen, A. C., et al., 1990). The primer extension assay is capable of detecting SNPs. The DNA sequencing protocol ascertains the nature of the one base immediately 3' to the SNP-specific sequencing primer that is annealed to the target DNA immediately upstream from the polymorphic site. In the presence of DNA polymerase and the appropriate dideoxyribonucleoside triphosphate (ddNTP), the primer is extended specifically by one base as dictated by the target DNA sequence at the polymorphic site. By determining which ddNTP is incorporated, the allele(s) present in the target DNA can be inferred.

3.2 Polymorphism Hybridization Based Techniques

Hybridization techniques for detecting polymorphisms within a nucleotide sequence can include, but are not restricted to the TaqMan® assay (Applied Biosystems), dot blots, reverse dot blot, Multiplex-allele-specific diagnostic assays (MASDA), Dynamic allele-specific hybridization (DASH) (Jobs et al. 2003), molecular beacons and Southern Blots.

The TaqMan® assay (also known as a 5' nuclease assay or 5' digestion assay) for identifying SNPs within a nucleotide sequence is based on the nuclease activity of Taq polymerase that displaces and cleaves the oligonucleotide probe hybridized to the target DNA, generating a fluorescent signal. TaqMan® probes specific for a particular SNP are required, with each probe having different fluorescent dyes attached to the 5' end and quencher attached to the 3' end. When the probes are intact, the quencher interacts with the fluorophore by fluorescence resonance energy transfer (FRET), quenching their fluorescence. During the PCT annealing step, the TaqMan® probes hybridize to the target DNA. In the extension step, the fluorescent dye is cleaved by the nuclease activity of the Taq polymerase, leading to an increase in fluorescence by the reporter dye. Mismatch probes are displaced without fragmentation. The genotype of a sample is determined by measuring the signal intensity of the two different dyes.

Another useful SNP identification method includes DASH (dynamic allele-specific hybridization), which encompasses dynamic tracking of probe (oligonucleotide) to target (PCR product) hybridization as the reaction temperature is steadily increased to identify polymorphisms (Prince, J. A., et al. 2001).

In some embodiments, multiplex-allele-specific diagnostic assays (MASDA) can be used for the analysis of a large number of samples (>500). MASDA utilizes oligonucleotide hybridization to interrogate DNA sequences. Multiplex DNA samples are immobilized on a solid support and a single hybridization is performed with a pool of allele-specific oligonucleotides (ASO) probes. Any probes complementary to specific polymorphisms present in a given sample are in effect affinity purified from the pool by the target DNA. Sequence-specific band patterns (fingerprints), generated by chemical or enzymatic sequencing of the bound ASO(s), easily identify the specific mutation(s).

There are several alternative hybridization-based techniques, including, among others, molecular beacons, and Scorpion® probes (Tyagi, S. and Kramer, F. R. 1996; Thelwell et al., 2000). Molecular beacons are comprised of oligonucleotides that have fluorescent reporter and quencher dyes at their 5' and 3' ends. The central portion of the oligonucleotide hybridizes across the target sequence, but the 5' and 3' flanking regions are complementary to each other. When not hybridized to their target sequence, the 5' and 3' flanking regions hybridize to form a stem-loop structure, and there is little fluorescence because of the proximity of the reporter and quencher dyes. However, upon hybridization to their target sequence, the dyes are separated and there is a large increase in fluorescence. Mismatched probe-target hybrids dissociate at substantially lower temperature than exactly complementary hybrids. There are a number of variations of the "beacon" approach. Scorpion® probes are similar but incorporate a PCR primer sequence as part of the probe. A more recent "duplex" format has also been developed.

In some embodiments, a further method of identifying a SNP comprises the SNP-IT™ method (Orchid BioSciences, Inc., Princeton, N.J.). In general, SNP-IT™ is a 3-step primer extension reaction. In the first step a target polynucleotide is isolated from a sample by hybridization to a capture primer, which provides a first level of specificity. In a second step, the capture primer is extended from a terminating nucleotide triphosphate at the target SNP site, which provides a second level of specificity. In a third step, the extended nucleotide triphosphate can be detected using a variety of known formats, including: direct fluorescence, indirect fluorescence, an indirect colorimetric assay, mass spectrometry, fluorescence polarization, etc. Reactions can be processed in 384-well format in an automated format using a SNPstream™ instrument (Orchid BioSciences, Inc., Princeton, N.J.).

In these embodiments, the amplification products can be detected by Southern Blot analysis with or without using radioactive probes. In one such method, for example, a small sample of DNA containing a very low level of the nucleic acid sequence of the polymorphic locus is amplified, and analyzed via a Southern Blotting technique or similarly, using a dot blot analysis. The use of non-radioactive probes or labels is facilitated by the high level of the amplified signal. Alternatively, probes used to detect the amplified products can be directly or indirectly detectably labelled, for example, with a radioisotope, a fluorescent compound, a bioluminescent compound, a chemiluminescent compound, a metal chelator or an enzyme.

Hybridization conditions, such as salt concentration and temperature can also be adjusted for the nucleotide sequence to be screened. Southern blotting and hybridization protocols are described in Current Protocols in Molecular Biology (Greene Publishing Associates and Wiley-Interscience), pages 2.9.1-2.9.10. Probes can be labelled for hybridization with random oligomers and the Klenow fragment of DNA polymerase. Very high specific activity probes can be obtained using commercially available kits such as the Ready-To-Go DNA Labeling Beads (Pharmacia Biotech), following the manufacturer's protocol. Possible competition probes having high repeat sequence content, and stringency of hybridization and wash down will be determined individually for each probe used. Alternatively, fragments of a candidate sequence may be generated by PCR, the specificity may be verified using a rodent-human somatic cell hybrid panel, and sub-cloning the fragment. This allows for a large prep for sequencing and use as a probe. Once a given gene fragment has been characterized, small probe preparations can be achieved by gel or column purifying the PCR product.

Suitable materials that cane be used in the dot blot, reverse dot blot, multiplex and MASDA formats are well known in the art and include, but are not limited to nylon and nitrocellulose membranes.

3.3 Polymorphism Scanning Techniques

Scanning techniques contemplated by the present invention for detecting polymorphisms within a nucleotide sequence can include, but are not restricted to, chemical mismatch cleavage (CMC) (Saleeba, J. A et al., 1992), mismatch repair enzymes cleavage (MREC) (Lu, A. L. and Hsu, I. C, 1992), chemical cleavage techniques, denaturing gradient gel electrophoresis (DGGE) (Wartell et al., 1990; Sheffield et al., 1989), temperature gradient gel electrophoresis (TGGE) (Salimullah, et al. 2005), constant denaturant gel electrophoresis (CDGE), single strand conformation polymorphism (SSCP) analysis (Kumar, D. et al., 2006), heteroduplex analysis (HA) (Nagamine, C. M., et al., 1989), microsatellite marker analysis and single strand polymorphism assays (SSPA).

In some embodiments, the SNPs of the present invention are detected through CMC, wherein a radiolabeled DNA wild type sequence (i.e., probe) is hybridized to an amplified sequence containing the putative alteration to form a heteroduplex. A chemical modification, followed by piperidine cleavage, is used to remove the mismatch bubble in the heteroduplex. Gel electrophoresis of the denatured heteroduplex and autoradiography allow visualisation of the cleavage product. Osmium tetroxide is used for the modification of mispaired thymidines and hydroxylamine for mismatched cytosines. Additionally, labeling the antisense strand of the probe DNA allows the detection of adenosine and guanosine mismatches. The chemical cleavage of mismatch can be used to detect almost 100% of mutations in long DNA fragments. Moreover, this method provides the precise characterization and the exact location of the mutation within the tested fragment. Recently, the method has been amended to make CMC more suitable for automation by using fluorescent primers also enabling multiplexing and thereby reducing the number of manipulations. Alternatively, fluorescently labeled dUTPs incorporated via PCR allow the internal labelling of both target and probe DNA strands and therefore labelling of each possible hybrid, doubling the chances of mutation detection and virtually guaranteeing 100% detection.

In other embodiments, the mismatch repair enzymes cleavage (MREC) assay is used to identify SNPs of the present invention. MREC relies on nicking enzyme systems specific for mismatch-containing DNA. The sequence of interest is amplified by PCR and homo- and heteroduplex species may be generated at the end of the PCR, by denaturing and allowing to re-anneal the amplified products. These hybrids are treated with mismatch repair enzymes and then analysed by denaturing gel electrophoresis. The MREC assay makes use of three mismatch repair enzymes. The MutY endonuclease removes adenines from the mismatches and is useful to detect both A/T and C/G transversions and G/C and T/A transitions. Mammalian thymine glycosylase removes thymines from T/G, T/C and T/T mismatches and is useful to detect G/C and A/T transitions as well as A/T and G/C and T/A and A/T transversions. The all-type endonuclease or topoisomerase I from human or calf thymus can recognize all eight mismatches and can be used to scan any nucleotide substitution. MREC can use specific labels which can be incorporated into both DNA strands, thus allowing all four possible nucleotide substitutions in a given site to be identified.

In some embodiments, chemical cleavage analysis as described in U.S. Pat. No. 5,217,863 is used for identifying SNPs within nucleotide sequences. Like heteroduplex analysis, chemical cleavage detects different properties that result when mismatched allelic sequences hybridize with each other. Instead of detecting this difference as an altered migration rate on a gel, the difference is detected in altered susceptibility of the hybrid to chemical cleavage using, for example, hydroxylamine, or osmium tetroxide, followed by piperidine.

Among the cleavage methods contemplated by the present invention, RNAse A relies on the principle of heteroduplex mismatch analysis. In the RNAse A cleavage method, RNA-DNA heteroduplex between radiolabeled riboprobe and a DNA, obtained by PCR amplification, is enzymatically cleaved by RNAse A, by exploiting the ability of RNAse A to cleave single-stranded RNA at the points of mismatches in RNA:DNA hybrids. This is followed by electrophoresis and autoradiography. The presence and location of a mutation are indicated by a cleavage product of a given size (Meyers, R. M., et al., 1985; Gibbs, R. A. and Caskey, T., 1987).

DNA probes also can be used to detect mismatches, through enzymatic or chemical cleavage; see, e.g., Cotton, et al., 1988; Shenk et al., 1975; and Novack et al., 1986.

In some embodiments, the Invader® assay (Third Wave™ Technology) may be employed to scan for polymorphisms within the 16S rRNA genes of the present invention. For example, the Invader® assay is based on the specificity of recognition, and cleavage, by a Flap endonuclease, of the three dimensional structure formed when two overlapping oligonucleotides hybridize perfectly to a target DNA (Lyamichev, V. et al., 1999).

Alternatively, denaturing gradient gel electrophoresis (DGGE) is a useful technique to separate and identify sequence variants. DGGE is typically performed in constant-concentration polyacrylamide gel slabs, cast in the presence of linearly increasing amounts of a denaturing agent (usually formamide and urea, cathode to anode). A variant of DGGE employs temperature gradients along the migration path and is known as TGGE. Separation by DGGE or TGGE is based on the fact that the electrophoretic mobility in a gel of a partially melted DNA molecule is greatly reduced as compared to an unmelted molecule.

In some embodiments, constant denaturant gel electrophoresis (CDGE) is useful for detecting SNPs within a nucleotide sequence, as described in detail in Smith-Sorenson et al., 1993. A given DNA duplex melts in a predetermined, characteristic fashion in a gel of a constant denaturant. Mutations alter this movement. An abnormally migrating fragment is isolated and sequenced to determine the specific mutation.

In other embodiments, single-strand conformation polymorphism (SSCP) analysis provides a method for detecting SNPs of the present invention. SSCP is a method based on a change in mobility of separated single-strand DNA molecules in non-denaturing polyacrylamide gel electrophoresis. Electrophoretic mobility depends on both size and shape of a molecule, and single-stranded DNA molecules fold back on themselves and generate secondary structures, which are determined by intra-molecular interactions in a sequence dependent manner. A single nucleotide substitution can alter the secondary structure and, consequently, the electrophoretic mobility of the single strands, resulting in band shifts on autoradiographs. The ability of a given nucleotide variation to alter the conformation of the single strands is not predictable on the basis of an adequate theoretical model and base changes occurring in a loop or in a long stable stem of the secondary structure might not be detected by SSCP. Standard SSCP reaches maximal reliability in detecting sequence alterations in fragments of 150-200 bp. More advanced protocols, allowing the detection of mutations at sensitivity equal to that of the radioactively-based SSCP analysis, have been developed. These methods use fluorescence-labeled primers in the PCR and analyze the products with a fluorescence-based automated sequencing machine. Multi-colour fluorescent SSCP also allows including an internal standard in every lane, which can be used to compare data from each lane with respect to each other. Other variants to increase the detection rate include a dideoxy sequencing approach based on dideoxy fingerprinting (ddF) and restriction endonuclease fingerprinting (REF).

The ddF method is a combination of SSCP and Sanger dideoxy sequencing, which involves non-denaturing gel electrophoresis of a Sanger sequencing reaction with one dideoxynucleotide. In this way, for example, a 250-bp fragment can be screened to identify a SNP. REF is a more complex modification of SSCP allowing the screening of more than 1 kb fragments. For REF, a target sequence is amplified with PCR, digested independently with five to six different restriction endonucleases and analyzed by SSCP on a non-denaturing gel. In the case of six restriction enzymes being used, a sequence variation will be present in six different restriction fragments, thus generating 12 different single-stranded segments. A mobility shift in any one of these fragments is sufficient to pinpoint the presence of a SNP of the invention. The restriction pattern obtained enables localization of an alteration in the region examined.

In some embodiments, heteroduplex analysis (HA) detects single base substitutions in PCR products or nucleotide sequences. HA can be rapidly performed without radioisotopes or specialized equipment. The HA method takes advantage of the formation of heteroduplexes between sequences with differing nucleotides at one or more positions by heating and renaturing of PCR products. Due to a more open double-stranded configuration surrounding the mismatched bases, heteroduplexes migrate slower than their corresponding homoduplexes, and are then detected as bands of reduced mobility. The ability of a particular single base substitution to be detected by the HA method cannot be predicted merely by knowing the mismatched bases since the adjacent nucleotides have a substantial effect on the configuration of the mismatched region and length-based separation will clearly miss nucleotide substitutions. Optimization of the temperature, gel cross-linking and concentration of acrylamide used as well as glycerol and sucrose enhance the resolution of mutated samples. The HA method can be rapidly performed without radioisotopes or specialized equipment and screens large numbers of samples for known mutations and polymorphisms in sequenced genes. When HA is used in combination with SSCP, up to 100% of all alterations in a DNA fragment can be easily detected.

In some embodiments, the use of proteins that recognize nucleotide mismatches, such as the *E. coli* mutS protein can be used to detect a polymorphism within 16S rRNA of the present invention (Modrich 1991). In the mutS assay, the protein binds only to sequences that contain a nucleotide mismatch in a heteroduplex between two sequences.

In further embodiments, polymorphism detection can be performed using microsatellite marker analysis. Microsatellite markers with average genome spacing, for example of about 10 centimorgans (cM), can be employed using standard DNA isolation methods known in the art.

SSPA analysis and the closely related heteroduplex analysis methods described above may be used for screening for single-base polymorphisms (Orita, M. et al., 1989).

3.4 Nucleotide Arrays and Gene Chips for Polymorphism Analysis

The invention further contemplates methods of identifying SNPs through the use of an array of oligonucleotides, wherein discrete positions on the array are complementary to one or more of the sequences containing the SNPs of the present invention, e.g. oligonucleotides of at least 12 nt, at least about 15 nt, at least about 18 nt, at least about 20 nt, or at least about 25 nt, or longer, and including the sequence flanking the polymorphic position. Such an array may comprise a series of oligonucleotides, each of which can specifically hybridize to a different polymorphism. For examples of arrays, see Hacia et al., 1996 and De Risi et al., 1996.

A nucleotide array can include all or a subset of the polymorphisms of the invention, as required. One or more polymorphic forms may be present in the array. The oligonucleotide sequence on the array is generally at least about 12 nt in length, at least about 15 nt, at least about 18 nt, at least about 20 nt, or at least about 25 nt, or more, such as 100 to 200 nt in length. For examples of arrays, see Ramsay 1998; Hacia et al., 1996; Lockhart et al., 1996; and De Risi et al., 1996.

A number of methods are available for creating microarrays of biological samples, such as arrays of DNA samples to be used in DNA hybridization assays. Examples of such arrays are discussed in detail in PCT Application No. WO95/35505; U.S. Pat. No. 5,445,934; and Drmanac et al., 1993. Yershov et al. 1996 describes an alternative construction of an oligonucleotide array. The construction and use of oligonucleotide arrays are reviewed by Ramsay (1998).

Methods of using high-density oligonucleotide arrays for identifying polymorphisms within nucleotide sequences are known in the art. For example, Milosavljevic et al., 1996 describe DNA sequence recognition by hybridization to short oligomers (see also, Drmanac et al., 1998; and Drmanac and Drmanac, 1999). The use of arrays for identification of unknown mutations is proposed by Ginot 1997.

Detection of known mutations is described in Hacia et al. 1996; Cronin et al., 1996; and others. The use of arrays in genetic mapping is discussed in Chee et al., 1996; Sapolsky and Lishutz, 1996; and Shoemaker et al., 1996.

Quantitative monitoring of gene expression patterns with a complementary DNA microarray is described in Schena et al., 1995; and DeRisi et al., 1997. Wodicka et al., 1997 performs genome wide expression monitoring in *S. cerevisiae*.

High-density microarrays of oligonucleotides are known in the art and are commercially available. The sequence of oligonucleotides on the array will correspond to a known target sequences. The length of oligonucleotide present on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Methods of producing large arrays of oligonucleotides are described in U.S. Pat. Nos. 5,134,854 and 5,445,934 using light-directed synthesis techniques. Using a computer-controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Publication WO 95/35505.

Microarrays can be scanned to detect hybridization of the labeled genome samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. 1996. A scan, using the appropriate excitation line, is performed for each fluorophore used. The digital images generated from the scan are then combined for subsequent analysis. For any particular array element, the ratio of the fluorescent signal from one nucleic acid sample is compared to the fluorescent signal from the other nucleic acid sample, and the relative signal intensity determined.

Methods for analysing the data collected by fluorescence detection are known in the art. Data analysis includes the steps of determining fluorescent intensity as a function of substrate position from the data collected, removing outliers, i.e., data deviating from a predetermined statistical distribution, and calculating the relative binding affinity of the targets from the remaining data. The resulting data may be displayed as an image with the intensity in each region varying according to the binding affinity between targets and probes.

Nucleic acid analysis via microchip technology is also applicable to the present invention. In this technique, thousands of distinct oligonucleotide probes can be applied in an array on a silicon chip. A nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, or measure expression levels of a gene of interest. The method is one of parallel processing of many, even thousands, of probes at once and can tremendously increase the rate of analysis.

Alteration of mRNA transcription can be detected by any techniques known to persons of ordinary skill in the art. These include Northern blot analysis, PCR amplification and RNase protection. Diminished mRNA transcription indicates an alteration of the sequence.

The array/chip technology has already been applied with success in numerous cases.

For example, the screening of mutations has been undertaken in the BRCA 1 gene, in S. cerevisiae mutant strains, and in the protease gene of HIV-1 virus (Hacia et al., 1996; Shoemaker et al., 1996; Kozal et al., 1996). Chips of various formats for use in detecting SNPs can be produced on a customized basis.

An array-based tiling strategy useful for detecting SNPs is described in EP 785280. Briefly, arrays may generally be "tiled" for a large number of specific polymorphisms. "Tiling" refers to the synthesis of a defined set of oligonucleotide probes that are made up of a sequence complementary to the target sequence of interest, as well as preselected variations of that sequence, e.g., substitution of one or more given positions with one or more members of the basis set of monomers, i.e., nucleotides. Tiling strategies are further described in PCT application No. WO 95/11995. In some embodiments, arrays are tiled for a number of specific SNPs. In particular, the array is tiled to include a number of detection blocks, each detection block being specific for a specific SNP or a set of SNPs. For example, a detection block may be tiled to include a number of probes that span the sequence segment that includes a specific SNP. To ensure probes that are complementary to each allele, the probes are synthesized in pairs differing at the SNP position. In addition to the probes differing at the SNP position, monosubstituted probes are also generally tiled within the detection block. Such methods can readily be applied to the SNP information disclosed herein.

These monosubstituted probes have bases at and up to a certain number of bases in either direction from the polymorphism, substituted with the remaining nucleotides (selected from A, T, G, C and U). Typically, the probes in a tiled detection block will include substitutions of the sequence positions up to and including those that are 5 bases away from the SNP. The monosubstituted probes provide internal controls for the tiled array, to distinguish actual hybridization from artificial cross-hybridization. Upon completion of hybridization with the target sequence and washing of the array, the array is scanned to determine the position on the array to which the target sequence hybridizes. The hybridization data from the scanned array is then analyzed to identify which allele or alleles of the SNP are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length and the sequences complementary thereto, or a fragment thereof, the fragment comprising at least about 8 consecutive nucleotides, preferably 10, 15, 20, more preferably 25, 30, 40, 47, or 50 consecutive nucleotides and containing a polymorphic base. In some embodiments the polymorphic base is within 5, 4, 3, 2, or 1 nucleotides from the centre of the polynucleotide, more preferably at the centre of the polynucleotide. In other embodiments, the chip may comprise an array containing any number of polynucleotides of the present invention.

An oligonucleotide may be synthesized on the surface of the substrate by using a chemical coupling procedure and an ink jet application apparatus, as described in PCT application WO95/251116. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number which lends itself to the efficient use of commercially available instrumentation.

Using such arrays, the present invention provides methods of identifying the SNPs of the present invention in a sample. Such methods comprise incubating a test sample with an array comprising one or more oligonucleotide probes corresponding to at least one SNP position of the present invention, and assaying for binding of a nucleic acid from the test sample with one or more of the oligonucleotide probes. Such assays will typically involve arrays comprising oligonucleotide probes corresponding to many SNP positions and/or allelic variants of those SNP positions, at least one of which is a SNP of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel SNPs disclosed herein. Examples of such assays can be found in Chard, T, An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (I 982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

Multicomponent integrated systems may also be used to analyze SNPs. Such systems miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of micro-channels designed onto a glass, silicon, quartz, or plastic wafer included on a microchip. The movements of the samples are controlled by electric, electro-osmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping SNPs, the microfluidic system may integrate, for example, nucleic acid amplification, mini-sequencing primer extension, capillary electrophoresis, and a detection method such as laser induced fluorescence detection.

In a first step, the DNA samples are amplified, preferably by PCR. Then, the amplification products are subjected to automated mini-sequencing reactions using ddNTPs (specific fluorescence for each ddNTP) and the appropriate oligonucleotide mini-sequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can be, for example, polyacrylamide, polyethylene glycol or dextran. The incorporated ddNTPs in the single nucleotide primer extension products are identified by laser-induced fluorescence detection. This microchip can be used to process at least 96 to 384 samples, or more, in parallel.

3.5 Extension Based Techniques for the Detection of Polymorphisms

Extension based techniques for detecting polymorphisms within a nucleotide sequence can include, but are not restricted to allele-specific amplification, also known as the amplification refractory mutation system (ARMS) as disclosed in European Patent Application Publication No. 0332435 and in Newton et al., 1989, and cloning of polymorphisms (COPS) as contemplated by Gibbs et al. 1989.

The extension-based technique, ARMS, uses allele specific oligonucleotide (ASO) PCR primers for genotyping. In this approach, one of the two oligonucleotide primers used for PCR is designed to bind to the polymorphic site, most commonly with the 3' end of the primer targeting the site. Under carefully controlled conditions (annealing temperature, magnesium concentration etc.), amplification only takes place if the nucleotide at the 3' end of the PCR primer is complementary to the base at the polymorphic site, with a mismatch being "refractory" to amplification.

A variation of the ARMS approach, termed mutagenically separated PCR (MS-PCR), comprises two ARMS primers of different lengths, each specific for different polymorphisms at a site. This method yields PCR products of different lengths for the different polymorphisms.

3.6 Ligation Based Assays for Detecting Polymorphisms

Another typical method of SNP detection encompasses the oligonucleotide ligation assay. A number of approaches make use of DNA ligase, an enzyme that can join two adjacent oligonucleotides hybridized to a DNA template. The specificity of the approach comes from the requirement for a perfect match between the hybridized oligonucleotides and the DNA template at the ligation site. In the oligonucleotide ligation assay (OLA), or ligase chain reaction (LCR) assay the sequence surrounding the mutation site is first amplified, and one strand serves as a template for three ligation probes, two of these are allele specific oligonucleotides (ASO) and the third a common probe. Numerous approaches can be used for the detection of the ligated products. For example, the two ASOs can be differentially labeled with fluorescent or hapten labels and ligated products detected by fluorimetric or colorimetric enzyme-linked immunosorbent assays, respectively. For electrophoresis-based systems, use of mobility modifier tags or variation in probe lengths coupled with fluorescence detection enables the multiplex genotyping of several single nucleotide substitutions in a single tube. When used on arrays, ASOs can be spotted at specific locations or addresses on a chip. PCR amplified DNA can then be added and ligation to labeled oligonucleotides at specific addresses on the array can be measured.

3.7 Signal Generating Polymorphism Detection Assays

In some embodiments, fluorescence resonance energy transfer (FRET) is contemplated as a method to identify a polymorphism within the 16S rRNA gene. FRET occurs due to the interaction between the electronic excited states of two dye molecules. The excitation is transferred from one (the donor) dye molecule to the other (the acceptor) dye molecule without emission of a photon. This is distance-dependent, that is the donor and the acceptor dye must be in close proximity. The hybridization probe system consists of two oligonucleotides labeled with fluorescent dyes. The hybridization probe pair is designed to hybridize to adjacent regions on the target DNA. Each probe is labeled with a different marker dye. Interaction of the two dyes can only occur when both are bound to their target. The donor probe is labeled with fluorophore at the 3' end and the acceptor probe at the 5' end. During PCR, the two different oligonucleotides hybridize to adjacent regions of the target DNA such that the fluorophores, which are coupled to the oligonucleotides, are in close proximity in the hybrid structure. The donor fluorophore (F1) is excited by an external light source, and then passes part of its excitation energy to the adjacent acceptor fluorophore (F2). The excited acceptor fluorophore (F2) emits light at a different wavelength which can then be detected and measured for molecular proximity.

In other embodiments, the MagSNiPer method, based on single base extension, magnetic separation, and chemiluminescence provides a further method for SNP identification in a nucleotide sequence. Single base nucleotide extension reaction is performed with a biotinylated primer whose 3' terminus is contiguous to the SNP site with a tag-labeled ddNTP. Then the primers are captured by magnetic-coated beads with streptavidin, and unincorporated labeled ddNTP is removed by magnetic separation. The magnetic beads are incubated with anti-tag antibody conjugated with alkaline phosphatase. After the removal of excess conjugates by magnetic separation, SNP typing is performed by measuring chemilummescence. The incorporation of labeled ddNTP is monitored by chemilummescence induced by alkaline phosphatase.

In some embodiments, fluorescence polarization provides a method for identifying polymorphisms within a nucleotide sequence. For example, amplified DNA containing a polymorphic is incubated with oligonucleotide primers (designed to hybridize to the DNA template adjacent to the polymorphic site) in the presence of allele-specific dye-labeled dideoxyribonucleoside triphosphates and a commercially available modified Taq DNA polymerase. The primer is extended by the dye-terminator specific for the allele present on the template, increasing approximately 10-fold the molecular weight of the fluorophore. At the end of the reaction, the fluorescence polarization of the two dye-terminators in the reaction mixture is analyzed directly without separation or purification. This homogeneous DNA diagnostic method is shown to be highly sensitive and specific and is suitable for automated genotyping of large number of samples.

In other embodiments, surface enhanced Raman scattering can be used as a method for detecting and identifying single base differences in double stranded DNA fragments (see Chumanov, G 1999). SERS has also been used for single molecule detection (Kneipp, K, 1997). SERS results in strongly increased Raman signals from molecules that have been attached to nanometer sized metallic structures.

Illustrative examples include a genotyping method discussed by Xiao and Kwok 2003 based on a primer extension assay with fluorescence quenching as the detection. The template-directed dye-terminator incorporation with fluorescence quenching detection (FQ-TDI) assay is based on the observation that the intensity of fluorescent dye R110- and R6G-labeled acycloterminators is universally quenched once they are incorporated onto a DNA oligonucleotide primer. By comparing the rate of fluorescence quenching of the two allelic dyes in real time, the frequency of SNPs in DNA samples can be measured. The kinetic FQ-TDI assay is highly accurate and reproducible both in genotyping and in allele frequency estimation.

3.8 High-Resolution Melt Analysis

In particular embodiments, the methods of the present invention utilise high-resolution melting (HRM) analysis for classifying and/or identifying bacterial or bacterium in a sample based on the SNP(s) described herein within the 16S rRNA gene, within the 16S rRNA molecule or within a DNA copy thereof.

HRM is based upon the accurate monitoring of changes in fluorescence as a PCR product (i.e., amplicon) stained with an intercalating fluorescent dye is heated through its melting temperature ($T_m$). In contrast to traditional melting, the information in HRM analysis is contained in the shape of the melting curve, rather than just the calculated $T_m$, so HRM may be considered a form of spectroscopy. HRM analysis is a single step and closed tube method, the amplification and melting can be run as a single protocol on a real-time PCR machine.

In embodiments of the present invention, the methods utilise an amplification primer pair that selectively hybridize to a target polynucleotide containing one or more of the SNPs as described herein. The amplification reaction mixture contains the fluorescent dye, which is incorporated into the resulting amplicon.

The resulting amplicon is then subjected to HRM with incremental increases in temperature (i.e., 0.01-0.5° C.) ranging from about 50° C. to about 95° C. At some point during this process, the melting temperature of the amplicon is reached and the two strands of DNA separate or "melt" apart.

The HRM is monitored in real-time using the fluorescent dye incorporated into the amplicon. The level of fluorescence of the dye is monitored as the temperature increases with the fluorescence reducing as the amount of double stranded DNA reduces. Changes in fluorescence and temperature can be plotted in a graph known as a melt curve.

As a skilled addressee will understand, the $T_m$ of the amplicon at which the two DNA strands separate is predictable, being dependent on the sequence of the nucleotide bases forming the amplicon. Accordingly, it is possible to differentiate between amplicons including an amplicon containing a polymorphism (i.e., a SNP or SNPs) as the melt curves will appear different. Indeed, in some embodiments, it is possible to differentiate between amplicons containing the same polymorphism based on differences in the surrounding DNA sequences.

HRM curves can be discriminated from one another by many different strategies. For example, in many cases, HRM curves can be discriminated on the basis of obvious differences in curve shape and/or on the basis of $T_m$ with a difference of 0.2° C. being regarded as significant. In other cases, a difference graph analysis can be used in which a defined curve is used as a baseline with other normalised curves being plotted in relation to the baseline (see Price, E. P. et al. 2007). In yet other cases, a difference graph-based method can be used involving deriving the 3rd and 97th centiles from the mean±1.96 standard deviations for the fluorescence at every temperature (see Andersson, P. et al., 2009; and Merchant-Patel, S. et al. 2008).

4. Tools, Reagents, Primers, Probes, Kits and Processing Systems

The specification explains how various SNPs can be used as 'tools' for identifying, partially identifying or classifying a bacterium, yeast organism or filamentous fungi, or diagnosing a bacterial, yeast organism or filamentous fungi infection. This SNP finding enables the inventors to develop gene/allele-based and gene product-based probes, tools, reagents, methods and assays for identifying, partially identifying or classifying a bacterium, yeast organism or filamentous fungi, or diagnosing a bacterial, yeast organism or filamentous fungi infection.

One of skill in the art could readily design, produce or manufacture a wide range of gene/allele-based and gene product-based probes, tools, reagents, methods and assays based on the information provided in the specification and especially in Tables 1 to 9 and 11.

Generally speaking, such probes, tools or reagents based on or developed in view of the SNPs outlined in the present specification may, for example, specifically bind, detect, identify, characterise or quantify the gene or part of the gene, the RNA gene product or part of the RNA gene product, or other gene products or parts thereof.

Generally speaking, such probe, tool or reagent can be for detection of a polymorphism for example at the genomic level, or at the transcription level.

Generally speaking, such probe, tool or reagent can also be an antibody or other type of molecule or chemical entity capable of detecting the gene or gene product (such as RNA).

More specifically, probes, tools and reagents may include, but are not limited to, the following:

1. An isolated, purified, synthetic or recombinant form of 16S rRNA, 16S rDNA, 18S rRNA or 18S rDNA, or a fragment thereof, including a fragment containing a SNP of interest—single stranded or double stranded.
2. A non-naturally occurring polynucleotide, recombinant polynucleotide, oligonucleotide or cDNA form of 16S rRNA, 16S rDNA, 18S rRNA or 18S rDNA, or a fragment thereof, including a fragment containing a SNP of interest—single stranded or double stranded.
3. An expression vector, recombinant cell or biological sample comprising the nucleic acid or polynucleotide of 1 or 2.

The probe, tool or reagent can be, but is not limited to, an antibody or other type of molecule or chemical entity capable of detecting the gene or gene product (RNA or polypeptide).

The at least one probe, tool or reagent can be any number or combination of the above, and the number and combination will depend on the desired result to be achieved—eg. detection of a polymorphism at the genomic level (genotyping), at the RNA level.

All the essential materials and reagents required for detecting one or more SNPs in the 16S rRNA gene or 18S rRNA gene according to the invention may be assembled together in a kit. The kits may also optionally include appropriate reagents for detection of labels, positive and negative controls, fluorescent dyes, washing solutions, blotting membranes, microtitre plates, dilution buffers and the like. For example, a nucleic acid-based detection kit for the identification of polymorphisms may include one or more of the following: (i) nucleic acid from a Gram-positive cell and/or Gram-negative cell (which may be used as a positive control); and (ii) a primer and/or probe that specifically hybridizes to at least a portion of the 16S rRNA gene or 18S rRNA gene containing the SNP position(s) to be analysed, and optionally one or more other markers, at or around the suspected SNP site. Also included may be enzymes suitable for amplifying nucleic acids including various polymerases (Reverse Transcriptase, Taq, Sequenase™ DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. The kit can also feature various devices and reagents for performing one of the assays described herein; and/or printed instructions for using the kit to identify the presence of a SNP as defined herein.

In some embodiments, the methods described generally herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to detect the presence of an SNP at a position by detecting the hybridization of a probe to a nucleic acid molecule. A processing system also can be used to determine the Gram status or identity or grouping of a bacterium on the basis of detection of one or more SNPs. In some examples, commands inputted to the processing system by a user may assist the processing system in making these determinations.

In one example, a processing system includes at least one microprocessor, a memory, an input/output device, such as a keyboard and/or display, and an external interface, interconnected via a bus. The external interface can be utilised for connecting the processing system to peripheral devices, such as a communications network, database, or storage devices. The microprocessor can execute instructions in the form of applications software stored in the memory to allow the SNP detection and/or microorganism identification or classification process to be performed, as well as to perform any other required processes, such as communicating with the computer systems. The application software may include one or more software modules, and may be executed in a suitable execution environment, such as an operating system environment, or the like.

4.1 Primers, Probes, Kits and Processing Systems for the 16S rRNA Gene or the 18S rRNA Gene The present invention provides probes and primers that may be used in the methods described herein to determine SNPs at one or more positions of the 16S rRNA gene or 18S rRNA gene so as to classify and/or identify bacteria or bacterium, yeast organism or filamentous fungi in a sample.

The primers and probes of the present invention hybridize to at least a portion of the 16S rRNA gene or the 18S rRNA gene (or 16S rRNA molecules or DNA copies thereof or 18S rRNA molecules or DNA copies thereof) containing the SNP position(s). For example, the primers may hybridize to a sequence flanking one or more SNPs, and the probe may hybridize to a sequence that includes one or more SNPs. It is well within the skill of a skilled artisan to design appropriate primers and probes for use in the methods of the present invention, based on the known sequences of the 16S rRNA gene or the 18S rRNA gene.

Non-limiting examples of primers and probes that are useful for the methods of the present invention, in which SNPs in the 16S rRNA of bacterial species at positions corresponding to positions 273, 378, 412, 440, 488, 647 and/or 653 of the 16S rRNA gene set forth in SEQ ID NO:1 are analysed, include those described in Example 1.

For example, to detect SNPs at position 273 an exemplary forward primer includes CCTCTTGCCATCGGATGTG (SEQ ID NO:16) and exemplary reverse primers include CCAGTGTGGCTGGTCATCCT (SEQ ID NO:17), CGATCCGAAAACCTTCTTCACT (SEQ ID NO:20), CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 378, exemplary forward primers include CCTCTTGCCATCGGATGTG (SEQ ID NO:16), CCTACGGGAGGCAGCAGTAG (SEQ ID NO:18), and GGGAGGCAGCAGTAGGGAAT (SEQ ID NO:19); and exemplary reverse primers include CGATCCGAAAACCTTCTTCACT (SEQ ID NO:20), CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 412, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), and AAGACGGTCTTGCTGTCACTTATAGA (SEQ ID NO:21); and exemplary reverse primers include CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 440, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), and TGATGAAGGTTTTCGGATCGT (SEQ ID NO:25); and exemplary reverse primers include TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 488, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), TGATGAAGGTTTTCGGATCGT (SEQ ID NO:25), and GTTGTAAGAGAAGAACGAGTGTGAGAGT (SEQ ID NO:29); and exemplary reverse primers include CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at positions 647 and/or 653, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), TGATGAAGGTTTTCGGATCGT (SEQ ID NO:25), GTTGTAAGAGAAGAACGAGTGTGAGAGT (SEQ ID NO:29), GCGGTTTGTTAAGTCAGATGTGAA (SEQ ID NO:31), GGTCTGTCAAGTCGGATGTGAA (SEQ ID NO:32), and TCAACCTGGGAACTCATTCGA (SEQ ID NO:33); and exemplary reverse primers include GGAATTCTACCCCCCTCTACGA (SEQ ID NO:34), and GGAATTCTACCCCCCTCTACAAG (SEQ ID NO:35).

Similarly, non-limiting examples of primers and probes that are useful for the methods of the present invention, in which SNPs in the 16S rRNA gene or 16S rRNA of bacterial species at positions corresponding to positions corresponding to positions 746, 764, 771, or 785 of the 16S rRNA gene as set forth in SEQ ID NO:43 (or positions 737, 755, 762, or 776 of the 16S rRNA gene as set forth in SEQ ID NO:1) are analysed, include those described in Table 8.

Similarly, non-limiting examples of primers and probes that are useful for the methods of the present invention, in which SNPs in the 18S rRNA gene or 18S rRNA of bacterial species at positions 343, 371, 388, 416, and 467 of the 18S rRNA gene set forth in SEQ ID NO: 37 are analysed, include those described in Table 9.

5. Applications of the Methods of the Present Invention

The methods of the present invention are useful for classifying and/or identifying bacteria, yeast organism or filamentous fungi in a sample, such as a sample from a subject or an environmental sample such as a soil or water sample or a sample taken from the surface of equipment or instruments (e.g. medical or surgical instruments) or a work surface. Such classification or identification can then be used to determine a course of treatment to remove, eradicate or reduce the number of bacteria, yeast organism or filamentous fungi. Any two or more of the methods of the present invention can be combined. For example, nucleic acid from a sample can be analysed for the presence of SNPs in a 16S rRNA gene using the methods of the present invention. This can be done so as to determine whether Gram-positive bacteria or Gram-negative bacteria are present in the sample. The bacteria can be further grouped or the identity of the bacterium may also be determined or narrowed down to one of a few possibilities. For example, as would be apparent from the disclosure above, SNPs at positions corresponding to positions 273, 378, 412, 440, 488, 647 and 653 of the 16S rRNA gene set forth in SEQ ID NO:1 can be assessed so as to classify or even identify a bacterium in a sample.

Subjects with infections or suspected infections often present to clinicians in clinics, emergency rooms, general wards and intensive care units. Such patients often have non-diagnostic clinical signs of abnormal temperature, increased heart and respiratory rates and abnormal white cells counts. A clinician must decide whether the patient has an infection or not, the severity of the infection, whether to admit the patient to hospital (if not already in hospital), the source of infection, whether to use antibiotics, and if so, the type, route and dose of antibiotics. The presence of an infection in a patient has most typically been assessed by taking a sample from the patient and growing an organism in culture broth. Once an organism has grown it can be Gram stained and identified. However, in many infected patients (>50) it is not possible to culture an organism. Without an identified organism, a clinician must rely on clinical judgment and the use of broad spectrum antibiotics often in combinations. The indiscriminate use of broad-spectrum antibiotics, without knowledge of the pathogenic organism's identity or sensitivity, results in the development of antibiotic resistance, overuse of antibiotics, and potentially toxic side effects in patients. Blood culture is a sensitive method (1-100 cfu/mL) but only when the blood sample taken contains a viable organism, which is not always the case.

Thus, the methods of the present invention are particularly useful in assisting clinicians in determining whether the subject has an infection and if so, an appropriate course of treatment based on the classification of the bacteria, yeast organism or filamentous fungi causing the infection.

Furthermore, the methods of the present invention facilitate discrimination of Gram-positive and Gram-negative organisms within hours of taking a whole blood from a subject. The methods of the present invention also can be performed in a time-efficient manner, so that the results are available to the clinician within hours rather than days. Such attributes allow a clinician to sensitively detect the presence of a bacterium, yeast organism or filamentous fungi and to make an informed decision on treatment (such as the use of antibiotics specific to the Gram status or further grouping or identification of the bacterium). These improvements can result in a reduced number of patients admitted to hospital unnecessarily, sensitive detection of bacteria, yeast organisms and filamentous fungi, severity of infection assessed on load (and other factors), reduced use of broad-spectrum antibiotics/medicines, reduced patient time on broad spectrum antibiotics, reduced toxicity from antibiotics/medicines, reduced development of resistance to medicines (especially antibiotic resistance).

The present invention also extends to diagnosing a bacterial, yeast organism or filamentous fungi infection in a subject, and the management of the infection following a positive diagnosis. The methods described herein that analyse one or more SNPs within a 16S rRNA or 18S rRNA can be used to determine whether a subject has a bacterial, yeast organism or filamentous fungi infection and/or identify the group or species of bacteria, yeast organism or filamentous fungi in the sample. The methods described herein can be further used to classify a bacteria as Gram-positive or Gram-negative.

5.1 Management and Therapy

Based on the results of the methods of the present invention, the subject can be appropriately managed and administered therapy where required. For example, the management of a bacterial infection can include, for example, administration of therapeutic agents such as a therapeutically effective course of antibiotics.

Typically, therapeutic agents will be administered in pharmaceutical (or veterinary if the subject is a non-human subject) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of the infection, and/or the reduction or elimination of the bacteria from the subject. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of the bacterial infection, the practitioner may evaluate severity of infection, and severity of any symptom associated with the infection including, inflammation, blood pressure anomaly, tachycardia, tachypnoea, fever, chills, vomiting, diarrhoea, skin rash, headaches, confusion, muscle aches and seizures. In any event, those of skill in the art may readily determine suitable dosages of the therapeutic agents and suitable treatment regimens without undue experimentation.

The therapeutic agents may be administered in concert with adjunctive (palliative) therapies to increase oxygen supply to major organs, increase blood flow to major organs and/or to reduce the inflammatory response. Illustrative examples of such adjunctive therapies include non steroidal-anti inflammatory drugs (NSAIDs), intravenous saline and oxygen.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The disclosure of every patent, patent application and publication cited herein is hereby incorporated herein by reference in its entirety.

In order that the invention may be readily understood and put into practical effect, particular preferred embodiments will now be described by way of the following non-limiting examples.

EXAMPLES

Example 1

The aim of this experiment was to differentiate 15 of the most prevalent bacterial species frequently isolated from patients diagnosed with sepsis using the 16S rRNA SNP-HRM assay of the present invention.

Experimental Procedures

In total, the following 15 bacterial species were tested: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes*.

The bacterial species were cultured in Brain Heart Infusion broth overnight at 37° C. whereafter genomic DNA was extracted from each isolate using QIAgen DNeasy Blood and Tissue Kit (Qiagen, Australia).

16S rDNA-SNP primers (of SEQ ID NOs:16-35, made by Sigma Aldrich, Australia) were designed to amplify the regions encompassing the seven SNPs designated as follows: SNP273, SNP378, SNP412, SNP440, SNP488, SNP647 and SNP653 of the 16S rRNA gene as set forth in SEQ ID NO:1. PCR product sizes ranged from 79 bp to 96 bp.

Real-Time PCR followed by HRM analysis was used to differentiate the 15 bacterial species. The Real-Time PCR HRM process was: 1 µl of extracted DNA (1-3 ng) was added to 19 µl of reaction mastermix containing 10 µl of the 2×SYBR green PCR Mastermix (Invitrogen, Australia) and 8 pmol of each primer. Temperature cycling for these reactions were as follows: 50° C. for 2 min, 95° C. for 2 min, followed by 40 cycles of 95° C. for 15 s, 52° C. for 20 s, and 72° C. for 35 s, hold at 72° C. for 2 min, hold at 50° C. for 20 s, HRM: ramp from 65° C. to 95° C. rising by 0.05° C. (Rotor-Gene 6000, Qiagen, Australia).

The Rotor-Gene 6000 software (version 1.7.34 or 1.7.87) was used to analyse the HRM data in multiple ways. A normalised raw melt curve depicts decreasing fluorescence versus increasing temperature, and the difference curve, which displays a user-defined curve as the baseline (i.e., the x-axis), and depicts other normalised curves in relation to that baseline. Criteria for calling melting curves as "same" or "different" using difference graphs have been developed and published previously by the inventor and her co-workers (see, e.g., Stephens, A. J., et al. 2008; Merchant-Patel, S., et al. 2010).

There are two ways that HRM curve plots can discriminate between samples. The shape of the melt curve indicates the details in the shape of the curve, and the curve shift indicates a thermal (temperature) offset of a curve from other curves.

The software allows HRM melt curve analysis using either as normalised melt curves or as difference curves as generally described above. Normalisation curve analysis allows all the HRM curves to be compared with the same starting and ending fluorescent signal level to aid interpretation and analysis. The difference curve analysis displays differences between the melt curves of each sample and a given control.

In this experiment, both the shape and shift approach was used to discriminate the HRM curves for each bacterial species tested. For determining the shift in the melting temperature for each respective bacterial species, a melting temperature difference of 0.2° C. was regarded as a significant difference between each bacterial species' melt curves.

For determining the shape differences between bacterial species, the difference curve analysis was used. An amplitude difference of >5 normalised fluorescence units is indicative that different bacterial species melt curves are different to the comparator species. Hence these differences in the shape of the curve indicate differences in the DNA sequences of each respective bacterial species.

Results

FIGS. 2 to 11 depict normalised and difference melting curves plots used to differentiate the 15 bacterial species tested in this example.

Figure 2:
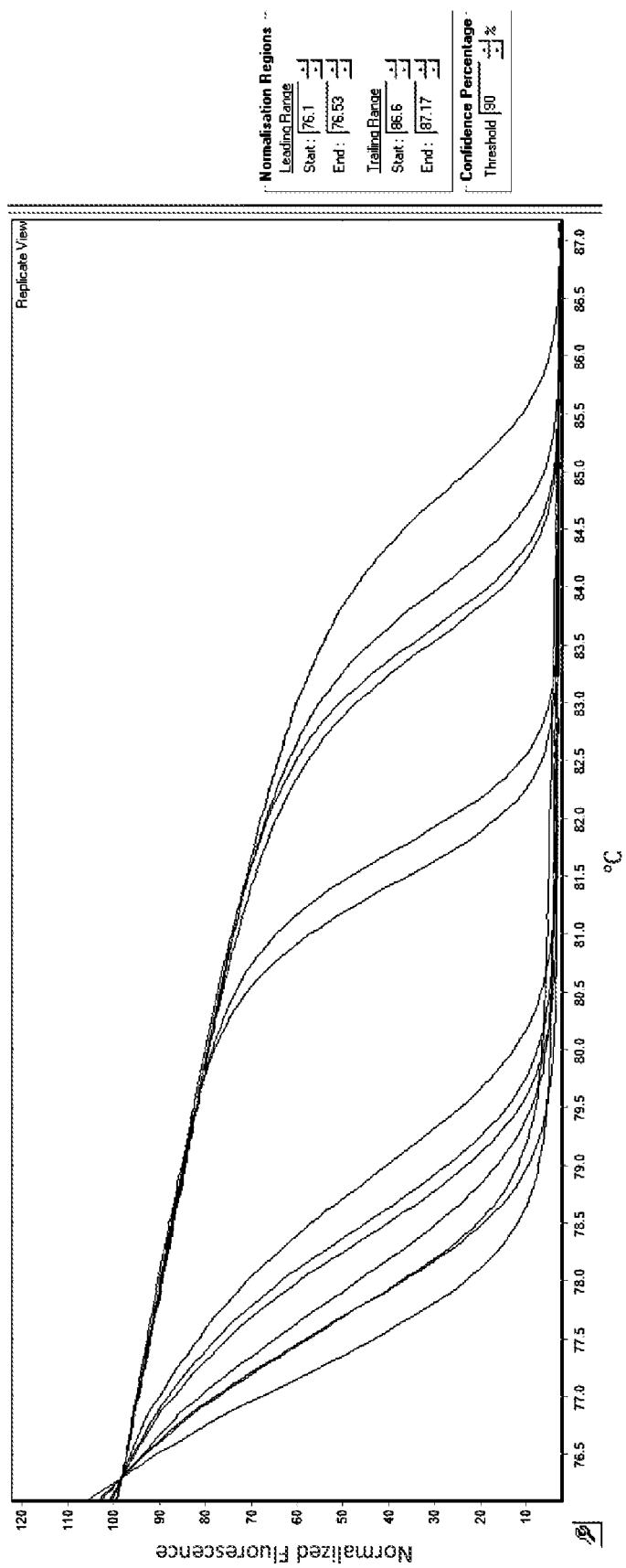
FIG. 2 shows a normalised high-resolution melt (HRM) curves plot for the following 15 bacterial species tested in Example 1: *Acinetobacter calcoaceticus*; *Enterobacter aerogenes*; *Enterobacter cloacae*; *Enterococcus faecalis*; *Enterococcus faecium*; *Escherichia coli*; *Klebsiella pneumoniae*; *Proteus mirabilis*; *Pseudomonas aeruginosa*; *Serratia marcescens*; *Staphylococcus aureus*; *Staphylococcus epidermidis*; *Streptococcus agalactiae*; *Streptococcus pneumoniae*; and *Streptococcus pyogenes*.
Figure 3:
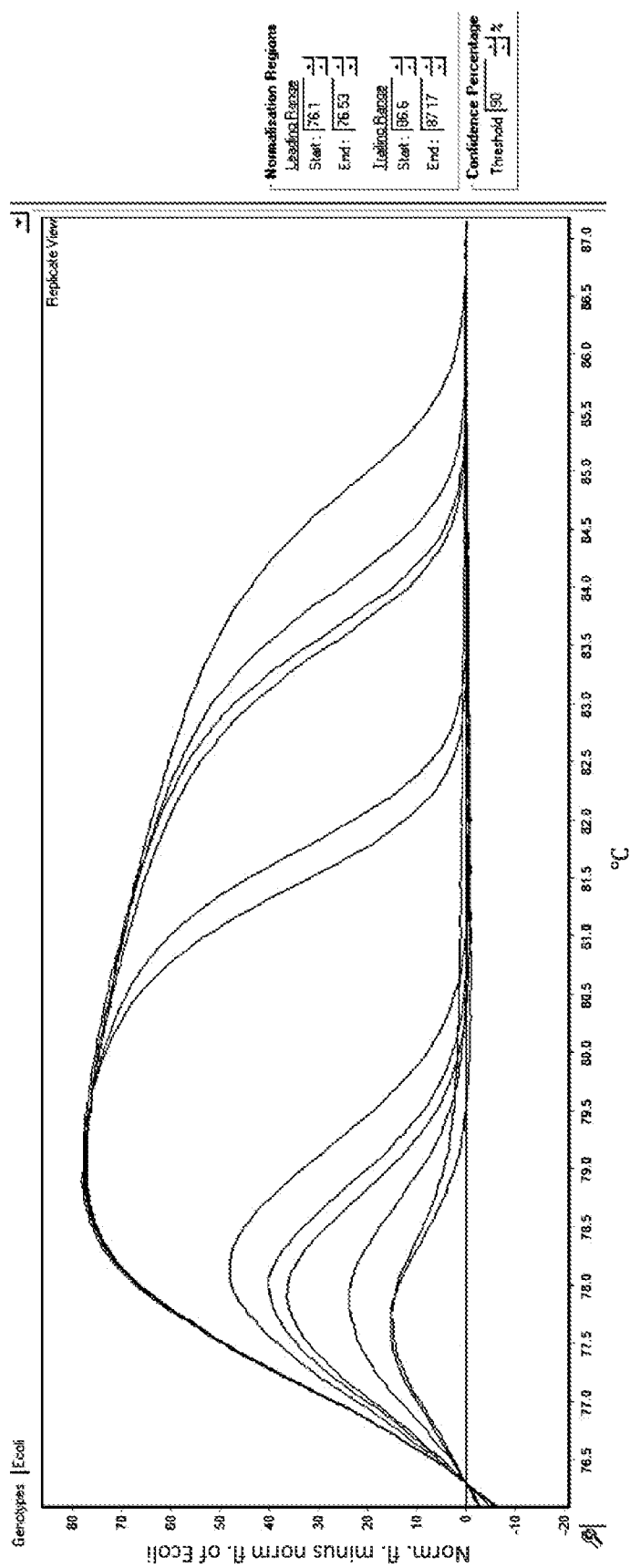
FIG. 3 shows a difference HRM curves plot for the 15 bacterial species shown in FIG. 2 with *Escherichia coli* used as a baseline.
Figure 4:
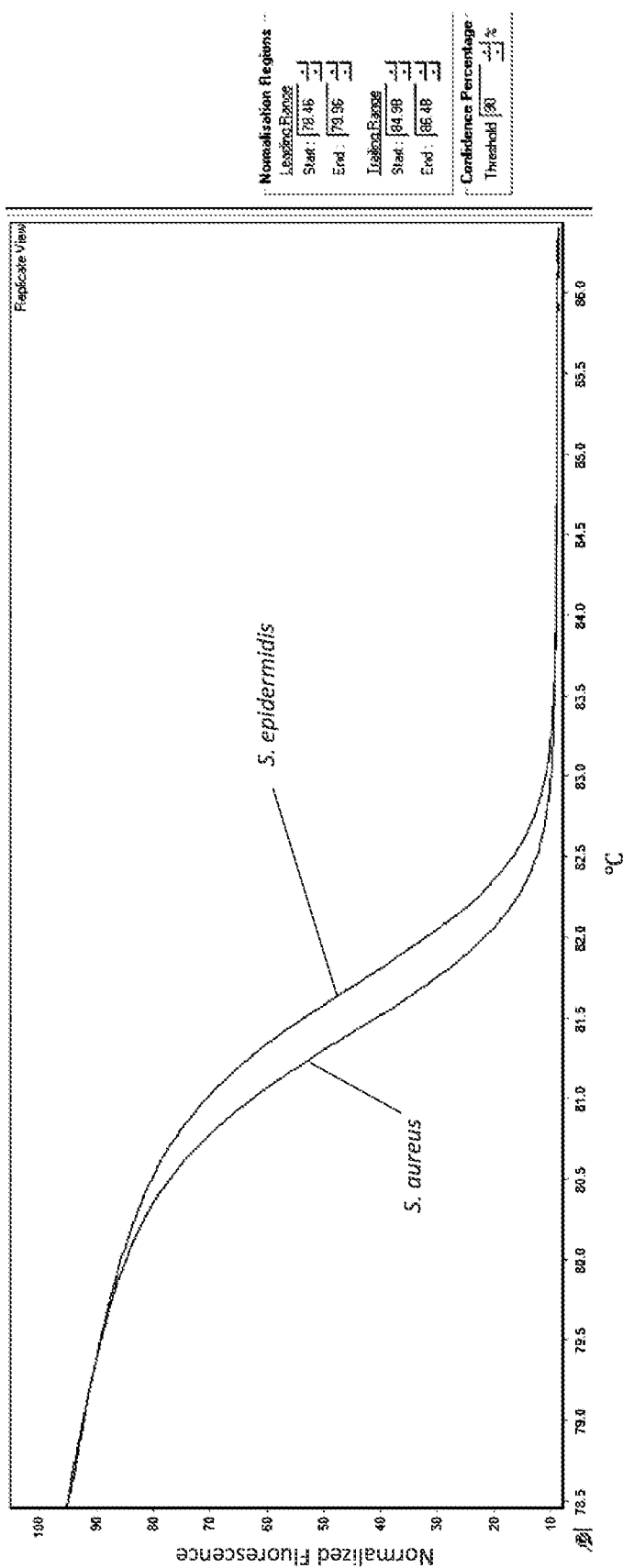
FIG. 4 shows a normalised HRM curves plot for *Staphylococcus aureus* and *Staphylococcus epidermidis* for amplicons containing a SNP at a position corresponding to position 412 in the 16S rRNA gene as set forth in SEQ ID NO:1.
Figure 5:
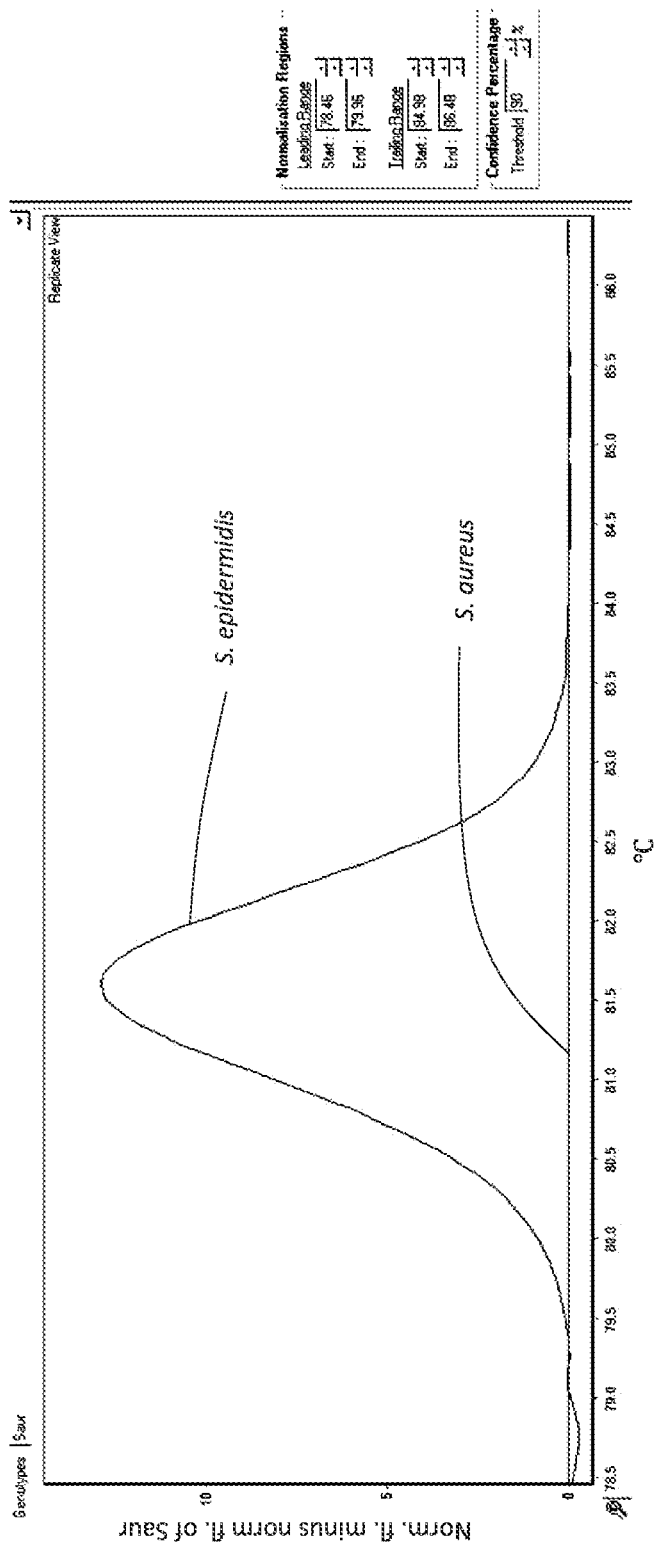
FIG. 5 shows a difference HRM curves plot for *Staphylococcus aureus* and *Staphylococcus epidermidis* as shown in FIG. 4 with *S. aureus* used as the baseline.
Figure 6:
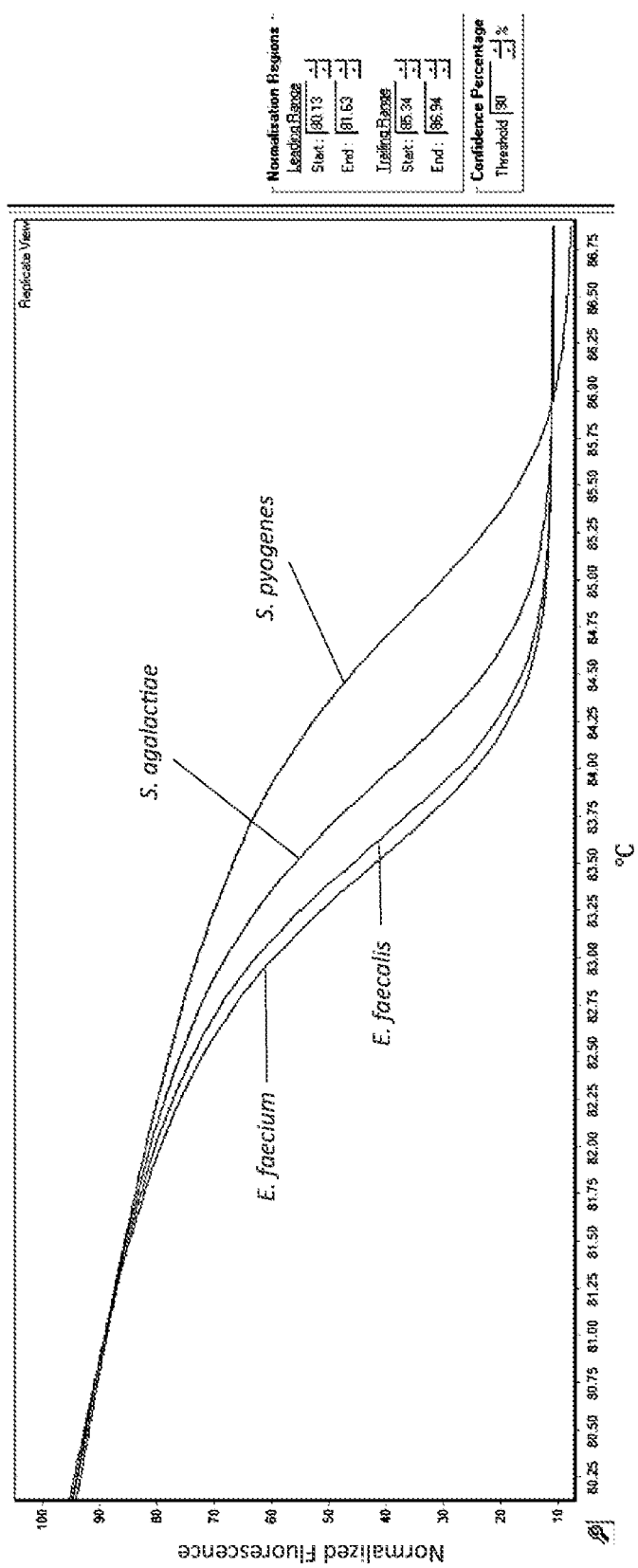
FIG. 6 shows a normalised HRM curves plot for *Enterococcus faecalis*, *Enterococcus faecium*, *Streptococcus agalactiae*; *Streptococcus pneumoniae* and *Streptococcus pyogenes* for amplicons containing a SNP at a position corresponding to position 378 in the 16S rRNA gene as set forth in SEQ ID NO:1.
Figure 7:
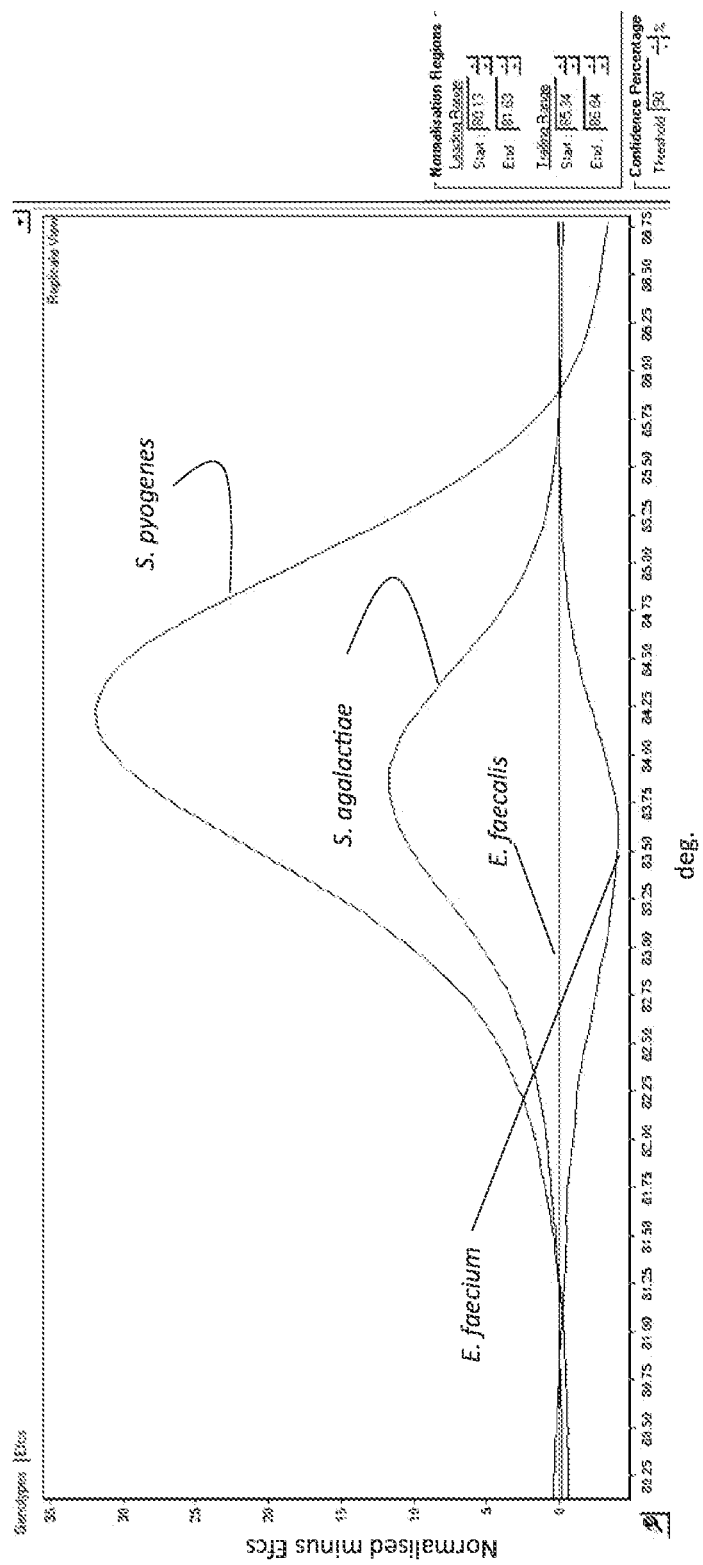
FIG. 7 shows a difference HRM curves plot for *Enterococcus faecalis*, *Enterococcus faecium*, *Streptococcus agalactiae*; *Streptococcus pneumoniae* and *Streptococcus pyogenes* as shown in FIG. 6 with *E. faecalis* used as the baseline.
Figure 8:
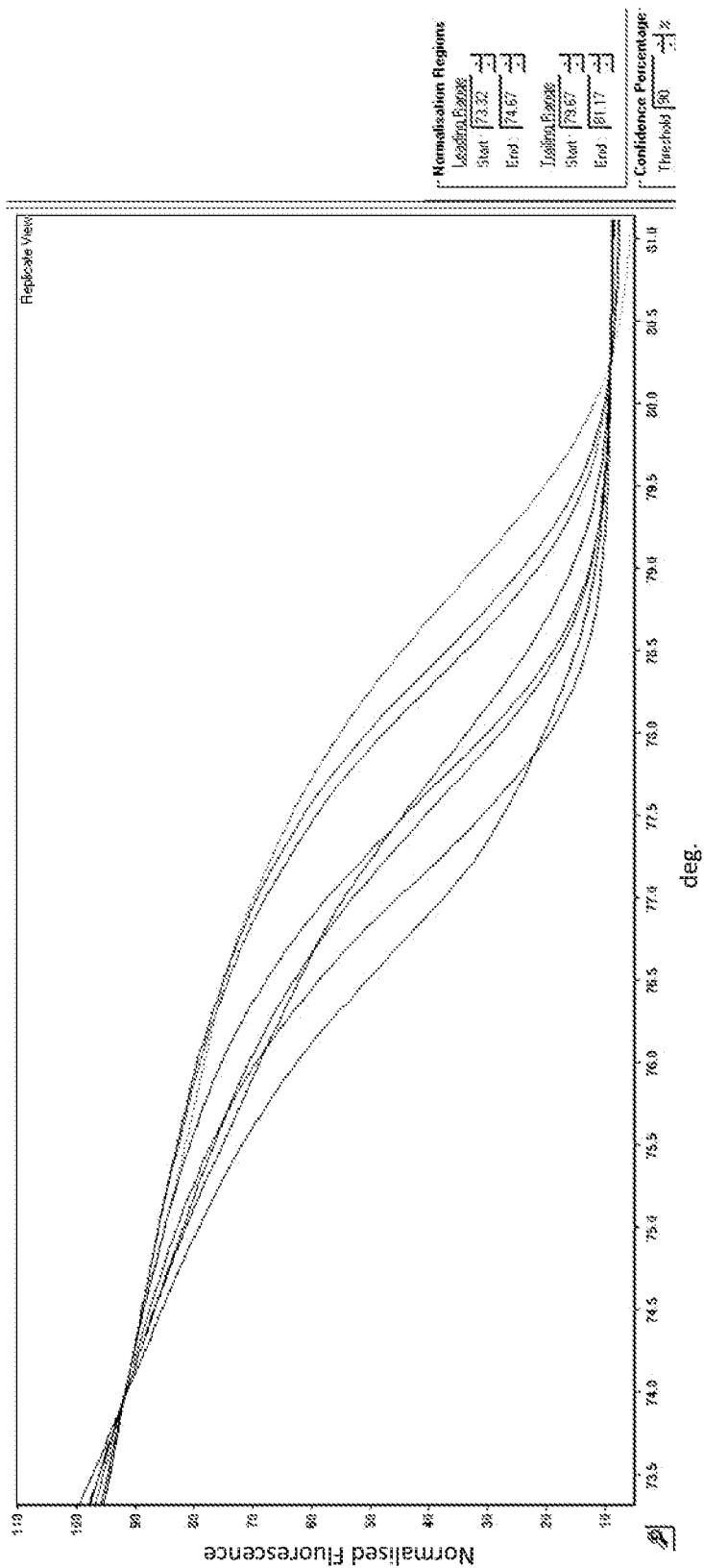
FIG. 8 shows a normalised HRM curves plot for *Escherichia coli, Enterobacter cloacae, Serratia marcescens, Acinetobacter calcoaceticus, Enterobacter aerogenes, Pseudomonas aeruginosa, Klebsiella pneumoniae* and *Proteus mirabilis* for amplicons containing a SNP at a position corresponding to position 412 in the 16S rRNA gene as set forth in SEQ ID NO:1.
Figure 9:
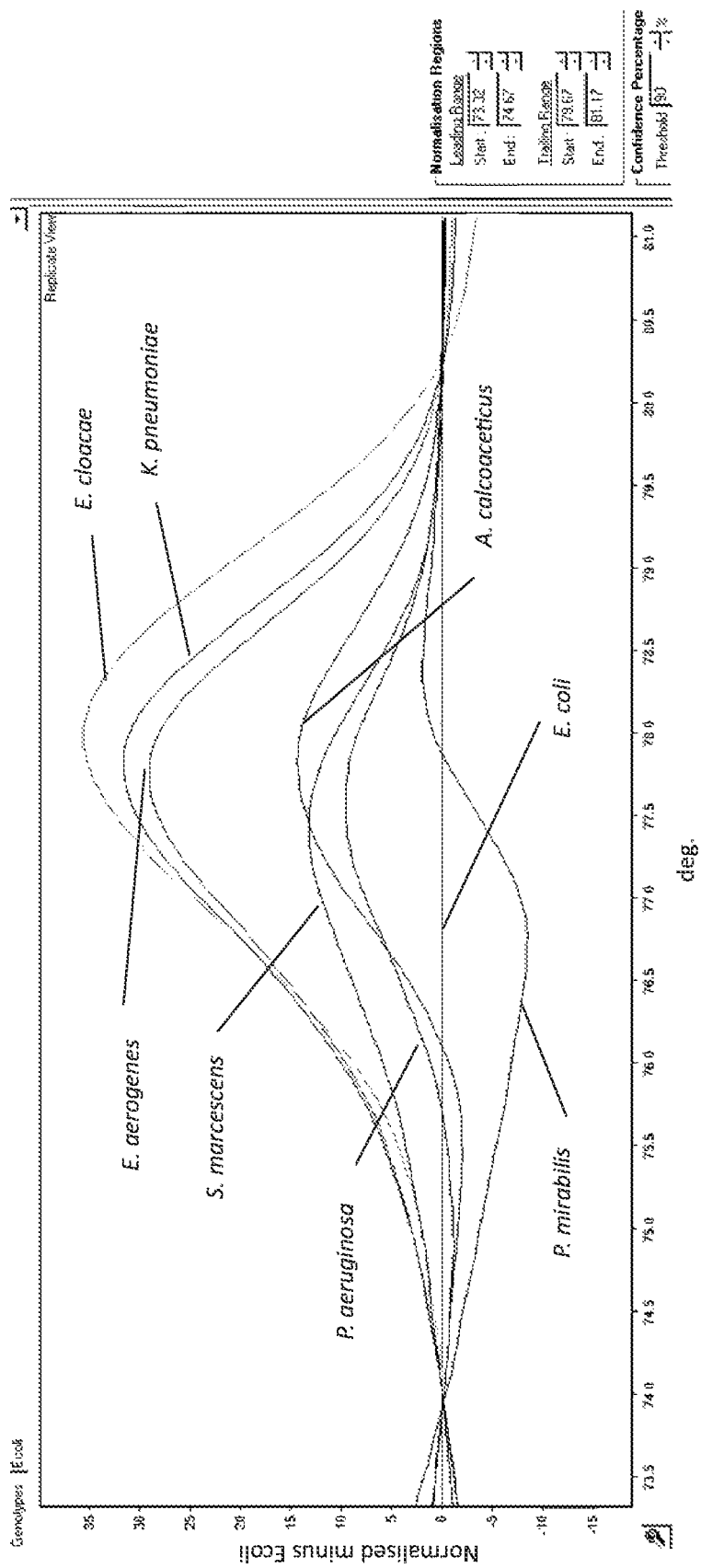
FIG. 9 shows a difference HRM curves plot for *Escherichia coli, Enterobacter cloacae, Serratia marcescens, Acinetobacter calcoaceticus, Enterobacter aerogenes, Pseudomonas aeruginosa, Klebsiella pneumoniae* and *Proteus mirabilis* as shown in FIG. 8 with *Escherichia coli* used as the baseline.
Figure 10:
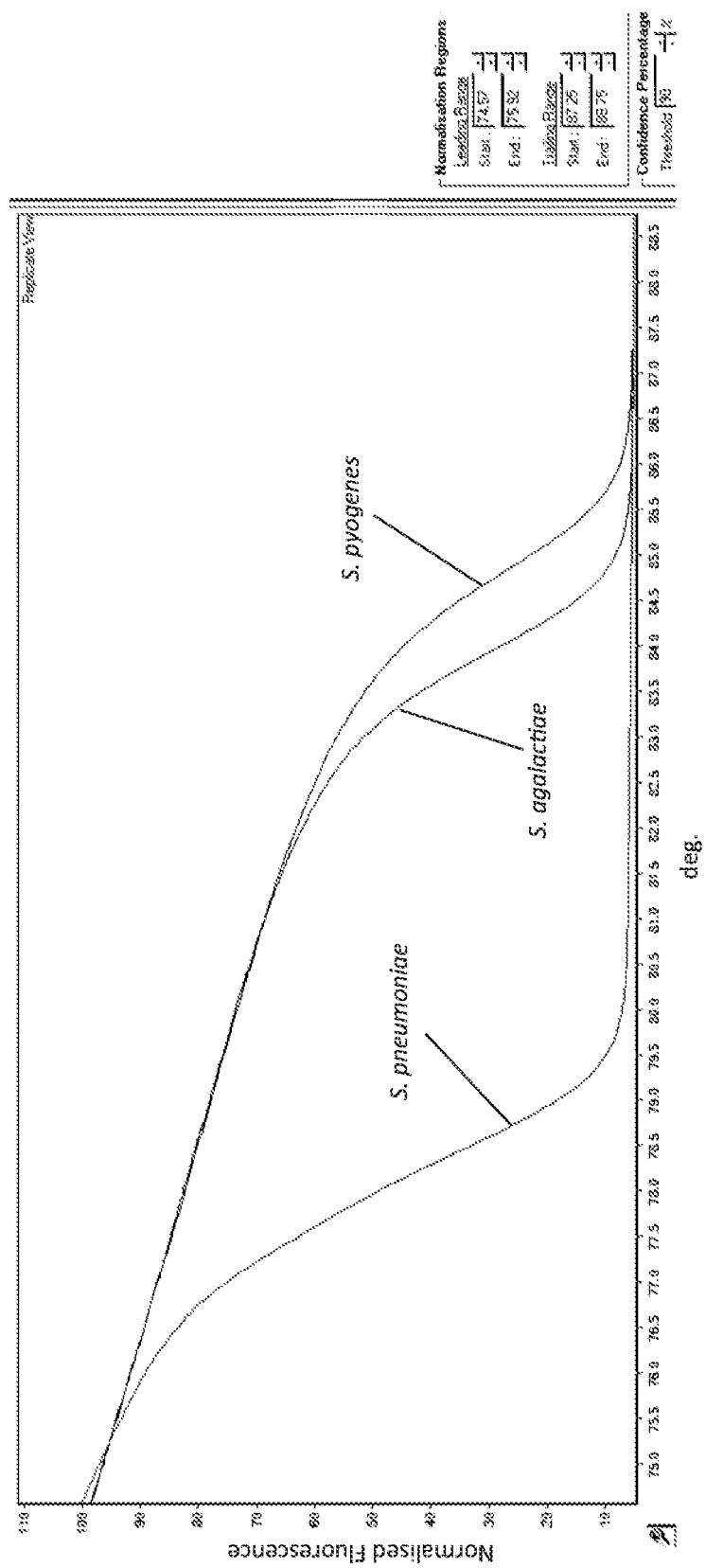
FIG. 10 shows a normalised HRM curves plot for *Streptococcus agalactiae, Streptococcus pneumoniae*, and *Streptococcus pyogenes* for amplicons containing a SNP at a position corresponding to position 378 in the 16S rRNA gene as set forth in SEQ ID NO:1.
Figure 11:
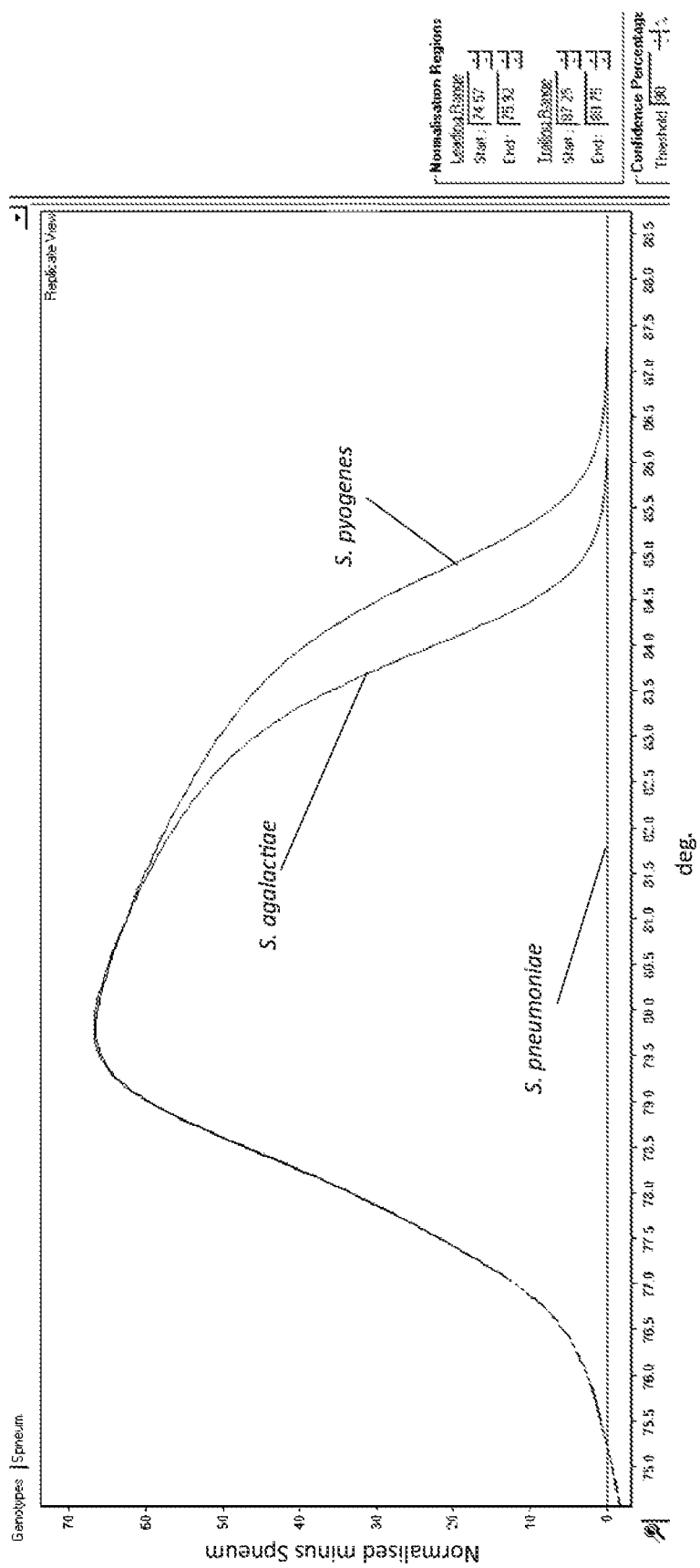
FIG. 11 shows a difference HRM curves plot for *Streptococcus agalactiae, Streptococcus pneumoniae*, and *Streptococcus pyogenes* as shown in FIG. 10 with *Streptococcus pneumoniae* used as the baseline.
Figure 12:
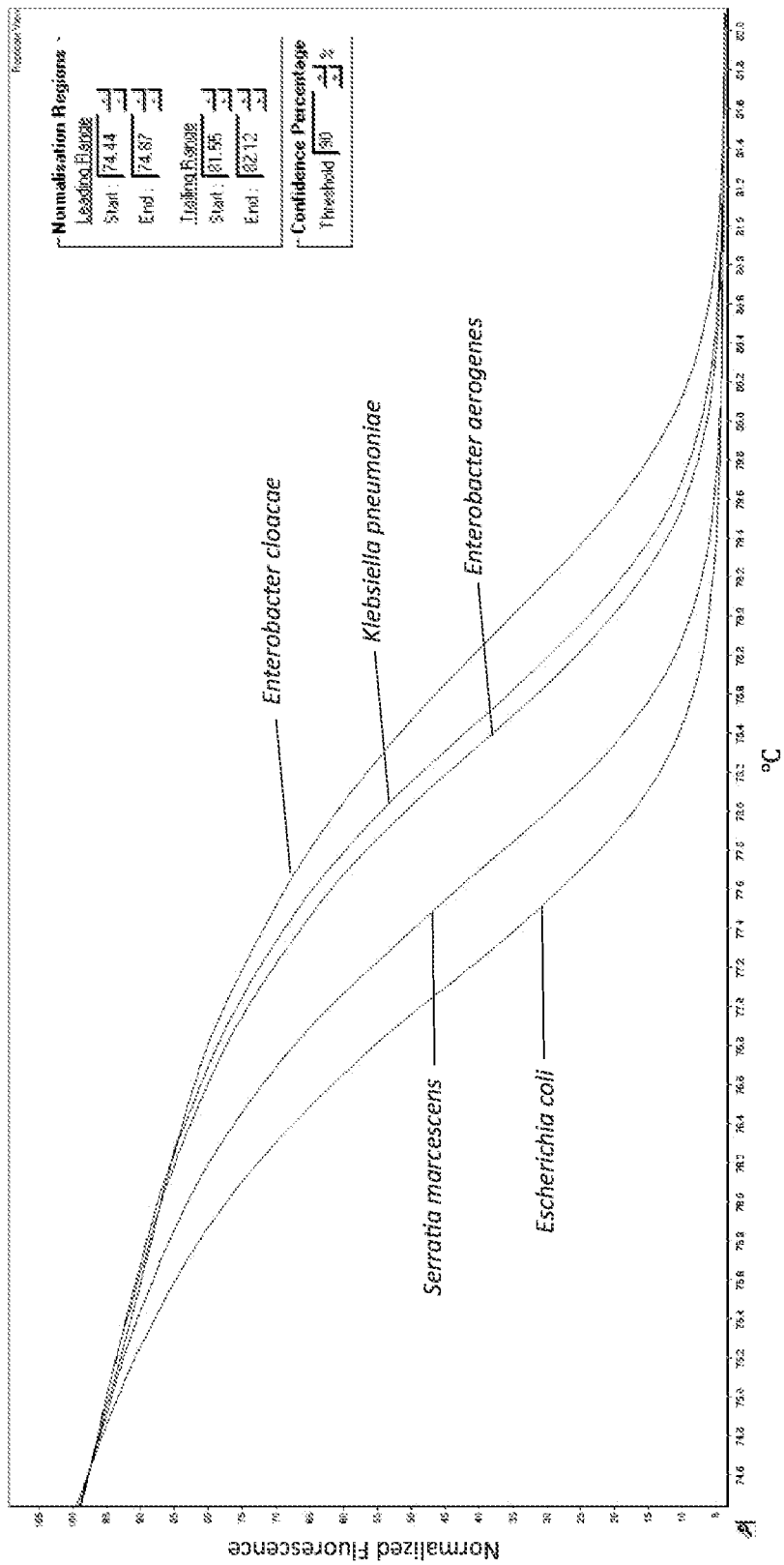
FIG. 12 shows a normalised HRM curves plot for *Escherichia coli, Klebsiella pneumoniae, Enterobacter* aerogenes, Enterobacter cloacae, and Serratia marcescens for amplicons containing a SNP at a position corresponding to position 412 in the 16S rRNA gene as set forth in SEQ ID NO:1.

Each of the 15 bacterial species was designated with species specific genotypes in the HRM analysis setting of the Rotor-Gene 6000 software (version 1.7.34 or 1.7.87). For comparison of the bacterial species difference curves, *Escherichia coli* was used as the "calibrator" or "reference" (indicated as "0" on the Y-axis of the plot shown in FIG. 3. As is shown in FIG. 3, the 14 other bacterial species all showed curves that differ away from the "0" line of *Escherichia coli*. Another example of species differentiation is shown in FIG. 5, where *Staphylococcus aureus* is selected as the "calibrator" or "reference" (at the "0" position on the Y-axis) and as shown *Staphylococcus epidermidis* has a complete separate curve.

The melt curve specificity for the bacteria in urine and plasma is provided in Table 11.

TABLE 11

Bacterial speciation in urine and plasma: Melt curve specificity

| Name | Tm$ | SNP* no. |
|---|---|---|
| E. coli | 77.075 | 1 |
| E. cloacae | 79.050 | 1 |
| S. marcescens | 77.810 | 1 |
| E. aerogenes | 78.250 | 1 |
| K. pneumoniae | 78.435 | 1 |
| E. faecalis | 83.850 | 2 |
| E. faecium | 83.475 | 2 |
| S. agalactiae | 83.925 | 2 |
| S. pyogenes | 84.825 | 2 |
| S. aureus | 81.485 | 3 |
| S. epidermidis | 81.700 | 3 |
| S. pneumoniae | 78.225 | 4 |

$Tm: PCR product melting temperature;
*SNP: Single nucleotide polymorphism.
p-value SNP1vsSNP2: <0.0001;
p-value SNP2vsSNP3: 0.002;
p-value SNP3vsSNP4: 0.0005.

Discussion

This example demonstrates the utility of applying only seven highly discriminating SNPs to differentiate between 15 different bacterial species known to cause life-threatening diseases such as sepsis. The results also indicate that the method of the present invention is highly specific and rapid, both of which are important requirements for a DNA diagnostic assay. This method accurately determines whether two isolates are the same or different based on the DNA melt curves of the PCR products encompassing the highly discriminatory SNPs. The interrogation of these genetic targets means that this approach is especially amenable to adaption to emerging technologies such as "lab-on-chip" devices and dedicated, fully automated real-time PCR machines. Combined with rapidly advancing innovations in microfluidics, the methods of the present invention are suitable for transfer onto devices suitable for "point-of-care" diagnostics.

Example 2

To demonstrate the utility of the present invention, two hundred blood culture positive patient samples were assessed by both standard clinical microbiology and by the methods of the present invention.

The standard clinical microbiology tests were performed by a routine blood culture procedure in the laboratory utilising the BacTAlert system followed by the MALDI biotyper method for bacterial species identification. This involved entering the BacTAlert blood culture bottles into an automated, continuous-monitoring incubation that are incubated for 5-7 days. Once the blood culture bottle is flagged as positive (a minimum of 12 hours incubation), the bottle is removed from the BacTAlert instrument and an aliquot of the growth medium is removed and sub-cultured onto bacterial culture agar plates. The agar plates are incubated at 37° C. for at least 4 hours, or until visible growth appears. Thereafter, a single bacterial colony is placed onto the target plate and a matrix solution is added. The plate is inserted into the biotyper instrument and a MALDI-TOF spectrum is generated by the software. The spectrum is matched against a reference library to provide bacterial identification. The total time for this process is around 16-18 hours. The standard clinical microbiology tests were performed by Pathology Queensland.

The method used according to the present invention was to collect blood culture liquid (1 mL) from 100 blood culture-negative samples after 5 days of incubation on a BacTAlert blood culture machine and stored at 4° C. until extracted. Blood culture liquid (1 mL) was also collected from 200 blood-culture positive samples by staff at the Diagnostic Microbiology Department, Pathology Queensland and stored at 4° C. until DNA was extracted. Microbial DNA was isolated from all samples (blood-culture negative and blood-culture positive) using the MolYsis™ Complete 5 kit (Molzym Life Science, Germany) which enables host DNA removal, pathogen enrichment and DNA extraction from 1 mL of sample.

All 300 DNA extractions were subjected to testing using a real-time PCR format as follows: One microliter of extracted DNA (1 to 3 ng) was added to 19 µl of reaction mastermix containing 10 µl of the 2×SYBR green PCR Mastermix (Life Technologies, Australia) and 8 pmol of each primer. Temperature cycling for these reactions were as follows: 50° C. for 2 min, 95° C. for 2 min, followed by 40 cycles of 95° C. for 15 s, 52° C. for 20 s, and 72° C. for 35 s, Hold at 72° C. for 2 min, Hold at 50° C. for 20 s, HRM: Ramp from 65° C.-95° C. rising by 0.05° C. (RotorGeneQ, Qiagen, Australia). All samples were run in duplicate, including the relevant controls (No Template (NTC) and a positive control consisting of bacterial reference DNA for each bacterial species tested. The time to result was recorded as ±3.5 hrs.

The results were tabulated and were correlated to blood culture microbiology results obtained from Pathology Queensland at the conclusion of the study.

Results

The results of the trial are provided in Table 12.

TABLE 12

Correlation between method of the present invention and clinical microbiology results (Pathology QLD trial). Ten bacterial species were represented in 200 blood culture positive patient samples.

| Bacterial species | Gram status | Clinical microbiology result-samples positive | Method of present invention |
|---|---|---|---|
| Staphylococcus aureus | Positive | 56 | 55 |
| Staphylococcus epidermidis | Positive | 55 | 54 |
| Enterococcus faecalis | Positive | 11 | 11 |
| Escherichia coli | Negative | 50 | 50 |
| Enterobacter cloacae | Negative | 5 | 5 |
| Klebsiella pneumoniae | Negative | 4 | 4 |
| Serratia marcescens | Negative | 6 | 6 |
| Streptococcus agalactiae | Positive | 7 | 6 |
| Streptococcus pyogenes | Positive | 3 | 3 |
| Streptococcus pneumoniae | Positive | 3 | 3 |
| Total | | 200 | 198 (99% specificity) |

Advantageously, the method of the present invention was able to obtain 99% specificity when compared to the clinical microbiology result (however, it is unclear for the two samples where the clinical microbiology and the method of the present invention obtained different results which method produced the incorrect result). The method of the present invention was able to obtain the result within about 3.5 hours and with minimal handling of the patient sample. In contrast, the clinical microbiology result required more significant handling of the patient sample and took about 16-18 hours to obtain.

CITATIONS

1 Anderson & Borreson, 1995, *Diagnostic Molecular Pathology*, 4: 203-211.
2 Andersson, P., et al., 2009, *Antimicrob. Agents Chemother.* 53:2679-2683.
3 Ausubel et al., *Current Protocols in Molecular Biology* (John Wiley & Sons, Inc. 1994-1998.
4 Bullock, G. R. et al., 1985, Techniques in Immunocytochemistry, Academic Press, Orlando, Fla. Vol. 1 (1982), Vol. 2 (1983), Vol. 3 (1985).
5 Chard, T., 1986, An Introduction to Radioimmunoassay and Related Techniques, Elsevier Science Publishers, Amsterdam, The Netherlands (1986)
6 Chee, et al., 1996, *Science* 274: 610-613.
7 Chumanov, G. "Surface Enhanced Raman Scattering (SERS) for Discovering and Scoring Single Based Differences in DNA" Proc. Volume SPIE, 3608 (1999).
8 Cotton, et al., 1988, *Proc. Natl. Acad. Sci. USA*, 85:4397.
9 Cronin, et al., 1996, *Human Mut.* 7: 244-255.
10 De Risi et al, 1996, *Nat. Genet.* 14: 457-460.
11 DeRisi et al., 1997, *Science* 270:680-686.
12 Deveraux et al., 1984, *Nucleic Acids Research* 12, 387-395.
13 Drmanac and Drmanac, 1999, *Methods Enzymol.* 303: 165-178
14 Drmanac et al., 1993, *Science* 260: 1649-1652.
15 Drmanac et al., 1998, *Nature Biotech.* 16: 54-58.
16 Gibbs et al., 1989, *Nucleic Acids Research*, 17: 2347.
17 Gibbs, R. A. and Caskey, T., 1987, *Science*, 236:303-305.
18 Ginot, 1997, *Human Mutation* 10:1-10.
19 Hacia et al., 1996, *Nat. Genet.* 14: 441-447.
20 Jobs et al., 2003, *Genome Res* 13: 916-924.
21 Karlowsky, J. A., et al. (2004) *Ann Clin Microbiol Antimicrob.* 10; 3:7.
22 Kim S. & Misra A. 2007, *Ann Rev Biomed Eng.* 9:289-320.
23 Kneipp, K, 1997, *Physical Review Letters*, 78(9):1667-1670.
24 Komher, J. S. et al., 1989, *Nucl. Acids. Res.* 17: 7779-7784.
25 Kumar, D. et al., 2006, *Genet. Mol. Biol*, 29(2):287-289.
26 Kuppuswamy, M. N. et al., 1991 *Proc. Natl. Acad. Sci.* (U.S.A.) 88:1143-1147.
27 Levy et al., 2003, *Critical Care Medicine*, 31:1250-1256.
28 Liu et al, 1996, *J. Am. Chem. Soc.* 118: 1587-1594.
29 Lockhart et al., 1996, *Nature Biotechnol.* 14:1675-1680.
30 Lu, A. L. and Hsu, I. C., 1992, *Genomics*, 14(2):249-255.
31 Lyamichev, V. et al., 1999, *Nat Biotechnol*, 17: 292-296.
32 Maxam, A. M., et al., 1977, *Proc. Natl. Acad. Sci.* (U.S.A.) 74:560.
33 Merchant-Patel, S., et al., 2008, *Int. J. Food Microbiol.*, 128:304-308.
34 Merchant-Patel, S., Blackall, P. J., Templeton, J., Price, E. P., Tong, S. Y. C., Huygens, F., and Giffard, P. M., 2010, *Applied and Environmental Microbiology.*, 76(2):493-499.
35 Meyers, R. M., et al., 1985 *Science*, 230:1242-1246.
36 Milosavljevic et al., 1996, *Genomics*, 37: 77-86.
37 Modrich, 1991, *Ann. Rev. Genet.*, 25: 229-253.
38 Nagamine, C. M. et al., 1989, *Am. J. Hum. Genet*, 45:337-339.
39 Newton et al., 1989, *Nucl. Acids Res.* 17: 2503-2516.
40 Novack et al., 1986, *Proc. Natl. Acad. Sci. USA*, 83:586.
41 Nyren, P., et al., 1993 *Anal. Biochem.* 208: 171-175.
42 Orita, M. et al., 1989, *Proc Natl Acad Sci USA*, 86:2766.
43 Prezant, T. R., et al., 1992 *Hum. Mutat.* 1: 159-164.
44 Price, E. P., et al., 2007, *Appln. Environ. Microbiol*, 72:7793-7803.
45 Prince, J. A., et al., 2001 *Genome Res*, 11(1):152-162.
46 Protocols for Oligonucleotides and Analogues; Synthesis and Properties", Methods in Molecular Biology Series, Volume 20, Ed. Sudhir Agrawal, Humana ISBN: 0-89603-247-7, 1993.
47 Ramsay, 1998, *Nature Biotech.* 16: 40-44.
48 Reinhart et al., 2012, *Clinical Microbiology Reviews* 25(4): 609-634.
49 Saleeba, J. A., et al., 1992 Huma. Mutat, 1:63-69
50 Salimullah, et al., 2005, *Cellular and Mol. Biol. Letts*, 10: 237-245
51 Sapolsky and Lishutz, 1996, *Genomics* 33: 445-456
52 Schena et al., 1995, *Science* 270: 467.
53 Shalon, et al., 1996, *Genome Res.* 6: 639.
54 Sheffield et al., 1989, *Proc. Natl. Acad. Sci. USA* 86: 232-236
55 Shenk et al., 1975, *Proc. Natl. Acad. Sci. USA*, 72:989.
56 Shoemaker et al., 1996, *Nat. Genet.* 14: 450-456.
57 Smith-Sorenson et al., 1993, *Human Mutation* 2:274-285.
58 Sokolov, B. P., 1990, *Nucl. Acids Res.* 18: 3671.
59 Sooknanan et al., 1994, *Biotechniques* 17:1077-1080.
60 Stephens, A. J., Inman-Bamber, J., Giffard, P. M., and Huygens, F., 2008, *Clinical Chemistry.* 54(2):432-436.
61 Syvanen, A. C, et al., 1990 Genomics, 8: 684-692.
62 Syvanen, A. C, et al., 1993, *Amer. J. Hum. Genet.* 52: 46-59.
63 Syvanen, A. C., 2001, *Nat. Rev. Genet.* 2, 930-942.
64 Thelwell et al., 2000 *Nucleic Acid Res.* 28(19): 3752-3761.

65 Tijssen, P., 1985, Practice and Theory of Enzyme Immunoassays: Laboratory Techniques in Biochemistry and Molecular Biology, Elsevier Science Publishers, Amsterdam, The Netherlands.
66 Tyagi et al., 1996, Proc. Natl. Acad. Sci. USA 93:5395-5400.
67 Tyagi, S and Kramer, F. R., 1996, Nat. Biotechnol, 14: 303-308

68 Ugozzoli, L., et al., 1992, GATA, 9: 107-112.
69 Wartell et al., 1990 Nucl. Acids Res. 18:2699-2705
70 Weisburg W G, et al., (1991) J Bacteriol. 173 (2): 697-703.
71 Wodicka et al, 1997, Nat. Biotech. 15: 1-15.
72 Xiao and Kwok, 2003, Genome Research, 13(5): 932-939.
73 Yershov et al., 1996, Genetics 93: 4913-4918.

The invention claimed is:

1. A method of identifying a bacterial species present in a sample, said method comprising analysing at least a portion of a bacterial 16S rRNA gene from the sample for the presence or absence of at least one single nucleotide polymorphism (SNP),
wherein analysing at least a portion of the bacterial 16S rRNA gene comprises:
a) amplifying the bacterial 16S rRNA gene with oligonucleotide primers comprising SEQ ID Nos: 56 and 57 to produce a DNA amplification product comprising the at least one SNP, and
b) using high-resolution melt analysis to analyse the DNA amplification product, thereby identifying the bacterial species;
wherein the at least one SNP is at a position corresponding to at least one of positions 737, 755, 762, and 776 of the 16S rRNA gene set forth in SEQ ID NO: 1;
the bacterial species is selected from the group consisting of *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei*; and the sample is selected from the group consisting of: hair, skin, nails, biological tissue, sputum, saliva, cerebrospinal fluid, urine and blood.

2. The method of claim 1, wherein the at least one SNP in the at least a portion of the bacterial 16S rRNA gene is at least two SNPs at a position corresponding to at least two of positions 737, 755, 762, and 776 of the 16S rRNA gene set forth in SEQ ID NO: 1.

3. The method of claim 1, further comprising treating a subject from whom the sample is collected and who is identified as having a bacterial infection, by administering to the subject an antibiotic agent for treating the bacterial infection in the subject.

4. The method of claim 2, wherein said method comprises analysing at least a portion of a bacterial 16S rRNA gene from the sample for the presence or absence of:

single nucleotide polymorphisms in the at least a portion of the bacterial 16S rRNA gene or gene product at a position corresponding to all of positions 737, 755, 762, and 776 of the 16S rRNA gene set forth in SEQ ID NO: 1.

5. The method of claim 1, wherein said method further comprises the step of determining whether the bacterium is resistant to a therapeutic agent.

6. A kit for identifying a bacterial species present in a sample, said kit comprising:

oligonucleotides of SEQ ID NO: 56 and 57; and an enzyme, buffer, and/or deoxynucleotides for amplifying the bacterial 16S rRNA gene for high-resolution melt analysis;

wherein the bacterial species are selected from the group consisting of *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei.*

7. The method of claim 1, wherein the bacterial species is identified from among the bacteria based on the presence or absence of the at least one SNP, wherein the bacterial species is: *Bacillus anthracis* when there is a T at position 737, A at position 755, C at position 762 and G at position 776; *Clostridium botulinum* type A or *Clostridium botulinum* type B when there is a T at position 737, G at position 755, C at position 762 and T at position 776; *Clostridium botulinum* type C when there is a T at position 737, A at position 755, T at position 762 and T at position 776; *Clostridium botulinum* type D when there is a C at position 737, A at position 755, T at position 762 and T at position 776; *Clostridium botulinum* type G when there is a T at position 737, G at position 755, C at position 762 and G at position 776; *Yersinia pestis* when there is a C at position 737, G at position 755, T at position 762 and G at position 776; *Francisella tularensis* when there is a T at position 737, A at position 755, G at position 762 and G at position 776; *Vibrio cholerae* when there is a C at position 737, A at position 755, T at position 762 and G at position 776; and

*Burkholderia pseudomallei* when there is a C at position 737, G at position 755, C at position 762 and G at position 776.

8. The method of claim 1, wherein the oligonucleotide primers consist of SEQ ID Nos: 56 and 57.

* * * * *

SEQUENCE LISTING

```
Sequence total quantity: 57
SEQ ID NO: 1            moltype = DNA  length = 1542
FEATURE                 Location/Qualifiers
source                  1..1542
                        mol_type = genomic DNA
                        organism = Escherichia coli
SEQUENCE: 1
aaattgaaga gtttgatcat ggctcagatt gaacgctggc ggcaggccta acacatgcaa   60
gtcgaacggt aacaggaaga agcttgcttc tttgctgacg agtggcggac gggtgagtaa  120
tgtctgggaa actgcctgat ggaggggat aactactgga aacggtagct aataccgcat  180
aacgtcgcaa gaccaaagag ggggaccttc gggcctcttg ccatcggatg tgcccagatg  240
ggattagcta gtaggtgggg taacggctca cctaggcgac gatccctagc tggtctgaga  300
ggatgaccag ccacactgga actgagacac ggtccagact cctacgggag gcagcagtgg  360
ggaatattgc acaatgggcg caagcctgat gcagccatgc cgcgtgtatg aagaaggcct  420
tcgggttgta aagtactttc agcggggagg aagggagtaa agttaatacc tttgctcatt  480
gacgttaccc gcagaagaag caccggctaa ctccgtgcca gcagccgcgg taatacgag  540
ggtgcaagcg ttaatcggaa ttactggcg taaagcgcac gcaggcggtt tgttaagtca  600
gatgtgaaat ccccgggctc aacctgggaa ctgcatctga tactggcaag cttgagtctc  660
gtagaggggg gtagaattcc aggtgtagcg gtgaaatgcg tagagatctg gaggaatacc  720
ggtggcgaag gcggcccct ggacgaagac tgacgctcag gtgcgaaagc gtggggagca  780
aacaggatta gataccctgg tagtccacgc cgtaaacgat gtcgacttgg aggttgtgcc  840
cttgaggcgt ggcttccgga gctaacgcgt taagtcgacc gcctggggag tacggccgca  900
aggttaaaac tcaaatgaat tgacggggc ccgcacaagc ggtggagcat gtggtttaat  960
tcgatgcaac gcgaagaacc ttacctgtc ttgacatcca cagaactttc cagagatgga 1020
ttggtgcctt cgggaactgt gagacaggtg ctgcatggct gtcgtcagct cgtgttgtga 1080
aatgttgggt taagtcccgc aacgagcgca accttatct tttgttgcca gcggtccggc 1140
cgggaactca aaggagactg ccagtgataa actgaggaa ggtggggatg acgtcaagtc 1200
atcatggccc ttacgaccag ggctacacac gtgctacaat acgtgcataca aagagaagcg 1260
acctcgcgag agcaagcgga cctcataaag tgcgtcgtag tccggattgg agtctgcaac 1320
tcgactccat gaagtcggaa tcgctagtaa tcgtggatca gaatgccacg gtgaatacgt 1380
tcccgggcct tgtacacacc gcccgtcaca ccatgggagt gggttgcaaa agaagtaggt 1440
agcttaacct tcgggagggc gcttaccact ttgtgattca tgactgggt gaagtcgtaa 1500
caaggtaacc gtaggggaac ctgcggttgg atcacctcct ta                    1542

SEQ ID NO: 2            moltype = DNA  length = 1555
FEATURE                 Location/Qualifiers
source                  1..1555
                        mol_type = genomic DNA
                        organism = Staphylococcus aureus
SEQUENCE: 2
ttttatggag agtttgatcc tggctcagga tgaacgctgg cggcgtgcct aatacatgca   60
agtcgagcga acggacgaga agcttgcttc tctgatgtta gcggcggacg ggtgagtaac  120
acgtggataa cctacctata agactgggat aacttcggga aaccggagct aataccggat  180
aatattttga accgcatggt tcaaaagtga aagacggtct tgctgtcact tatagatgga  240
tccgcgctgc attagctagt tggtaaggta acggcttacc aaggcaacga tgcatagccg  300
acctgagagg gtgatcggcc acactggaac tgagacacgg tccagactcc tacgggaggc  360
agcagtaggg aatcttccgc aatgggcgaa agcctgacgg agcaacgccg cgtgagtgat  420
gaaggtcttc ggatcgtaaa actctgttat tagggaagaa catatgtgta agtaactgtg  480
cacatcttga cggtacctaa tcagaaagcc acggctaact acgtgccagc agccgcggta  540
atacgtaggt ggcaagcgtt atccggaatt attgggcgta aagcgcgcgt aggcggtttt  600
ttaagtctga tgtgaaagcc cacggctcaa ccgtggaggg tcattggaaa ctggaaaact  660
tgagtgcaga agaggaaagt ggaattccat gtgtagcggt gaaatgcgca gagatatgga  720
ggaacaccag tggcgaaggc gactttctgg tctgtaactg acgctgatgt gcgaaagcgt  780
ggggatcaaa caggattaga taccctggta gtccacgccg taaacgatga gtgctaagtg  840
ttaggggtt tccgccctt agtgctgcag ctaacgcatt aagcactccg cctggggagt  900
acgaccgcaa ggttgaaact caaaggaatt gacgggaccc gcacaagcg gtggagcatg  960
tggtttaatt cgaagcaacg cgaagaacct taccaaatct tgacatcctt tgacaactct 1020
agagatagag ctttccccttc ggggacaaa agtgacaggt ggtgcatggt tgtcgtcagc 1080
tcgtgtcgtg agatgttggg ttaagtcccg caacgagcgc aaccttaag cttagttgcc 1140
atcattaagt tgggcactct aagttgactg ccggtgacaa accggaggaa ggtggggatg 1200
acgtcaaatc atcatgcccc ttatgatttg ggctacacac gtgctacaat ggacaataca 1260
aagggcagcg aaaccgtgag gtcaagcaaa tcccataaag ttgttctcag ttcggattgt 1320
agtctgcaac tcgactacat gaagctggaa tcgctagtaa tcgtagatca gcatctacg 1380
gtgaatacgt tcccgggtct tgtacacacc gcccgtcaca ccacgagagt ttgtaacacc 1440
cgaagccggt ggagtaacct tttaggagct agccgtcgaa ggtgggacaa atgattgggg 1500
tgaagtcgta acaaggtagc cgtatcggaa ggtgcggctg gatcacctcc tttct       1555
```

| SEQ ID NO: 3 | moltype = DNA length = 1554 |
|---|---|
| FEATURE | Location/Qualifiers |
| source | 1..1554 |
| | mol_type = genomic DNA |
| | organism = Staphylococcus epidermidis |

SEQUENCE: 3

```
ttttatggag agtttgatcc tggctcagga tgaacgctgg cggcgtgcct aatacatgca   60
agtcgagcga acagacgagg agcttgcttc tctgacgtta gcggcggacg ggtgagtaac  120
acgtggataa cctacctata agactgggat aacttcggga aaccggagct aataccggat  180
aatatattga accgcatggt tcaatagtga aagacggttt tgctgtcact tatagatgga  240
tccgcgccgc attagctagt tggtaaggta acggcttacc aaggcaacga tgcgtagccg  300
acctgagagg gtgatcggcc acactggaac tgagacacgg tccagactcc tacgggaggc  360
agcagtaggg aatcttccgc aatgggcgaa agcctgacgg agcaacgccg cgtgagtgat  420
gaaggtcttc ggatcgtaaa actctgttat tagggaagaa caaatgtgta agtaactatg  480
cacgtcttga cggtacctaa tcagaaagcc acggctaact acgtgccagc agccgcggta  540
atacgtaggt ggcaagcgtt atccggaatt attgggcgta aagcgcgcgt aggcggtttt  600
ttaagtctga tgtgaaagcc cacggctcaa ccgtggaggg tcattggaaa ctggaaaact  660
tgagtgcaga agaggaaagt ggaattccat gtgtagcggt gaaatgcgca gatatgtgga  720
ggaacaccag tggcgaaggc gactttctgg tctgtaactg acgctgatgt gcgaaagcgt  780
ggggatcaaa caggattaga taccctgta gtccacgccg taaacgatga gtgctaagtg  840
ttaggggggtt tccgcccctt agtgctgcag ctaacgcatt aagcactccg cctggggagt  900
acgaccgcaa ggttgaaact caaaggaatt gacggggacc cgcacaagcg gtggagcatg  960
tggtttaatt cgaagcaacg cgaagaacct taccaaatct tgacatcctc tgacccctct 1020
agagatagag ttttcccctt cggggggacag agtgacaggt ggtgcatggt tgtcgtcagc 1080
tcgtgtcgtg agatgttggg ttaagtcccg caacgagcgc aacccttaag cttagttgcc 1140
atcattaagt tgggcactct aagttgactg ccggtgacaa accggaggaa ggtggggatg 1200
acgtcaaatc atcatgcccc ttatgattg ggctacacac gtgctacaat ggacaataca 1260
aagggcagcg aaaccgcgag gtcaagcaaa tcccataaag ttgttctcag ttcggattgt 1320
agtctgcaac tcgactatat gaagctgaa tcgctagtaa tcgtagatca gcatgctacg 1380
gtgaatacgt tcccgggtct tgtacacacc gcccgtcaca ccacgagagt ttgtaacacc 1440
cgaagccggt ggagtaacca tttggagcta gccgtcgaag gtgggacaaa tgattggggt 1500
gaagtcgtaa caaggtagcc gtatcggaag gtgcggctgg atcacctcct ttct        1554
```

| SEQ ID NO: 4 | moltype = DNA length = 1514 |
|---|---|
| FEATURE | Location/Qualifiers |
| source | 1..1514 |
| | mol_type = genomic DNA |
| | organism = Streptococcus pneumoniae |

SEQUENCE: 4

```
gtttgatcct ggctcaggac gaacgctggc ggcgtgccta atacatgcaa gtagaacgct   60
gaaggaggag cttgctctct ggatgagtt gcgaacgggt gagtaacgcg taggtaacct  120
gcctggtagc ggggataac tattggaaac gatagctaat accgcataag agtggatgtt  180
gcatgacatt tgcttaaaag gtgcacttgc atcactacca gatgagcctg cgttgtatta  240
gctagttggt ggggtaacgg ctcaccaagg cgacgataca tagccgacct gagagggtga  300
tcggccacac tgggactgag acacggccca gactcctacg ggaggcagca gtagggaatc  360
ttcggcaatg gacggaagtc tgaccgagca acgccgcgtg agtgaagaag gttttcggat  420
cgtaaagctc tgttgtaaga agaacgagt gtgagagtg aaagttcac actgtgacgg  480
tatcttacca gaaagggacg gctaactacg tgccagcagc cgcggtaata cgtaggtccc  540
gagcgttgtc cggatttatt gggcgtaaag cgagcgcagg cggttagata agtctgaagt  600
taaaggctgt ggcttaacca tagtaggctt tggaactgt taacttgag tgcaagaggg  660
gagagtgaa ttccatgtgt agcggtgaaa tgcgtagata tatggaggaa caccggtgg  720
gaaagcggct ctctggcttg taactgacgc tgaggctcga aagcgtgggg agcaaacagg  780
attagatacc ctggtagtcc acgccgtaaa cgatgagtgc taggtgttag acccttccg  840
gggtttagtg ccgtagctaa cgcattaagc actccgcctg gggagtacga ccgcaaggtt  900
gaaactcaaa ggaattgacg gggcccgca caagcggtgg agcatgtgtt taattcgaa  960
gcaacgcgaa gaaccttacc aggtcttgac atccctctga ccgctctaga gatagagttt 1020
tccttcggga cagaggtgac aggtggtgca tggttgtcgt cagctcgtgt cgtgagatgt 1080
tgggttaagt cccgcaacga gcgcaacccc tattgttagt tgccatcatt cagttgggca 1140
ctctagcgag actgccggta ataaaccgga ggaaggtggg gatgacgtca atcatcatg 1200
cccccttatga cctgggctac acacgtgcta caacgagt cgcaagccgg 1260
tgacggcaag ctaatctctt aaagccagtc tcagttcgga ttgtaggctg caactcgcct 1320
acatgaagtc ggaatcgcta gtaatcgcgg atcagcacgc cgcggtgaat acgttcccgg 1380
gccttgtaca caccgcccgt cacaccacga gtttgtaa cacccgaagt cggtgaggta 1440
accgtaagga gccagccgcc taaggtggga tagatgattg gggtgaagtc gtaacaaggt 1500
agccgtatcg gaag                                                   1514
```

| SEQ ID NO: 5 | moltype = DNA length = 1501 |
|---|---|
| FEATURE | Location/Qualifiers |
| source | 1..1501 |
| | mol_type = genomic DNA |
| | organism = Streptococcus agalactiae |

SEQUENCE: 5

```
gacgaacgct ggcggcgtgc ctaatacatg caagtagaac gctgaggttt ggtgtttaca   60
ctagactgat gagttgcgaa cgggtgagta acgcgtaggt aacctgccct atagcggggg  120
ataactattg gaaacgatag ctaataccgc ataagagtaa ttaacacatg ttagttattt  180
aaaaggagca attgcttcac tgtgagatgg acctgcgttg tattagctag ttggtgaggt  240
aaaggctcac aaggcgacg atacatagcc gacctgagag ggtgatcggc cacactggga  300
ctgagacacg gcccagactc ctacgggagg cagcagtagg gaatcttcgg caatggacgg  360
aagtctgacc gagcaacgcc gcgtgagtga agaaggtttt cggatcgtaa agctctgttg  420
```

```
ttagagaaga acgttggtag gagtggaaaa tctaccaagt gacggtaact aaccagaaag    480
ggacggctaa ctacgtgcca gcagccgcgg taatacgtag gtcccgagcg ttgtccggat    540
ttattgggcg taaagcgagc gcaggcggtt ctttaagtct gaagttaaag gcagtggctt    600
aaccattgta cgctttggaa actggaggac ttgagtgcag aaggggagag tggaattcca    660
tgtgtagcgg tgaaatgcgt agatatatgg aggaacaccg gtggcgaaag gcgctctctg    720
gtctgtaact gacgctgagg ctcgaaagcg tggggagcaa acaggattag ataccctggt    780
agtccacgcc gtaaacgatg agtgctaggt gttaggccct ttccggggct tagtgccgca    840
gctaacgcat taagcactcc gcctggggag tacgaccgca aggttgaaac tcaaaggaat    900
tgacgggggc ccgcacaagc ggtggagcat gtggtttaat tcgaagcaac gcgaagaacc    960
ttaccaggtc ttgacatcct tctgaccggc ctagagatag gctttctctt cggagcagaa   1020
gtgacaggtg gtgcatggtt gtcgtcagct cgtgtcgtga gatgttgggt taagtcccgc   1080
aacgagcgca acccctattg ttagttgcca tcattaagtt gggcactcta gcgagactgc   1140
cggtaataaa ccggaggaag gtggggatga cgtcaaatca tcatgcccct tatgacctgg   1200
gctacacacg tgctacaatg gttggtacaa cgagtcgcaa gccggtgacg gcaagctaat   1260
ctcttaaagc caatctcagt tcggattgta ggctgcaact cgcctacatg aagtcggaat   1320
cgctagtaat cgcggatcag cacgccgcgg tgaatacgtt cccgggcctt gtacacaccg   1380
cccgtcacac cacgagagtt tgtaacaccc gaagtcggtg aggtaacctt ttaggagcca   1440
gccgcctaag gtgggataga tgattggggt gaagtcgtaa caaggtagcc gtatcggaag   1500
g                                                                   1501

SEQ ID NO: 6            moltype = DNA  length = 1543
FEATURE                 Location/Qualifiers
source                  1..1543
                        mol_type = genomic DNA
                        organism = Streptococcus pyogenes
SEQUENCE: 6
gagagtttga tcctggctca ggacgaacgc tggcggcgtg cctaatacat gcaagtagaa    60
cgctgagaac tggtgcttgc accggttcaa ggagttgcga acgggtgagt aacgcgtagg   120
taacctacct catagcgggg gataactatt ggaaacgata gctaataccg cataagagag   180
actaacgcat gttagtaatt aaaaggggca aattgctcca ctatgagatg gacctgcgtt   240
gtattagcta gttggtgagg taaaggctca ccaaggcgac gatacatagc cgacctgaga   300
gggtgatcgg ccacactggg actgagacac ggcccagact cctacgggag gcagcagtag   360
ggaatcttcg gcaatggggg caaccctgac cgagcaacgc cgcgtgagtg aagaaggttt   420
tcggatcgta aagctctgtt gttagagaag aatgatggtg gagtggaaaa atccaccaag   480
tgacggtaac taaccagaaa gggacggcta actacgtgcc agcagccgcg gtaatacgta   540
ggtcccgagc gttgtccgga tttattgggc gtaaagcgag cgcaggcggt tttttaagtc   600
tgaagttaaa ggcattggct caaccaatgt acgctttgga aactgagaa cttgagtgca   660
gaaggggaga gtggaattcc atgtgtagcg gtgaaatgcg tagatatatg gaggaacacc   720
ggtggcgaaa gcggctctct ggtctgtaac tgacgctgaa gctcgaaagc gtggggagca   780
aacaggatta gataccctgg tagtccacgc cgtaaacgat gagtgctagg tgttaggccc   840
tttccgggc ttagtgccgg agctaacgca ttaagcactc cgcctgggga gtacgaccgc   900
aaggttgaaa ctcaaaggaa ttgacggggg cccgcacaag cggtggagca tgtggtttaa   960
ttcgaagcaa cgcgaagaac cttaccaggt cttgacatcc cgatgcccgc tctagagata  1020
gagtttttact tcggtacatc ggtgacaggt ggtgcatggt tgtcgtcagc tcgtgtcgtg  1080
agatgttggg ttaagtcccg caacgagcgc aacccctatt gttagttgcc atcattaagt  1140
tgggcactct agcgagactg ccggtaataa accggaggaa ggtggggatg acgtcaaatc   1200
atcatgcccc ttatgacctg gctacacac gtgctacaat ggttggtaca acgagtcgca   1260
agccggtgac ggcaagctaa tctcttaaag ccaatctcag ttcggattgt aggctgcaac   1320
tcgcctacat gaagtcggaa tcgctagtaa tcgcggatca gcacgccgcg gtgaatacgt   1380
tcccgggcct tgtacacacc gcccgtcaca ccacgagagt ttgtaacacc cgaagtcggt   1440
gaggtaacct tattaggagcc agccgcctaa ggtgggatag atgattgggg tgaagtcgta   1500
acaaggtagc cgtatcggaa ggtgcggctg gatcacctcc ttt                    1543

SEQ ID NO: 7            moltype = DNA  length = 1522
FEATURE                 Location/Qualifiers
source                  1..1522
                        mol_type = genomic DNA
                        organism = Enterococcus faecalis
SEQUENCE: 7
agagtttgat cctggctcag gacgaacgct ggcggcgtgc ctaatacatg caagtcgaac    60
gcttctttcc tcccgagtgc ttgcactcaa ttggaaagag gagtggcgga cgggtgagta   120
acacgtgggt aacctaccca tcagagggg ataaacttg gaaacaggtg ctaataccgc   180
ataacagttt atgccgcatg gcataagagt gaaaggcgct ttcgggtgtc gttgatggat   240
ggacccgcgg tgcattagct agttggtgag gtaaccggct caccaaggcc gatgatgcatag   300
ccgacctgag agggtgatcg gccacactgg gactgagaca cggcccagac tcctacggga   360
ggcagcagta gggaatcttc ggcaatggac gaaagtctga ccgagcaacg ccgcgtgagt   420
gaagaaggtt ttcggatcgt aaaactctgt tgttagagaa gaacaaggac gttagtaact   480
gaacgtcccc tgacggtatc taaccagaaa gccacggcta actacgtgcc agcagccgcg   540
gtaatacgta ggtggcaagc gttgtccgga tttattgggc gtaaagcgag cgcaggcggt   600
ttcttaagtc tgatgtgaaa gcccccggct caaccgggga gggtcattgg aaactggag   660
acttgagtgc agaagaggag agtggaattc catgtgtagc ggtgaaatgc gtagatatat   720
ggaggaacac cagtggcgaa ggcggctctc tggtctgtaa ctgacgctga ggctcgaaag   780
cgtgggggagc aaacaggatt agatacctg gtagtccacg ccgtaaacga tgagtgctaa   840
gtgttaggcc ctttccgggcc ttcagtgctg cagcaaacgc attaagcact ccgcctgggg   900
agtacgaccg caaggttgaa actcaaagga attgacgggg gcccgcacaa gcggtggagc   960
atgtggttta attcgaagca acgcgaagaa ccttaccagg tcttgacatc ctttgaccac  1020
tctagagata gagcttttccc ttcggggaca aagtgacagg tggtgcatgg ttgtcgtcag  1080
ctcgtgtcgt gagatgttgg gttaagtccc gcaacgagcg caacccttat tgttagttgc  1140
catcatttag ttgggcactc tagcgagact gccggtgaca aaccggagga aggtggggat   1200
```

```
gacgtcaaat catcatgccc cttatgacct gggctacaca cgtgctacaa tgggaagtac    1260
aacgagtcgc tagaccgcga ggtcatgcaa atctcttaaa gcttctctca gttcggattg    1320
caggctgcaa ctcgcctgca tgaagccgga atcgctagta atcgcggatc agcacgccgc    1380
ggtgaatacg ttcccgggcc ttgtacacac cgcccgtcac accacgagag tttgtaacac    1440
ccgaagtcgg tgaggtaacc ttttggagc cagccgccta aggtgggata gatgattggg    1500
gtgaagtcgt aacaaggtag cc                                             1522

SEQ ID NO: 8           moltype = DNA  length = 1551
FEATURE                Location/Qualifiers
source                 1..1551
                       mol_type = genomic DNA
                       organism = Enterococcus faecium
SEQUENCE: 8
agagtttgat cctggctcag gacgaacgct ggcggcgtgc ctatacatgc aagtcgaacg     60
cttcttttc caccggagct tgctccaccg gaaaagagg agtggcgaac gggtgagtaa     120
cacgtgggta acctgcccat cagaaaggga taacacttgg aaacaggtgc taataccgta    180
taacaaatca aaaccgcatg gttttgattt gaaaggcgct ttcgggtgtc gctgatggat    240
ggacccgcgg tgcattagct agttggtgag gtaacggctc accaaggcca cgatgcatag    300
ccgcacctga gagggtgatc ggccacattg gactgagaca cggcccaaa ctctacggga    360
ggcagcagta gggaatcttc ggcaatggac gaaagtctga ccgagcaacg ccgcgtgagt    420
gaagaaggtt ttcggatcgt aaaactctgt tgttagagaa gaacaaggat gagagtaact    480
gttcatcct tgacggtatc taaccagaaa gccacggcta actacgtgcc agcagccgcg    540
gtaatacgta ggtggcaagc gttgtccgga tttattgggc gtaaagcgag cgcaggcggt    600
tcttaagtct gatgtgaaag cccccggctc aaccggggag ggtcattgga aactgggaga    660
cttgagtgca agaggagaga gtggaattcc atgtgtagcg gtgaaatgcg tagatatatg    720
gaggaacacc agtggcgaag gcggctctct ggtctgtaac tgacgctgag gctcgaaagc    780
gtggggagca acaggatta gatacc.ctgg tagtccacgc cgtaaacgat gagtgctaag    840
tgttggaggg tttccgccct tcagtgctgc agctaacgca ttaagcactc cgcctgggga    900
gtacgaccgc aaggttgaaa ctcaaaggaa ttgacggggg cccgcacaag cggtggagca    960
tgtggtttaa ttcgaagcaa cacgaagaac cttaccaggt cttgacatcc tttgaccact   1020
ctagagatag agcttcccct tcggggggcaa agtgacaggt ggtgcatggt tgtcgtcagc   1080
tcgtgtcgtg agatgttggg ttaagtcccg caacgagcgc aacccttatt gttagttgcc   1140
atcattcagt tgggcactct agcaagactg ccggtgacaa accggaggaa ggtggggatg   1200
acgtcaaatc atcatgcccc ttatgacctg ggctacacac gtgctacaat gggaagtaca   1260
acgagttgcg aagtcgcgag gctaagctaa tctcttaaag cttctctcag ttcggattgt   1320
aggctgcaac tcgcctgcat gaagccgaa tcgctagtaa tcgcggatca gcacgccgcg   1380
tgaatacgtt cccgggcctt gtacacaccg cccgtcacac cacgagagtt tgtaacaccc   1440
gaagtcggtg aggtaacctt tggagccag ccgcctaagg tgggatagat gattgggtg   1500
aagtcgtaac aaggtagccg tatctgaagg tgcggctgga tcacctcctt t            1551

SEQ ID NO: 9           moltype = DNA  length = 1542
FEATURE                Location/Qualifiers
source                 1..1542
                       mol_type = genomic DNA
                       organism = Proteus mirabilis
SEQUENCE: 9
aattgaagag tttgatcatg gctcagattg aacgctggcg gcaggcctaa cacatgcaag     60
tcgagcggta acaggagaaa gcttgctttc ttgctgacga gcggcggacg ggtgagtaat    120
gtatggggat ctgcccgata gagggggata actactggaa acggtggcta ataccgcata    180
atgtctacgg accaaagcag gggctcttcg gaccttgcac tatcggatga acccatatgg    240
gattagctag taggtgggt aaaggctcac ctaggcgacg atctctagct ggtctgagaa    300
gatgatcagc cacactggga ctgagacacg gcccagactc ctacgggagg cagcagtggg    360
gaatattgca caatgggcgc aagcctgatg cagccatgcc gcgtgtatga agaaggcctt    420
agggttgtaa agtactttca gcggggagga aggtgataag gttaatacc.c ttgtcaattg    480
acgttacccg cagaagaagc accggctaac tccgtgccag cagccgcggt aatacggagg    540
gtgcaagcgt taatcggaat tactgggcgt aaagcgcacg caggcggtca attaagtcag    600
atgtgaaagc cccgagctta acttgggaat tgcatctgaa actggttgge tagagtcttg    660
tagaggggg tagaattcca tgtgtagcgg tgaaatgcgt agagatgtgg aggaataccg    720
gtggcgaagg cggccccctg gacaaagact gacgctcagg tgcgaaagcg tggggagcaa    780
acaggattag ataccctggt agtccacgct gtaaacgatg tcgatttaga ggttgtggtc    840
ttgaaccgtg gcttctggag ctaacgcgtt aaatcgaccg cctggggagt acggccgcaa    900
ggttaaaact caaatgaatt gacggggccc gcacaagcgg tggagcatgt ggtttaattc    960
gatgcaacgc gaagaacctt acctactct tgacatccag cgaatccttt agagataag    1020
gagtgccttc gggaacgctg agacaggtgc tgcatggctg tcgtcagctc gtgttgtgaa    1080
atgttgggtt aagtcccgca acgagcgcaa cccttatcct tgttgccag cacgtaatgg   1140
tgggaactca aaggagactg ccggtgataa accggaggaa ggtggggatg acgtcaagtc    1200
atcatggccc ttacgagtag ggctacacac gtgctacaat ggcagataca aagagaagcg    1260
acctcgcgag agcaagcgga actcataaag tctgtcgtag tccggattgg agtctgcaac    1320
tcgactccat gaagtcggaa tcgctagtaa tcgtagatca gaatgctacg gtgaatacgt    1380
tcccgggcct tgtacacacc gcccgtcaca ccatggagt gggttgcaaa agaagtaggt    1440
agcttaacct tcgggagggc gcttaccact ttgtgattca tgactgggt gaagtcgtaa    1500
caaggtaacc gtaggggaac ctgcggttgg atcacctcct ta                       1542

SEQ ID NO: 10          moltype = DNA  length = 1505
FEATURE                Location/Qualifiers
source                 1..1505
                       mol_type = genomic DNA
                       organism = Serratia marcescens
SEQUENCE: 10
```

```
gctcagattg aacgctggcg gcaggcttaa cacatgcaag tcgagcggta gcacagggga   60
gcttgctccc tgggtgacga gcggcggacg ggtgagtaat gtctgggaaa ctgcctgatg  120
gagggggata actactggaa acggtagcta ataccgcata acgtcgcaag accaaagagg  180
gggaccttcg ggcctcttgc catcagatgt gcccagatgg gattagctag taggtggggt  240
aatggctcac ctaggcgacg atccctagct ggtctgagag gatgaccagc cacactggaa  300
ctgagacacg gtccagactc ctacgggagg cagcagtggg gaatattgca caatgggcgc  360
aagcctgatg cagccatgcc gcgtgtgtga agaaggcctt cgggttgtaa agcactttca  420
gcgaggagga aggtggtgag cttaatacgt tcatcaattg acgttactcg cagaagaagc  480
accggctaac tccgtgccag cagccgcggt aatacggagg gtgcaagcgt taatcggaat  540
tactgggcgt aaagcgcacg caggcggttt gttaagtcag atgtgaaatc cccgggctca  600
acctgggaac tgcatttgaa actggcaagc tagagtctcg tagagggggg tagaattcca  660
ggtgtagcgg tgaaatgcgt agagatctgg aggaataccg gtggcgaagg cgggcccctg  720
gacgaagact gacgctcagg tgccaaagcg tggggagcaa acaggattag ataccctggt  780
agtccacgcc gtaaacgatg tcgatttgga ggttgtgccc ttgaggcgtg gcttccggag  840
ctaacgcgtt aaatcgaccg cctggggagt acggccgcaa ggttaaaact caaatgaatt  900
gacggggggcc cgcacaagcg gtggagcatg tggtttaatt cgatgcaacg cgaagaacct  960
tacctactct tgacatccag agaactttcc agagatggat tggtgccttc gggaactctg 1020
agacaggtgc tgcatggctg tcgtcagctc gtgttgtgaa atgttgggtt aagtcccgca 1080
acgagcgcaa cccttatcct tgttgccaga cggttcggcc gggaactcaa aggagactgc 1140
cagtgataaa ctggaggaag gtggggatga cgtcaagtca tcatggccct tacgagtagg 1200
gctacacacg tgctacaatg gcatatacaa agagaagcga cctcgcgaga gcaagcggac 1260
ctcataaagt atgtcgtagt ccggattgga gtctgcaact cgactcctg aagtcggaat 1320
cgctagtaat cgtagatcag aatgctacgg tgaatacgtt cccgggcctt gtacacaccg 1380
cccgtcacac catgggagtg ggttgcaaaa gaagtaggta gcttaacctt cgggagggcg 1440
cttaccactt tgtgattcat gactggggtg aagtcgtaac aaggtaaccg taggggaacc 1500
tgcgg                                                             1505

SEQ ID NO: 11           moltype = DNA   length = 1438
FEATURE                 Location/Qualifiers
source                  1..1438
                        mol_type = genomic DNA
                        organism = Enterobacter aerogenes
variation               1425
                        note = n is a, c, g, or t
SEQUENCE: 11
acgctggcgg caggcctaac acatgcaagt cgagcggtag cacagagagc ttgctctcgg   60
gtgacgagcg gcggacgggt gagtaatgtc tgggaaactg cctgatgggag ggggataact  120
actggaaacg gtagctaata ccgcataacg tcgcaagacc aaagtggggg accttcgggc  180
ctcatgccat cagatgtgcc cagatggat tagctagtag gtggggtaat ggctcaccta  240
ggcgacgatc cctagctggt ctgagaggat gaccagccac actggaactg agacacggtc  300
cagactccta cgggaggcag cagtgggaa tattgcacaa tgggcgcaag cctgatgcag  360
ccatgccgcg tgtatgaaga aggccttcgg gttgtaaagt actttcagcg gaggaaggt  420
cgttaaggtt aataacctg gcgattgacg ttactcgcag aagaagcacc ggctaactcc  480
gtgccagcag ccgcggtaat acggagggtg caagcgttaa tcggaattac tgggcgtaaa  540
gcgcacgcag gcggtctgtc aagtcggatg tgaaatcccc gggctcaacc tgggaactgc  600
attcgaaact ggcaggctag agtcttgtag agggggtag aattccaggt gtagcggtga  660
aatgctagta gatctggagg aataccggtg gcgaaggcgg ccccctggac aaagactgac  720
gctcaggtgc gaaagcgtgg ggagcaaaca ggattagata ccctggtagt ccacgccgta  780
aacgatgtcg acttggaggt tgtgcccttg aggcgtggct tccggagcta acgcgttaag  840
tcgaccgcct ggggagtacg gccgcaaggt taaaactcaa atgaattgac ggggggccgc  900
acaagcggtg gagcatgtgg tttaattcga tgcaacgcga agaaccttac ctactctcgg  960
catccagaga acttagcaga gatgctttgg tgccttcggg aactctgaga caggtgctgc 1020
atggctgtcg tcagctcgtg ttgtgaaatg ttgggttaag tcccgcaacg agcgcaaccc 1080
ttatcctttg ttgccagcgg tccggccggg aactcaaagg agactgccag tgataaactg 1140
gaggaaggtg gggatgacgt caagtcatca tggcccttac gagtagggct acacacgtg 1200
tacaatggca tatacaaaga agcgacct cgcgagagca gcggacctc ataaagtatg 1260
tcgtagtccg gattggagtc tgcaactcga ctccatgaag tcggaatcgc tagtaatcgt 1320
agatcagaat gctacggtga atacgttccc gggccttgta cacaccgccc gtcacaccat 1380
gggagtgggt tgcaaaagaa gtaggtagct taaccttcgg gaggncgctt taccactt   1438

SEQ ID NO: 12           moltype = DNA   length = 1511
FEATURE                 Location/Qualifiers
source                  1..1511
                        mol_type = genomic DNA
                        organism = Enterobacter cloacae
SEQUENCE: 12
tgaacgctgg cggcaggcct aacacatgca agtcgaacgg tagcacagag agcttgctct   60
cgggtgacga gtggcggacg ggtgagtaat gtctgggaaa ctgcctgatg gagggggata  120
actactggaa acggtagcta ataccgcata aygtcgcaag accaaagagg ggaccttcg  180
ggcctcttgc catcagatgt gcccagatgg gattagctag taggtggggt aacggctcac  240
ctaggcgacg atccctagct ggtctgagag gatgaccagc cacactggaa ctgagacacg  300
gtccagactc ctacgggagg cagcagtggg gaatattgca caatgggcgc aagcctgatg  360
cagccatgcc gcgtgtatga agaaggcctt cgggttgtaa agtactttca gcggggagga  420
aggtgttgtg gttaataacc gcagcaattg acgttacccg cagaagaagc accggctaac  480
tccgtgccag cagccgcggt aatacgagg gtgcaagcgt taatcggaat tactgggcgt  540
aaagcgcacg caggcggtct gtcaagtcgg atgtgaaatc cccgggctca acctgggaac  600
tgcattcgaa actggcaggc tggagtcttg tagaggggg tagaattcca ggtgtagcgg  660
tgaaatgcgt agagatctgg aggaataccg gtggcgaagg cggcccctg gacaaagact  720
gacgctcagg tgcgaaagcg tggggagcaa acaggattag atacccctggt agtccacgcc  780
```

```
gtaaacgatg tcgatttgga ggttgtgccc ttgaggcgtg gcttccggag ctaacgcgtt    840
aaatcgaccg cctggggagt acggccgcaa ggttaaaaact caaatgaatt gacgggggcc    900
cgcacaagcg gtggagcatg tggtttaatt cgatgcaacg cgaagaacct tacctggtct    960
tgacatccac agaactttcc agagatggat tggtgccttc gggaactgtg agacaggtgc   1020
tgcatggctg tcgtcagctc gtgttgtgaa atgttgggtt aagtcccgca acgagcgcaa   1080
cccttatcct ttgttgccag cggtccggcc gggaactcaa aggagactgc cagtgataaa   1140
ctggaggaag gtggggatga cgtcaagtca tcatggccct tacgaccagg gctacacacg   1200
tgctacaatg gcgcatacaa agagaagcga cctcgcgaga gcaagcggac ctcataaagt   1260
gcgtcgtagt ccggattgga gtctgcaact cgactccatg aagtcggaat cgctagtaat   1320
cgtagatcag aatgctacgg tgaatacgtt cccgggcctt gtacacaccg cccgtcacac   1380
catgggagtg ggttgcaaaa gaagtaggta gcttaacctt cgggagggcg cttaccactt   1440
tgtgattcat gactggggtg aagtcgtaac aaggtaaccg taggggaacc tgcggctgga   1500
tcacctcctt g                                                        1511

SEQ ID NO: 13           moltype = DNA   length = 1534
FEATURE                 Location/Qualifiers
source                  1..1534
                        mol_type = genomic DNA
                        organism = Klebsiella pneumoniae
variation               11..12
                        note = n is a, c, g, or t
SEQUENCE: 13
agagtttgat nntggctcag attgaacgct ggcggcaggc ctaacacatg caagtcgagc     60
ggtagcacag agacttgct ctcgggtgac gagcggcgga cggtgagta atgtctggga    120
aactgcctga tggaggggga taactactgg aaacggtagc taataccgca taacgtcgca    180
agaccaaagt gggggacctt cgggcctcat gccatcagat gtgcccagat gggattagct    240
agtaggtggg gtaacggctc acctaggcga cgatccctag ctggtctgag aggatgacca    300
gccacactgg aactgagaca cggtccagac tcctacggga ggcagcagtg gggaatattg    360
cacaatgggc gcaagcctga tgcagccatg ccgcgtgtgt gaagaaggcc ttcgggttgt    420
aaagcacttt cagcggggag gaaggcgatg aggttaataa cctcatcgat tgacgttacc    480
ctgcagaaga agcaccggct aactccgtgc cagcagccgc ggtaatacgg agggtgcaag    540
cgttaatcgg aattactggg cgtaaagcgc acgcaggcgg tctgtcaagt cggatgtgaa    600
atccccgggc tcaacctggg aactgcattc gaaactggca ggctagagtc ttgtagaggg    660
gggtagaatt ccaggtgtag cggtgaaatg cgtagagatc tggaggaata ccggtggcga    720
aggcggcccc ctggacaaag actgacgctc aggtgcgaaa gcgtggggag caaacaggat    780
tagatacct ggtagtccac gccgtaaacg atgtcgattt ggaggttgtg cccttgaggc    840
gtggcttccg gagctaacgc gttaaatcga ccgcctgggg agtacggccg caaggttaaa    900
actcaaatga attgacgggg gcccgcacaa gcggtggagc atgtggttta attcgatgca    960
acgcgaagaa ccttacctgg tcttgacatc cacagaactt tccagagatg gattggtgcc   1020
ttcgggaact gtgagacagg tgctgcatgg ctgtcgtcag ctcgtgttgt gaaatgttgg   1080
gttaagtccc gcaacgagcg caaccccttat cctttgttgc cagcgttag gccgggaact   1140
caaaggagac tgccagtgat aaactggagg aaggtgggga tgacgtcaag tcatcatggc   1200
ccttacgacc agggctacac acgtgctaca atggcatata caagagacgc gacctcgcg    1260
agagcaagcg gacctcataa agtatgtcgt agtccggatt ggagtctgca actcgactcc   1320
atgaagtcgg aatcgctagt aatcgtagat cagaatgcta cggtgaatac gttcccgggc   1380
cttgtacaca ccgcccgtca ccatggga gtgggttgca aaagaagtag gtagcttaac    1440
cttcgggagg gcgcttacca ctttgtgatt catgactggg gtgaagtcgt aacaaggtaa   1500
ccgtagggga acctgcggtt ggatcacctc cttt                               1534

SEQ ID NO: 14           moltype = DNA   length = 1536
FEATURE                 Location/Qualifiers
source                  1..1536
                        mol_type = genomic DNA
                        organism = Pseudomonas aeruginosa
SEQUENCE: 14
gaactgaaga gtttgatcat ggctcagatt gaacgctggc ggcaggccta acacatgcaa     60
gtcgagcgga tgaagggagc ttgctcctgg attcagcggc ggacgggtga gtaatgccta    120
ggaatctgcc tggtagtggg ggataacgtc cggaaacggg cgctaatacc gcatacgtcc    180
tgagggagaa agtgggggat cttcggacct cacgctatca gatgagccta ggtcggatta    240
gctagttggt ggggtaaagg cctaccaagg cgacgatccg taactggtct gagaggatga    300
tcagtcacac tggaactgag acacggtcca gactcctacg ggaggcagca gtggggaata    360
ttggacaatg ggcgaaagcc tgatccagcc atgccgcgtg tgtgaagaag gtcttcggat    420
tgtaaagcac tttaagttgg gaggaaggg cagtaagtta accttgctgt ttttgacgtt    480
accaacagaa taagcaccgg ctaacttcgt gccagcagcc gcggtaatac gaagggtgca    540
agcgttaatc ggaattactg ggcgtaaagc gcgcgtaggt ggttcagcaa gttggatgtg    600
aaatccccgg gctcaacctg ggaactgcat ccaaaactac tgagctagag tacggtagag    660
ggtggtggaa tttcctgtgt agcggtgaaa tgcgtagata taggaaggaa caccagtggc    720
gaaggcgacc acctggactg atactgacac tgaggtgcga aagcgtgggg agcaaacagg    780
attagatacc ctggtagtcc acgccgtaaa cgatgtcgac tagccgttgg gatccttgag    840
atcttagtgg cgcagctaac gcgataagtc gaccgcctgg ggagtacggc cgcaaggtta    900
aaactcaaat gaattgacgg gggcccgcac aagcggtgga gcatgtggtt taattcgaag    960
caacgcgaag aaccttacct ggccttgaca tgctgagaac tttccagaga tggattggtg   1020
ccttcggaa ctcagacaca ggtgctgcat ggctgtcgtc agctcgtgtc gtgagatgtt   1080
gggttaagtc ccgtaacgag cgcaaccctt gtccttagtt accagcacct cgggtgggca   1140
ctctaaggag actgccggtg acaaaccgga ggaaggtggg gatgacgtca agtcatcatg   1200
gcccttacgg ccaggctac acacgtgcta caatggtcgg tacaaagggt tgccaagccg   1260
cgaggtggag ctaatcccat aaaaccgatc gtagtccgga tcgcagtctg caactcgact   1320
gcgtgaagtc ggaatcgcta gtaatcgtga atcagaatgt cacggtgaat acgttcccgg   1380
gccttgtaca caccgcccgt cacaccatgg gagtgggttg ctccagaagt agctagtcta   1440
```

```
accgcaaggg ggacggttac cacggagtga ttcatgactg gggtgaagtc gtaacaaggt    1500
agccgtaggg gaacctgcgg ctggatcacc tcctta                              1536

SEQ ID NO: 15           moltype = DNA  length = 1497
FEATURE                 Location/Qualifiers
source                  1..1497
                        mol_type = genomic DNA
                        organism = Acinetobacter calcoaceticus
SEQUENCE: 15
tagagtttga tcctggctca gattgaacgc tggcggcagg cttaacacat gcaagtcgag     60
cggggaaagg tagcttgcta ctggacctag cggcggacgg gtgagtaatg cttaggaatc    120
tgcctattag tgggggacaa cattccgaaa ggaatgctaa taccgcatac gtcctacggg    180
agaaagcagg ggaccttcgg gccttgcgct aatagatgag cctaagtcgg attagctagt    240
tggtggggta aaggcctacc aaggcgacga tctgtagcgg tctgagagga tgatccgcca    300
cactgggact gagacacggc ccagactcct acgggaggca gcagtgggga atattggaca    360
atgggcggaa ccctgatcca gccatgccgc gtgtgtgaag aaggccttat ggttgtaaag    420
cactttaagc gaggaggagg ctactagtat taatactact ggatagtgga cgttactcgc    480
agaataagca ccggctaact ctgtgccagc agccgcggta atacagaggg tgcgagcgtt    540
aatcggattt actgggcgta aagcgtgcgt aggcggccat ttaagtcaaa tgtgaaatcc    600
ccgagcttaa cttgggaatt gcattgcata ctggatggct agagtatggg agaggatggt    660
agaattccag gtgtagcggt gaaatgcgta gagatctgga ggaataccga tggcgaaggc    720
agccatctgg cctaatactg acgctgaggt acgaaagcat caggattaga    780
taccctggta gtccatgccg taaacgatgt ttactagccg ttggggcctt tgaggcttta    840
gtggcgcagc taacgcgata agtagaccgt ctggggagta cggtcgcaag actaaaactc    900
aaatgaattg acggggcccc gcacaagcgg tggagcatgt ggtttaattc gatgcaacgc    960
gaagaacctt acctggcctt gacatactag aaactttcca ggaatttaga   1020
tacaggtgct gcatggctgt cgtcagctcg tgtcgtgaga tgttgggtta    1080
agtcccgcaa cgagcgcaac cctttccctt acttgccagc atttcggatg gaacttttaa    1140
ggatactgcc agtgacaaac tggaggaagg cggggacgac gtcaagtcat catggccctt    1200
acggccaggg ctacacacgt gctacaatgg tcggtacaaa gggttgctac ctagcgatag    1260
gatgctaatc tcaaaaagcc gatcgtagtc cggattggag tctgcaactc gactccatga    1320
agtcggaatc gctagtaatc gcggatcaga atgccggtg atacgttccc gggccttgta    1380
cacaccgccc gtcacaccat gggagtttgt tgcaccagaa gtaggtagtc taaccgcaag    1440
gaggacgctt accacggtgt ggccgatgac tggggtgaag tcgtaacaag gtaacca     1497

SEQ ID NO: 16           moltype = DNA  length = 19
FEATURE                 Location/Qualifiers
misc_feature            1..19
                        note = Forward Primer
source                  1..19
                        mol_type = other DNA
                        organism = synthetic construct
SEQUENCE: 16
cctcttgcca tcggatgtg                                                  19

SEQ ID NO: 17           moltype = DNA  length = 20
FEATURE                 Location/Qualifiers
misc_feature            1..20
                        note = Reverse Primer
source                  1..20
                        mol_type = other DNA
                        organism = synthetic construct
SEQUENCE: 17
ccagtgtggc tggtcatcct                                                 20

SEQ ID NO: 18           moltype = DNA  length = 20
FEATURE                 Location/Qualifiers
misc_feature            1..20
                        note = Forward Primer
source                  1..20
                        mol_type = other DNA
                        organism = synthetic construct
SEQUENCE: 18
cctacgggag gcagcagtag                                                 20

SEQ ID NO: 19           moltype = DNA  length = 20
FEATURE                 Location/Qualifiers
misc_feature            1..20
                        note = Forward Primer
source                  1..20
                        mol_type = other DNA
                        organism = synthetic construct
SEQUENCE: 19
gggaggcagc agtagggaat                                                 20

SEQ ID NO: 20           moltype = DNA  length = 22
FEATURE                 Location/Qualifiers
misc_feature            1..22
                        note = Reverse Primer
```

```
source                  1..22
                        mol_type = other DNA
                        organism = synthetic construct
SEQUENCE: 20
cgatccgaaa accttcttca ct                                              22

SEQ ID NO: 21           moltype = DNA  length = 26
FEATURE                 Location/Qualifiers
misc_feature            1..26
                        note = Forward Primer
source                  1..26
                        mol_type = other DNA
                        organism = synthetic construct
SEQUENCE: 21
aagacggtct tgctgtcact tataga                                          26

SEQ ID NO: 22           moltype = DNA  length = 22
FEATURE                 Location/Qualifiers
misc_feature            1..22
                        note = Reverse Primer
source                  1..22
                        mol_type = other DNA
                        organism = synthetic construct
SEQUENCE: 22
ctatgcatcg ttgccttggt aa                                              22

SEQ ID NO: 23           moltype = DNA  length = 18
FEATURE                 Location/Qualifiers
misc_feature            1..18
                        note = Forward Primer
source                  1..18
                        mol_type = other DNA
                        organism = synthetic construct
SEQUENCE: 23
tgccgcgtga atgaagaa                                                   18

SEQ ID NO: 24           moltype = DNA  length = 21
FEATURE                 Location/Qualifiers
misc_feature            1..21
                        note = Forward Primer
source                  1..21
                        mol_type = other DNA
                        organism = synthetic construct
SEQUENCE: 24
gcgtgaagga tgaaggctct a                                               21

SEQ ID NO: 25           moltype = DNA  length = 21
FEATURE                 Location/Qualifiers
misc_feature            1..21
                        note = Forward Primer
source                  1..21
                        mol_type = other DNA
                        organism = synthetic construct
SEQUENCE: 25
tgatgaaggt tttcggatcg t                                               21

SEQ ID NO: 26           moltype = DNA  length = 29
FEATURE                 Location/Qualifiers
misc_feature            1..29
                        note = Reverse Primer
source                  1..29
                        mol_type = other DNA
                        organism = synthetic construct
SEQUENCE: 26
tgatgtacta ttaacacatc aaccttcct                                       29

SEQ ID NO: 27           moltype = DNA  length = 22
FEATURE                 Location/Qualifiers
misc_feature            1..22
                        note = Reverse Primer
source                  1..22
                        mol_type = other DNA
                        organism = synthetic construct
SEQUENCE: 27
aacgctcgga tcttccgtat ta                                              22

SEQ ID NO: 28           moltype = DNA  length = 21
FEATURE                 Location/Qualifiers
misc_feature            1..21
```

```
                        note = Reverse Primer
source                  1..21
                        mol_type = other DNA
                        organism = synthetic construct
SEQUENCE: 28
cgctcgccac ctacgtatta c                                              21

SEQ ID NO: 29           moltype = DNA  length = 28
FEATURE                 Location/Qualifiers
misc_feature            1..28
                        note = Forward Primer
source                  1..28
                        mol_type = other DNA
                        organism = synthetic construct
SEQUENCE: 29
gttgtaagag aagaacgagt gtgagagt                                       28

SEQ ID NO: 30           moltype = DNA  length = 22
FEATURE                 Location/Qualifiers
misc_feature            1..22
                        note = Reverse Primer
source                  1..22
                        mol_type = other DNA
                        organism = synthetic construct
SEQUENCE: 30
cgtagttagc cgtcccttc tg                                              22

SEQ ID NO: 31           moltype = DNA  length = 24
FEATURE                 Location/Qualifiers
misc_feature            1..24
                        note = Forward Primer
source                  1..24
                        mol_type = other DNA
                        organism = synthetic construct
SEQUENCE: 31
gcggtttgtt aagtcagatg tgaa                                           24

SEQ ID NO: 32           moltype = DNA  length = 22
FEATURE                 Location/Qualifiers
misc_feature            1..22
                        note = Forward Primer
source                  1..22
                        mol_type = other DNA
                        organism = synthetic construct
SEQUENCE: 32
ggtctgtcaa gtcggatgtg aa                                             22

SEQ ID NO: 33           moltype = DNA  length = 21
FEATURE                 Location/Qualifiers
misc_feature            1..21
                        note = Forward Primer
source                  1..21
                        mol_type = other DNA
                        organism = synthetic construct
SEQUENCE: 33
tcaacctggg aactcattcg a                                              21

SEQ ID NO: 34           moltype = DNA  length = 22
FEATURE                 Location/Qualifiers
misc_feature            1..22
                        note = Reverse Primer
source                  1..22
                        mol_type = other DNA
                        organism = synthetic construct
SEQUENCE: 34
ggaattctac cccctctac ga                                              22

SEQ ID NO: 35           moltype = DNA  length = 23
FEATURE                 Location/Qualifiers
misc_feature            1..23
                        note = Reverse Primer
source                  1..23
                        mol_type = other DNA
                        organism = synthetic construct
SEQUENCE: 35
ggaattctac cccctctac aag                                             23

SEQ ID NO: 36           moltype = DNA  length = 1720
FEATURE                 Location/Qualifiers
```

| | | |
|---|---|---|
| source | 1..1720 | |
| | mol_type = genomic DNA | |
| | organism = Aspergillus fumigatus | |

SEQUENCE: 36

```
ggaccgggcc tgtctaggta taagcaattt atacggtgaa actgcgaatg gctcattaaa    60
tcagttatcg tttatttgat agtaccttac tacatggata cctgtggtaa ttctagagct   120
aatacatgct aaaaacctcg acttcggaag gggtgtattt attagataaa aaaccaatgc   180
ccttcggggc tccttggtga atcataataa cttaacgaat cgcatggcct tgcgccggcg   240
atggttcatt caaatttctg ccctatcaac tttcgatggt aggatagtgg cctaccatgg   300
tggcaacggg taacggggaa ttagggttcg attccggaga gggagcctga gaaacggcta   360
ccacatccaa ggaaggcagc aggcgcgcaa attacccaat cccgacacgg ggaggtagtg   420
acaataaata ctgatacggg gctcttttgg gtctcgtaat tggaatgagt acaatctaaa   480
tcccttaacg aggaacaatt ggagggcaag tctggtgcca gcagccgcgg taattccagc   540
tccaatagcg tatattaaag ttgttgcagt taaaaagctc gtagttgaac cttgggtctg   600
gctggccggt ccgcctcacc gcgagtactg tccggctgg  accttccctt ctggggaacc   660
tcatggcctt cactgctgt  gggggaacc aggacttta  ctgtgaaaaa attagagtgt   720
tcaaagcagg cctttgctcg aatacattag catggaataa tagaatagga cgtgcggttc   780
tattttgttg gtttctagga ccgccgtaat gattaatagg gatagtcggg ggcgtcagta   840
ttcagctgtc agaggtgaaa ttcttggatt tgctgaagac taactactgc gaaagcattc   900
gccaaggatg ttttcattaa tcaggaacga aagttagggg atcgaagacg atcagatacc   960
gtcgtagtct taaccataaa ctatgccgac tagggatcgg gcggtgtttc tatgatgacc  1020
cgctcggcac cttacgagaa atcaaagttt ttgggttctg gggggagtat gtcgcaagg   1080
ctgaaactta agaaattga cggaaggca ccaaggcg tggagcctgc ggcttaattt   1140
gactcaacac ggggaaactc accaggtcca gacaaaataa ggattacag attgagagct  1200
cttcttgat cttttggatg gtggtgcatg gccgttctta gttggtggag tgatttgtct  1260
gcttaattgc gataacgaac gagacctcgg ccttaaata gcccggtccg cattgcggg  1320
ccgctggctt cttaggggga ctatcggctc aagccgatgg aagtgcgcgg caataacagg  1380
tctgtgatgc ccttagatgt tctgggccgc acgcgcgcta cactgacagg gccagcgagt  1440
acatcacctt ggccgagagg tctgggtaat cttgttaaac cctgtcgtgc tggggataga  1500
gcattgcaat tattgctctt caacgaggaa tgcctagtag cagagtca tcagctcgtg   1560
ccgattacgt ccctgccctt tgtacacacc gcccgtcgct actaccgatt gaatggctca  1620
gtgaggcctt cggactggct caggggagtt ggcaacgact ccccagagcc ggaaagttgg  1680
tcaaacccgg tcattagagg aaagaaaaaa ttaaacacgg                        1720
```

| | | |
|---|---|---|
| SEQ ID NO: 37 | moltype = DNA length = 1632 | |
| FEATURE | Location/Qualifiers | |
| source | 1..1632 | |
| | mol_type = genomic DNA | |
| | organism = Candida albicans | |
| variation | 1587 | |
| | note = n is a, c, g, or t | |

SEQUENCE: 37

```
tcagttatcg tttatttgat agtaccttac tacttggata accgtggtaa ttctagagct    60
aatacatgct aaaatcccg actgtttgga agggatgtat ttattagata aaaaatcaat   120
gccttcgggc tctttgatga ttcataataa cttttcgaat cgcatggcct tgtgctggcg   180
atggttcatt caaatttctg ccctatcaac tttcgatggt aggatagtgg cctaccatgg   240
tttcaacggg taacggggaa taagggttcg attccggaga gggagcctga gaaacggcta   300
ccacatccaa ggaaggcagc aggcgcgcaa attacccaat cccgacacgg ggaggtagtg   360
acaataaata acgatacagg gccctttggg gtcttgtaat tggaatgagt acaatgtaaa   420
taccttaacg aggaacaatt ggagggcaag tctggtgcca gcagccgcgg taattccagc   480
tccaaaagcg tatattaaag ttgttgcagt taaaaagctc gtagttgaac cttgggtctg   540
gctggccggt ccatcttttt gatgcgtact ggacccagcc gagcctttcc ttctgggtag   600
ccatttatgg cgaaccagga ctttttactt gaaaaaatta gagtgttcaa agcaggcctt   660
tgctcgaata tattagcatg gaataataga ataggacgtt atggttctat tttgttggtt   720
tctaggacca tcgtaatgat taatagggac ggtcgggggc atcagtattc agttgtcaga   780
ggtgaaattc ttggatttac tgaagactaa ctactgcgaa agcatttacc aaggacgttt   840
tcattaatca agaacgaaag ttagggggatc gaagatgatc agataccgtc gtagtcttaa   900
ccataaacta tgccgactag ggatcggttg ttgttctttt attgacgcaa tcggcaccct   960
acgagaaatc aaagtctttg ggttctgggg ggagtatggt cgcaaggctg aaacttaaag  1020
gaattgacgg aagggcacca caggatgg agcctgcggc ttaatttgac tcaacacgg   1080
gaaactcacc aggtccagac acaataagga ttgacagatt gagagctctt tcttgatttt  1140
gtgggtggtg gtgcatggcc gttcttagtt ggtggagtga tttgtctgct taattgcgat  1200
aacgaacgag accttaacct actaaatagt gctgctagca tttgctggta tagtcacttc  1260
ttagagacgt tatcgacttc aagtcgatgg aagtttgagg caataacagg tctgtgatgc  1320
ccttagacgt tctgggccgc acgcgcgcta cactgacagg gccagcgagt ataagccttg  1380
gccgagaggt ctgggaaatc ttgtgaaact ccgtcgtgct ggggatagag cattgtaatt  1440
gttgctcttc aacgaggaat tcctagtaag cgcaagtcat cagcttgcgt tgattacgtc  1500
cctgcccttt gtacacaccg cccgtcgcta ctaccgattg aatggcttag tgaggcctcc  1560
ggattggttt aggaagggg  gcaactncat tctggaaccg agaagctggt caaacttggt  1620
catttagagg aa                                                     1632
```

| | | |
|---|---|---|
| SEQ ID NO: 38 | moltype = DNA length = 1732 | |
| FEATURE | Location/Qualifiers | |
| source | 1..1732 | |
| | mol_type = genomic DNA | |
| | organism = Candida glabrata | |

SEQUENCE: 38

```
agtatttgtc taaaaattaa gccatgcatg tctaagtata agcaatttat acagtgaaac    60
tgcgaatggc tcattaaatc agttatcgtt tatttgatag ttccttttact acatggtata   120
```

```
actgtggtaa ttctagagct aatacatgct taaaatctcg acctcttgga agagatgtat    180
ttattagata aaaaatcaat gtcttcggac tttttgatga ttcataataa cttttcgaat    240
cgcatggcct tgtgctggcg atggttcatt caaatttctg ccctatcaac tttcgatggt    300
aggatagtgg cctaccatgg tttcaacggg taacggggaa taagggttcg attccggaga    360
gggagcctga gaaacggcta ccacatccaa ggaaggcagc aggcgcgcaa attacccaat    420
cctgacacag ggaggtagtg acaataaata acgatacagg gcccattcgg gtcttgtaat    480
tggaatgagt acaatgtaaa tacctaacg aggaacaatt ggagggcaag tctggtgcca    540
gcagccgcgg taattccagc tccaatagcg tatattaaag ttgttgcagt taaaaagctc    600
gtagttgaac tttgggcctg ggtggccggt ccgattttt cgtgtactgg aatgcacccg    660
ggcctttcct tctggctaac cccaagtcct tgtggcttgg cggcgaacca ggactttac    720
tttgaaaaaa ttagagtgtt caaagcaggc gtattgctcg aatatattag catgaataa    780
tggaatagga cgtttggttc tattttgttg gtttctagga ccatcgtaat gattaatagg    840
gacggtcggg ggcatcagta ttcaattgtc agaggtgaaa ttcttggatt tattgaagac    900
taactactgc gaaagcattt gccaaggacg ttttcattaa tcaagaacga aagttagggg    960
atcgaagatg atcagatacc gtcgtagtct taaccataaa ctatgccgac tagggatcgg   1020
gtggtgtttt tttagtgacc cactcggcac cttacgagaa atcaaagtct ttgggttctg   1080
gggggagtat ggtcgcaagg ctgaaactta aaggaattga cggaagggca ccaccaggag   1140
tggagcctgc ggcttaattt gactcaacac ggggaaactc accaggtcca gacacaataa   1200
ggattgacag attgagagct cttcttgat tttgtgggtg gtggtgcatg gccgttctta   1260
gttggtggag tgatttgtct gcttaattgc gataacgaac gagaccttaa cctactaaat   1320
agtggtgcta gcatttgctg gttgtccact tcttagaggg actatcggtt tcaagccgat   1380
ggaagtttga ggcaataaca ggtctgtgat gcccttagac gttctgggcc gcacgcgcgc   1440
tacactgacg gagccagcga gtctaacctt ggccgagagg tcttggtaat cttgtgaaac   1500
tccgtcgtgc tggggataga gcattgtaat tattgctctt caacgaggaa ttcctagtaa   1560
gcgcaagtca tcagcttgcg ttgattacgt ccctgccctt tgtacacacc gcccgtcgct   1620
agtaccgatt gaatggctta gtgaggcctc aggatctgct tagaagaggg ggcgactcca   1680
cttcagagcg gagaatctgg tcaaacttgg tcatttagag gaaacccaaa aa           1732

SEQ ID NO: 39          moltype = DNA   length = 1223
FEATURE                Location/Qualifiers
source                 1..1223
                       mol_type = genomic DNA
                       organism = Candida parapsilosis
SEQUENCE: 39
gcctgagaaa cggctaccac atccaaggaa ggcagcaggc gcgcaaatta cccaatcccg     60
acacggggag gtagtgacaa taaataacga tacagggccc tttcgggtct tgtaattgga    120
atgagtacaa tgtaaatacc ttaacgagga acaattggag ggcaagtctg gtgccagcag    180
ccgcggtaat tccagctcca aaagcgtata ttaaagttgt tgcagttaaa aagctcgtag    240
ttgaaccttg ggccttggctg gccggtccat ctttttgat gcgtactgga cccagccgag    300
cctttccttc tggctagcct ttttggcgaa ccaggacttt tactttgaaa aaattagagt    360
gttcaaagca ggcctttgct cgaatatatt agcatggaat aatagaatag gacgttatgg    420
ttctatttttg ttggtttcta ggaccatcgt aatgattaat agggacggtc gggggtatca    480
gtattcagta gtcagaggtg aaattcttgg atttactgaa gactaactac tgcgaaagca    540
tttaccaagg acgttttcat taatcaagaa cgaaagttag gggatcgaag atgatcagat    600
accgtcgtag tcttaaccat aaactatgcc gactagggat cggttgttgt tcttttattg    660
acgcaatcgg caccttacga gaaatcaaag tctttgggtt ctgggggag tatggtcgca    720
aaggctgaaa cttaaaggaa ttgacggaag gcaccaccag gtggagcc ctgcggctta    780
atttgactca acacggggaa actcaccagg tccagacaca ataaggattg acagattgag    840
agctcttttct tgattttgtg ggtggtggtg catggccgtt cttagttggt ggagtgattt    900
gtctgcttaa ttgcgataac gaacgagacc ttaacctact aaatagtgct gctagctttt    960
gctggtatag tcacttctta gagggactat cgatttcaag tcgatggaag tttgaggcaa   1020
taacaggtct gtgatgccct tagacgttct gggccgcacg cgcgctacac tgacggagcc   1080
agcgagtata aaccttggcc gagaggtctg ggaaatcttg tgaaactccg tcgtgctggg   1140
gatagagcat tgtaattatt gctcttcaac gaggaattcc tagtaagcgc aagtcatcag   1200
cttgcgttga ttacgtccct gcc                                          1223

SEQ ID NO: 40          moltype = DNA   length = 1563
FEATURE                Location/Qualifiers
source                 1..1563
                       mol_type = genomic DNA
                       organism = Candida tropicalis
variation              69
                       note = n is a, c, g, or t
variation              627
                       note = n is a, c, g, or t
variation              631
                       note = n is a, c, g, or t
variation              674
                       note = n is a, c, g, or t
variation              684
                       note = n is a, c, g, or t
variation              699
                       note = n is a, c, g, or t
variation              704
                       note = n is a, c, g, or t
variation              723..822
                       note = n is a, c, g, or t
variation              866
                       note = n is a, c, g, or t
```

| variation | 1014 |
| | note = n is a, c, g, or t |
| variation | 1509 |
| | note = n is a, c, g, or t |
| variation | 1542 |
| | note = n is a, c, g, or t |

SEQUENCE: 40

```
atgcttgtct caagattaag ccatgcatgt ctaagtataa gcaatttata cagtgaaact   60
gcgaatggnt cattaaatca gttatcgttt atttgatagt accttactac ttggataacc  120
gtggtaattc tagagctaat acatgcttaa aatcccgact gttttggaagg gatgtattta  180
ttagataaaa aatcaatgtc ttcggactct ttgatgattc ataataactt ttcgaatcgc  240
atggccttgt gctggcgatg gttcattcaa atttctgccc tatcaacttt cgatggtagg  300
atagtggcct accatggttt caacgggtaa cggggaataa gggttcgatt ccggagaggg  360
agcctgagaa acggctacca catccaagga aggcagcagg cgcgcaaatt acccaatccc  420
gacacgggga ggtagtgaca ataaataacg atacagggcc ctttcgggtc ttgtaattgg  480
aatgagtaca atgtaaatac cttaacgagg aacaattgga gggcaagtct ggtgccagca  540
gcccgcggta attccagctt caaaagccgt atattaaagg tggttgcagt taaaaagctc  600
gtagttgaac cttgggtttt ggttggnccg nccatctttc tgaagcctac tggacccaa  660
cccgagccct ttcntttggc taanccttt ggcgaaccng gactttacc tttgaaaaaa  720
ttnnnnnnnn nnnnnnnnnn nnnnnnnnnn nnnnnnnnnn nnnnnnnnnn nnnnnnnnnn  780
nnnnnnnnnn nnnnnnnnnn nnnnnnnnnn nnnnnnnnnn nncgattagg gatcggttgt  840
tgttcttaa ttgacgccat tgggcnccett acgagaaatc aaaagtcttt gggttctggg  900
ggaagtatgg tcgcaaggtt gaaacttaa aggaattgac ggaagggcac caccaggagt  960
ggagcctgcg ggcttaattt gactcaacac ggggaaactc accaggtcca gacncaataa 1020
ggattgacag attgagagct ctttcttgat tttgtgggtg gtggtgcatg gccgttctta 1080
gttggtggag tgatttgtct gcttaattgc gataacgaac gagaccttaa cctactaaat 1140
agtgctgcta gcatttgctg gtatagtcac ttcttagagg gactatcgat ttcaagtcga 1200
tggaagtttg aggcaataac aggtctgtga tgcccttaga cgttctgggc cgcacgcgcg 1260
ctacactgac ggagccagcg agtataaacc ttggccgaga ggtctgggaa atcttgtgaa 1320
actccgtcgt gctggggata gagcattgta attgttgctc ttcaacgagg aattcctagt 1380
aagcgcaagt catcagcttg cgttgattac gtccctgccc tttgtacaca ccgcccgtcg 1440
ctactaccga ttgaatggct tagtgaggct tccggattgg tttaggaaag ggggcaactc 1500
cattctggna ccgagaagct agtcaaactc ggtcatttag ancaagtaaa agtcgaacaa 1560
ggt                                                                1563
```

| SEQ ID NO: 41 | moltype = DNA   length = 1801 |
| FEATURE | Location/Qualifiers |
| source | 1..1801 |
| | mol_type = genomic DNA |
| | organism = Cryptococcus neoformans |

SEQUENCE: 41

```
acctggttga tcctgccagt agtcatatgc ttgtctcaaa gattaagcca tgcatgtcta   60
agtataaacg aattcatact gtgaaactgc gaatggctca ttaaatcagt tatagtttat  120
ttgatggtat cttgctacat ggataactgt ggtaattcta gagctaatac atgctgaaaa  180
gccccgactt ctggaagggg tgtatttatt agataaaaaa ccaatggggtt tcggccctct  240
atggtgaatc ataataactt ctcgaatcgc atggccttgt gccggcgatg cttcattcaa  300
atatctgccc tatcaacttt cgatggtagt atagaggcct accatggtat caacgggtaa  360
cggggaatta gggttcgatt ccggagaggg agcctgagaa acggctacca catccaagga  420
aggcagcagg cgcgcaaatt acccaatccc gacacgggga ggtagtgaca ataaataaca  480
atacagggct ttttgggcc ttgtaattgg aatgagtaca atttaaatcc cttaacgagg  540
aacaactgga gggcaagtct ggtgccagca gccgcggtaa ttccagctcc agtagcgtat  600
attaaagttg ttgcagttaa aaagctcgta gtcgaacttc aggtctgcg aggcggtcct  660
cctcacggag tgcactgtct tgctggacct tacctcctgg tggtcctgta tgctctttac  720
tgggtgtgca ggggaaccag gaattttacc ttgaaaaaat tagagtgttc aaagcaggca  780
atcgcccgaa tacattagca tggaataata gaataggacg tgcggttcta ttttgttggt  840
ttctaggatc gccgtaatga ttaatagga cggtcggggg cattggtatt ccgttgctag  900
aggtgaaatt cttagattga cggaagacca acaactgcga aagcatttgc caaggacgtt  960
ttcattgatc aagaacgaag gttaggggat caaaaacgat tagataccgt tgtagtctta 1020
acagtaaacg atgccgacta gggatcggcc cacgtcaatc tctgactggg tcggcaccttt 1080
acgagaaatc aaagtctttg ggttctgggg ggagtatggt cgcaaggctg aaacttaaag 1140
gaattgacgg aagggcacca ccaggtgtgg agcctgcggc ttaatttgac tcaacacggg 1200
gaaactcacc aggtccagac atagtgagga ttgacagatt gatagctctt tcttgattct 1260
atgggtggtg gtgcatggcc gttcttagtt ggtggagtga tttgtctggt taattccgat 1320
aacgaacgag accttaacct gctaaatagt caggccggct ttggctgtc gtatgacttc 1380
ttagagggac tgtcgcgtc tagtcgacgg aagtttgagg caataacagg tctgtgatgc 1440
ccttagatgt tctgggccgc acgcgcgcta cactgactga gccagcgagt cttaccgcct 1500
tggccgagag gcctgggtaa tcttgtgaaa ctcagtcgtg ctgggatagg agcattgcaa 1560
ttattgctct tcaacgagga atacctagta agcgtgagtc accagctcgc gttgattacg 1620
tccctgccct ttgtacacac cgcccgtcgc tactaccgat tgaatggctt agtgagatct 1680
ccggattggc gttggggagc cggcaacggc accccttggc cgagaagttg atcaaacttg 1740
gtcatttaga ggaagtaaaa gtcgtaacaa ggtttccgta ggtgaacctg cggaaggatc 1800
a                                                                 1801
```

| SEQ ID NO: 42 | moltype = DNA   length = 1673 |
| FEATURE | Location/Qualifiers |
| source | 1..1673 |
| | mol_type = genomic DNA |
| | organism = Fusarium sp. |

SEQUENCE: 42

```
gcaattatac cgcgaaactg cgaatggctc attatataag ttatcgttta tttgatagta    60
ccttactact tggataaccg tggtaattct agagctaata catgctaaaa atcccgactt   120
cggaagggat gtatttatta gattaaaaac caatgccctt cggggctcac tggtgattca   180
tgataactcc tcgaatcgca tggccttgtg ccggcgatgg ttcattcaaa tttcttccct   240
atcaacttc  gatgtttggg tattggccaa acatggtagc aacgggtaac ggagggttag   300
ggctcgaccc cggagaagga gcctgagaaa cggctactac atccaaggaa ggcagcaggc   360
gcgcaaatta cccaatcccg acacggggag gtagtgacaa taaatactga tacagggctc   420
ttttgggtct tgtaattgga atgagtacaa tttaaatccc ttaacgagga acaattggag   480
ggcaagtctg gtgccagcag ccgcggtaat tccagctcca atagcgtata ttaaagttgt   540
tgtggttaaa aagctcgtag ttgaaccttg ggcctggccg tccggtccgc ctcaccgcgt   600
gtactggctc ggccgggcct ttccctctgt ggaaccccat gcccttcact gggcgtggcg   660
gggaaacagg acttttactg tgaaaaaatt agagtgctcc aggcaggcct atgctcgaat   720
acattagcat ggaataatag aataggacgt gtggttctat tttgttggtt tctaggaccg   780
ccgtaatgat taatagggac agtcgggggc atcagtattc aagtcaga ggtgaaattc   840
ttggatttat tgaagactaa ctactgcgaa agcatttgcc aaggatgttt tcattaatca   900
ggaacgaaag ttaggggatc gaagacgatc agataccgtc gtagtcttaa ccataaacta   960
tgccgactag ggatcggacg tgttattttt ttgacccgtt cggcacctta cgagaaatca  1020
aagtgcttgg gctccagggg gagtatggtc gcaaggctga aacttaaaga aattgacgga  1080
agggcaccac caggggtgga gcctgcggct taatttgact caacacgggg aaactcacca  1140
ggtccagaca caatgaggat tgacagattg agagctcttt cttgattttg tgggtggtgg  1200
tgcatggccg ttcttagttg gtggagtgat ttgtctgctt aattgcgata acgaacgaga  1260
ccttaacctg ctaaatagcc cgtattgctt tggcagtacg ctggcttctt agagggacta  1320
tcggctcaag ccgatggaag tttgaggcaa taacaggtcc gtgatgccct tagatgttct  1380
gggccgcacg cgcgctacac tgacggagcc agcgagtact tccttgtccg aaaggtccgg  1440
gtaatcttgt taaactccgt cgtgctgggg atagagcatt gcaattattg ctcttcaacg  1500
aggaatcccct agtaagcgca agtcatcagc ttgcgttgat tacgtccctg ccctttgtac  1560
acaccgcccg tcgctactac cgattgaatg gctcagtgag gcgtccggac tggcccagag  1620
aggtgggcaa ctaccactca gggccggaaa gctctccaaa ctcggtcatt aga          1673

SEQ ID NO: 43         moltype = DNA  length = 1554
FEATURE               Location/Qualifiers
source                1..1554
                      mol_type = genomic DNA
                      organism = Bacillus anthracis
SEQUENCE: 43
ttattggaga gtttgatcct ggctcaggat gaacgctggc ggcgtgccta atacatgcaa    60
gtcgagcgaa tggattaaga gcttgctctt atgaagttag cggcggacgg gtgagtaaca   120
cgtgggtaac ctgcccataa gactgggata actccgggaa accggggcta ataccggata   180
acattttgaa ccgcatggtt cgaaattgaa aggcggcttc ggctgtcact tatggatgga   240
cccgcgtcgc attagctagt tggtgaggta acggctcacc aaggcaacga tgcgtagccg   300
acctgagagg gtgatcggcc acactgggac tgagacacgg cccagactcc tacgggaggc   360
agcagtaggg aatcttccgc aatggacgaa agtctgacgg agcaacgccg cgtgagtgat   420
gaaggctttc gggtcgtaaa actctgttgt tagggaagaa caagtgctag ttgaataagc   480
tggcaccttg acggtaccta accagaaagc cacggctaac tacgtgccag cagccgcggt   540
aatacgtagg tggcaagcgt tatccggaat tattgggcgt aaagcgcgcg caggtggttt   600
cttaagtctg atgtgaaagc ccacggctca accgtggagg gtcattggaa actgggagac   660
ttgagtgcag aagaggaaag tggaattcca tgtgtagcgg tgaaatgcgt agagatatgg   720
aggaacacca gtggcgaagg cgactttctg gtctgtaact gacactgagg cgcgaaagcg   780
tggggagcaa acaggattag ataccctggt agtccacgcc gtaaacgatg agtgctaagt   840
gttagagggt ttccgccctt tagtgctgaa gttaacgcat taagcactcc gcctggggag   900
tacggccgca aggctgaaac tcaaaggaat tgacgggggc ccgcacaagc ggtggagcat   960
gtggtttaat tcgaagcaac gcgaagaacc ttaccaggtc ttgacatcct ctgacaaccc  1020
tagagatagg gcttctcctt cgggagcaga gtgacaggtg gtgcatggtt gtcgtcagct  1080
cgtgtcgtga gatgttgggt taagtcccgc aacgagcgca acccttgatc ttagttgcca  1140
tcattwagtt gggcactcta aggtgactgc cggtgacaaa ccggaggaag gtggggatga  1200
cgtcaaatca tcatgcccct tatgacctgg gctacacacg tgctacaatg gacggtacaa  1260
agagctgcaa accgcgagg tggagctaat ctcataaaac cgttctcagt tcggattgta  1320
ggctgcaact cgcctacatg aagctggaat cgctagtaat cgcggatcag catgccgcgg  1380
tgaatacgtt cccgggcctt gtacacaccg cccgtcacac cacgagagtt gtaacaccc  1440
gaagtcgtg gggtaaccct tttggagcca gccgcctaag tgggacagca tgattggggt  1500
gaagtcgtaa caaggtagcc gtatcggaag gtgcggctgg atcacctcct ttct         1554

SEQ ID NO: 44         moltype = DNA  length = 1610
FEATURE               Location/Qualifiers
source                1..1610
                      mol_type = genomic DNA
                      organism = Burkholderia pseudomallei
SEQUENCE: 44
tctagatgcg tgctcgagcg gccgcccagt gctgcatgga tatctgctga attcggcttg    60
agcagtttga tcctggctca gattgaacgc tggcggcatg ccttacacat gcaagtcgaa   120
cggcagcacg ggcttcggcc tggtggcgag tggcggacgg gtgagttata tcggagca    180
tgtcctgtag tggggatag cccggcgaaa gccgaattaa taccgcatac gatctgagga   240
tgaaagcggg ggaccttcgg gcctcgcgct atagggttgg ccgatggctg attagctagt   300
tggtgggta aggcctacc aaggcgacga tcagtagctg gtctgagagg acgaccagcc   360
acactgggac tgagacacgg cccagactcc tacgggaggc agcagtgggg aattttggac   420
aatgggcgca agcctgatcc agcaatgccg cgtgtgtgaa gaaggccttc gggttgtaaa   480
gcactttgt ccggaaagaa atcattctgg ctaatacccg gagtggatga cggtaccgga   540
agaataagca ccggctaact acgtgccagc agccgcggta atacgtaggg tgcgagcgtt   600
aatcggaatt actgggcgta aagcgtgcgc aggcggtttg ctaagaccga tgtgaaatcc   660
```

-continued

```
ccgggctcaa cctgggaact gcattggtga ctggcaggct agagtatggc agagggggt   720
agaattccac gtgtagcagt gaaatgcgta gagatgtgga ggaataccga tggcgaaggc   780
agccccctgg gccaatactg acgctcatgc acgaaagcgt ggggagaaaa caggattaga   840
taccctggta gtccacgccc taaacgatgt caactagttg ttggggattc atttccttag   900
taacgtagct aacgcgcgaa gttgaccgcc tggggagtac ggtcgcaaga ttaaaactca   960
aaggaattga cggggacccg cacaagcggt ggatgatgtg gattaattcg atgcaacgcg  1020
aaaaacctta cctaccttg acatggtcgg aagcccgatg agagtgggc gtgctcgaaa   1080
gagaaccggc gcacaggtgc tgcatggctg tcgtcagctc gtgtcgtgag atgttgggtt  1140
aagtcccgca acgagcgcaa cccttgtcct tagttgctac gcaagagcac tctaaggaga  1200
ctgccggtga caaccggag gaaggtgggg atgacgtcaa gtcctcatgg cccttatggg   1260
tagggcttca cacgtcatac aatggtcgga acagagggtc gccaaccgc gagggggagc   1320
caatcccaga aaaccgatcg tagtccggat tgcactctgc aactcgagtg catgaagctg  1380
gaatcgctag taatcgcgga tcagcatgcc gcggtgaata cgttcccggg tcttgtacac  1440
accgcccgtc acaccatggg agtgggtttt accagaagtg gctagtctaa ccgcaaggag  1500
gacggtcacc acgtaggat tcatgactgg ggtgaagtcg taacaaggta gccgtagaag  1560
ccgaattcca gcacactggc ggccgttact actggatccg agctcgtacc             1610
```

| SEQ ID NO: 45 | moltype = DNA  length = 1511 |
|---|---|
| FEATURE | Location/Qualifiers |
| source | 1..1511 |
| | mol_type = genomic DNA |
| | organism = Clostridium botulinum |
| variation | 1..7 |
| | note = n is a, c, g, or t |

SEQUENCE: 45
```
nnnnnnngag agtttgatcc tggctcagga cgaacgctgg cggcgtgctt aacacatgca    60
agtcgagcga tgaagcttcc ttcgggaagt ggattagcgg cggacgggtg agtaacacgt   120
gggtaacctg cctcaaagtg ggggatagcc ttccgaaagg aagattaata ccgcataata   180
taagagaatc gcatgatttt cttatcaaag atttattgct ttgagatgga cccgcggcgc   240
attagctagt tggtaaggta acggcttacc aaggcaacga tgcgtagccg acctgagagg   300
gtgatcggcc acattggaac tgagacacgg tccagactcc tacggaggc agcagtgggg   360
aatattgcgc aatgggggag accctgacgc agcaacgccg cgtgggtgat gaaggtcttc   420
ggattgtaaa gccctgtttt ctaggacgat aatgacggta ctagaggagg aagccacggc   480
taactacgtg ccagcagccg cggtaatacg taggtgcga gcgttgtccg gatttactgg   540
gcgtaaaggg tgcgtaggcg gatgtttaag tgggatgtga atccccggg cttaacctgg   600
gggctgcatt ccaaactgga tatctagagt gcaggagagg aaagcggaat tcctagtgta   660
gcggtgaaat gcgtagagat taggaagaac accagtggcg aaggcggctt ctggactgt   720
aactgacgct gaggcacgaa agcgtgggta gcaaacagga ttagatacc tggtagtcca   780
gccgtaaac gatggatact aggtgtaggg ggtatcaact cccctgtgc cgcagttaac   840
acaataagta tccgcctgg ggagtacggt cgcaagatta aaactcaaag gaattgacgg   900
gggcccgcac aagcagcgga gcatgtggtt taattcgaag caacgcgaag aaccttacct   960
ggacttgaca tcccttgcat agcctagaga taggtgaagc ccttcgggc aaggagacag  1020
gtggtgcatg gttgtcgtca gctcgtgtcg tgagatgtta ggttaagtcc tgcaacgagc  1080
gcaacccttg ttattagttg ctaccattaa gttgagcact ctaatgagac tgcctgggta  1140
accaggagga aggtggggat gacgtcaaat catcatgccc cttatgtcca gggctacaca  1200
cgtgctacaa tggtaggtac aataagacg aagaccgtga ggtggagcaa aacttataaa  1260
acctatctca gttcggattg taggctgcaa ctcgcctaca tgaagctgga gttgctagta  1320
atcgcgaatc agaatgtcgc ggtgaatacg ttcccgggcc ttgtacacac cgccccgtca  1380
caccatgaga gctggtaaca cccgaagtcc gtgaggtaac cgtaaggagc cagcggccga  1440
aggtgggatt agtgattggg gtgaagtcgt aacaaggtag ccgtaggaga acctgcggct  1500
ggatcacctc c                                                        1511
```

| SEQ ID NO: 46 | moltype = DNA  length = 1510 |
|---|---|
| FEATURE | Location/Qualifiers |
| source | 1..1510 |
| | mol_type = genomic DNA |
| | organism = Clostridium botulinum |
| variation | 1..7 |
| | note = n is a, c, g, or t |

SEQUENCE: 46
```
nnnnnnngag agtttgatcc tggctcagga cgaacgctgg cggcgtgctt aacacatgca    60
agtcgagcga tgaagcttcc ttcgggaagt ggattagcgg cggacgggtg agtaacacgt   120
gggtaacctg cctcaaagtg ggggatagcc ttccgaaagg aagattaata ccgcataaca   180
taagagaatc gcatgatttt cttatcaaag atttattgct ttgagatgga cccgcggcgc   240
attagctagt tggtaaggta acggcttacc aaggcaacga tgcgtagccg acctgagagg   300
gtgatcggcc acattggaac tgagacacgg tccagactcc tacggaggc aggagtgggg   360
aatattgcgc aatgggggaa accctgacgc agcaacgccg cgtgggtgat gaaggtcttc   420
ggattgtaaa gccctgtttt ctaggacgat aatgacggta ctagaggagg aagccacggc   480
taactacgtg ccagcagccg cggtaatacg taggtgcga gcgttgtccg gatttactgg   540
gcgtaaaggg tgcgtaggcg gatgtttaag tgggatgtga atccccggg cttaacctgg   600
gggctgcatt ccaaactgga tatctagagt gcaggagagg aaagcggaat tcctagtgta   660
gcggtgaaat gcgtagagat taggaagaac accagtggcg aaggcggctt ctggactgt   720
aactgacgct gaggcacgaa agcgtgggta gcaaacagga ttagatacc tggtagtcca   780
gccgtaaac gatggatact aggtgtaggg ggtatcaact cccctgtgc cgcagttaac   840
acaataagta tccgcctgg ggagtacggt cgcaagatta aaactcaaag gaattgacgg   900
gggcccgcac aagcagcgga gcatgtggtt taattcgaag caacgcgaag aaccttacct   960
ggacttgaca tcccttgcat agcctagaga taggtgaagc ccttcgggc aaggagacag  1020
gtggtgcatg gttgtcgtca gctcgtgtcg tgagatgtta ggttaagtcc tgcaacgagc  1080
gcaacccttg ttattagttg ctaccattaa gttgagcact ctaatgagac tgcctgggta  1140
```

```
accaggagga aggtggggat gacgtcaaat catcatgccc cttatgtcca gggctacaca    1200
cgtgctacaa tggtaggtac aataagacgc aagaccgtga ggtggagcaa aacttataaa    1260
acctatctca gttcggattg taggctgcaa ctcgcctaca tgaagctgga gttgctagta    1320
atcgcgaatc agaatgtcgc ggtgaatacg ttcccgggcc ttgtacacac cgcccgtcac    1380
accatgagag ctggtaacac ccgaagtccg tgaggtaacc gtaaggagcc agcggccgaa    1440
ggtgggatta gtgattgggg tgaagtcgta acaaggtagc cgtaggagaa cctgcggctg    1500
gatcacctcc                                                          1510

SEQ ID NO: 47           moltype = DNA  length = 1516
FEATURE                 Location/Qualifiers
source                  1..1516
                        mol_type = genomic DNA
                        organism = Clostridium botulinum
variation               1..7
                        note = n is a, c, g, or t
SEQUENCE: 47
nnnnnnngag agtttgatcc tggctcagga cgaacgtggc ggcgtgccta acacatgcaa     60
gtcgagcgat gaagcttcct tcggggagtg gattagcggc ggacgggtga gtaacacgtg    120
ggtaacctgc ctcaaagagg gggatagcct cccgaaaggg agattaatac cgcataacat    180
tattttatgg catcatagaa taatcaaagg agcaatccgc tttgattatg acccgcgtc    240
gcattagcta gttggtgagg taacggctca ccaaggcaac gatgcgtagc cgacctgaga    300
gggtgatcgg ccacattgga actgagacac ggtccaact cctacgggag gcagcagtga    360
ggaatattgc gcaatggggg aaaccctgac gcagcaacgc cgcgtgagtg atgaaggttt    420
tcggatcgta aaactctgtc tttagggacg ataatgacgg tacctaagga ggaagccacg    480
gctaactacg tgccagcagc cgcggtaata cgtaggtggc aagcgttgtc cggatttact    540
gggcgtaaag agtatgtagg tgggtgctta agtcagatgt gaaattcccg ggcttaacct    600
gggcgctgca tttgaaactg gcatctaga gtgcaggaga ggaaagtgga attcctagtg    660
tagcggtgaa atgcgtagag attaggaaga acaccagtgg cgaaggcgac tttctggact    720
gtaactgaca ctgagatacg aaagcgtggg tagcaaacag gattagatcc cctggtagt    780
ccacgccgta aacgatgaat actaggtgtc gggggtacc accctcggtg ccgcagcaaa    840
cgcattaagt attccgcctg gggagtacgg tcgcaagatt aaaactcaaa ggaattgacg    900
gggacccgca caagcagcgg agcatgtggt ttaattcgaa gcaacgcgaa gaaccttacc    960
tagacttgac atctcctgaa ttactcttaa tcgaggaagt cccttcgggg acaggaaga   1020
caggtggtgc atggttgtcg tcagctcgtg tcgtgagatg ttgggttaag tcccgcaacg   1080
agcgcaaccc ttattgttag ttgctactat taagttaagc actctaacga gactgccgcg   1140
gttaacgtag aggaaggtgg ggatgacgtc aaatcatcat gccccttatg tctagggcta   1200
cacacgtgct acaatggctg gtacaacgag cagcaaaccc gcgaggggga gcaaaacttg   1260
aaagccagtc ccagttcgga ttgtaggctg aaactcgcct acatgaagtt ggagttgcta   1320
gtaatcgcgg aatcagcatg tcgcggtgaa tacgttcccg ggtcttgtac acaccgcccg   1380
tcacaccatg agagccggta acacccgaag cccgtgaggt aaccgtaagg agccagcggt   1440
cgaaggtggg attggtgatt ggggtgaagt cgtaacaagg tagccgtagg agaacctgcg   1500
gttggatcac ctcctt                                                  1516

SEQ ID NO: 48           moltype = DNA  length = 1516
FEATURE                 Location/Qualifiers
source                  1..1516
                        mol_type = genomic DNA
                        organism = Clostridium botulinum
variation               1..7
                        note = n is a, c, g, or t
variation               373
                        note = n is a, c, g, or t
variation               789..790
                        note = n is a, c, g, or t
SEQUENCE: 48
nnnnnnngag agtttgatcc tggctcagga cgaacgctgg cggcgtgcct aacacatgca     60
agtcgagcga tgaagcttcc ttcgggaagt ggattagcgg cggacgggtg agtaacacgt    120
gggtaacctg cctcaaagag tgggatagcc tcccgaaagg gagattaata ccgcataaca    180
ttattttatg gcatcataca taaaataatc aaaggagcaa tccgctttga gatgaccccg    240
cggcgcatta gctagttggt gaggtaacgg ctcaccaagg caacgatgcg tagccgacct    300
gagagggtga tcggccacat ggaactgag acacggtcca gactcctacg ggaggcagca    360
gtggggaata ttncgcaatg ggggaaaccc tgacgcagca acgccgcgtg agtgatgaag    420
gttttcggat cgtaaaactc tgtctttagg gacgataatg acggtaccta aggaggaagc    480
cacggctaac tacgtgccag cagccgcggt aatacgtagg tggcaagcgt tgtccggatt    540
tactgggcgt aaagagtatg taggtgggtg cttaagtcag atgtgaaatt cccgggctca    600
acctgggagc tgcatttgaa actgggcatc tagagtgcag gagaggaaag tggaattcct    660
agtgtagcgg tgaaatgcgt agagattagg aagaacacca gtggcgaagg cgactctctg    720
gactgtaact gacactgaga tacgaaagcg tgggtagcaa acaggattag ataccctggt    780
agtccacgnn gtaaacgatg aatactaggt gtcgggggt accaccctcg gtgccgcaac    840
aaacgcatta agtattccgc ctgggaagta cggtcgcaag attaaaactc aaaggaattg    900
acggggcccg cacaagcagc ggagcatgtg gtttaattcg aagcaacgcg aagaacctta    960
cctagacttg acatctcctg aattactctt aatcgaggaa gtcccttcgg ggacaggaag   1020
acaggtggtg catggttgtc gtcagctcgt gtcgtgagat gttgggttaa gtcccgcaac   1080
gagcgcaacc cttattgtta gttgctacta ttaagttaag cactctaacg agactgccgc   1140
ggttaacgta ggaggaaggtg gggatgacgt caaatcatca tgcccttat gtctagggct   1200
acacacgtgc tacaatggct ggtacaacga gcagcaaacc cgcgagggga gcaaaacttt   1260
gaaagccagt cccagttcgg attgtaggct gaaactcgcc tacatgaagt tggagttgct   1320
agtaatcgcg aatcagcatg tcgcggtgaa tacgttcccg ggtcttgtac accgcccgg   1380
tcacaccatg agagccggta acacccgaag cccgtgaggt aaccgtaagg agccagcggt   1440
```

```
cgaaggtggg attggtgatt ggggtaagtc gtaacaaggt agccgtagga gaacctgcgg   1500
ctggatcacc tcctttt                                                  1516

SEQ ID NO: 49           moltype = DNA   length = 1513
FEATURE                 Location/Qualifiers
source                  1..1513
                        mol_type = genomic DNA
                        organism = Clostridium botulinum
variation               1..7
                        note = n is a, c, g, or t
SEQUENCE: 49
nnnnnnnaga gtttgatcct ggctcaggac gaacgctggc ggcgtgccta acacatgcaa   60
tcgagcgatg aagcttcctt cgggaagtgg attagcggcg gacgggtgag taacacgtgg   120
gtaacctgcc tcatagaggg gaatagcctc ccgaaaggga gattaatacc gcataaagta   180
tgaaggtcgc atgacttcat tataccaaag gagtaatccg ctatgagatg gacccgcggc   240
gcattagcta gttggtgagg taagggctca ccaaggcaac gatgcgtagc cgacctgaga   300
gggtgatcgg ccacattgga actgagacac ggtccagact cctacgggag gcagcagtgg   360
ggaatattgc gcaatgggcg aaaccctgac gcagcaacgc cgcgtgaatg aagaaggcct   420
tagggttgta aagttctgtc atatgggaag ataatgacgg taccatatga ggaagccacg   480
gctaactacg tgccagcagc cgcggtaata cgtaggtggc aagcgttgtc cggatttact   540
gggcgtaaag gatgcgtagg cggacattta agtcagatgt gaaatacccg gctcaactt   600
gggtgctgca tttgaaactg gtgtctaga gtgcaggaga ggaaagcgga attcctagtg   660
tagcggtgaa atgcgtagag attaggaaga acaccagtgg cgaaggcggc tttctggact   720
gtaactgacg ctgaggcatg aaagcgtggg gagcaaacag gattagatac cctggtagtc   780
cacgccgtaa acgatgaata ctaggtgtag gaggtatcga ccccttctgt gccgcagtta   840
acacaataag tattccgcct ggggagtacg atcgcaagat taaaactcaa aggaattgac   900
gggggcccgc acaagcagcg gagcatgtgg tttaattcga agcaacgcga agaaccttac   960
ctagacttga catcccctga attacctgta atgaggaag cccttcgggg cagggagaca   1020
ggtggtgcat ggttgtcgtc agctcgtgtc gtgagatgtt gggttaagtc ccgcaacgag   1080
cgcaaccctt atcattagtt gctaccatta agttgagcac tctagtgaga ctgcccggt   1140
taaccgggag gaaggtgggg atgacgtcaa atcatcatgc cccttatgtc tagggctaca   1200
cacgtgctac aatggttggt acaacaagat gcaagaccgc gaggtggagc taaacttaaa   1260
aaaccaaccc agttcggatt gtaggctgaa actcgcctac atgaagccgg agttgctagt   1320
aatcgcgaat cagcatgtcg cggtgaatac gttcccgggc cttgtacaca ccgcccgtca   1380
caccatgaga gctggtaaca cccgaagtcc gtaggtaac cgtaaggagc cagcggccga   1440
aggtgggatt agtgattggg gtgaagtcgt aacaaggtag ccgtaggaga acctgcggtt   1500
ggatcacctc ctt                                                     1513

SEQ ID NO: 50           moltype = DNA   length = 1521
FEATURE                 Location/Qualifiers
source                  1..1521
                        mol_type = genomic DNA
                        organism = Francisella tularensis
SEQUENCE: 50
ttgaagagtt tgatcatggc tcagattgaa cgctggtggc atgcttaaca catgcaagtc   60
gaacggtaac aggtcttagg atgctgacga gtggcggacg ggtgagtaac gcgtaggaat   120
ctgcccattt gaggggggata ccagttggaa acgactgtta ataccgcata atatctgtg   180
attaaaggtg gctttcggcg tgtcgcagat ggatgagcct gcgttggatt agctagttgg   240
tggggtaagg gcccaccaag gctacgatcc atagctgatt tgagaggatg atcagccaca   300
ttgggactga gacacggccc aaactcctac gggaggcagc agtggggaat attggacaat   360
ggggcaacc ctgatccagc aatgccatgt gtgtgaagaa ggccctaggg ttgtaaagcct   420
ctttagttgg ggaggaaagc ctcaaggtta atagccttgg ggaggacgt tacccaaaga   480
ataagcaccg gctaactccg tgccagcagc cgcggtaata cggggggtgc aagcgttaat   540
cggaattact gggcgtaaag ggtctgtagg tggtttgtta agtcagatgt gaaagcccag   600
ggctcaacct tggaactgca tttgatactg gcaaactaga gtacggtaga ggaatgggga   660
atttctggtg tagcggtgaa atgcgtagag atcagaagga acaccaatgg cgaaggcaac   720
attctggacc gatactgaca ctgagggacg aaagcgtggg gatcaaacag gattagatac   780
cctggtagtc cacgctgtaa acgatgagta ctagctgttg gagtcggtgt aaaggctcta   840
gtggcgcacg taacgcgata agtactccgc ctggggacta cggccgcaag gctaaaactc   900
aaaggaattg acggggaccc gcacaagcgg tggagcatgt ggtttaattc gatgcaacgc   960
gaagaacctt acctggtctt gacatcctgc gaactttcta gagatagatt ggtgcttcgg   1020
aacgcagtga cagtgctgca cggctgtcgt cagctcgtgt tgtgaaatgt tgggttaagt   1080
cccgcaacga gcgcaacccc tattgatagt taccatcatt aagttgggta ctctattaag   1140
actgccgctg acaaggcgga ggaaggtggg gacgacgtca agtcatcatg gcccttacga   1200
ccagggctac acacgtgcta caatgggtat tacagagggt tgcgaaggtg cgagctggag   1260
cgaaactcaa aaaggtactc ttagtccgga ttgcagtctg caactcgact gcatgaagtc   1320
ggaatcgcta gtaatcgcag gtcagaatac tgcggtgaat acgttcccgg gtcttgtaca   1380
caccgcccgt cacaccatgg gagtgggttg ctccagaagt agatagctta acgaatgggc   1440
gtttaccacg gagtgattca tgactggggt gaagtcgtaa caaggtagc cgtagggaac   1500
ctgcggctgg atcacctcct t                                             1521

SEQ ID NO: 51           moltype = DNA   length = 1464
FEATURE                 Location/Qualifiers
source                  1..1464
                        mol_type = genomic DNA
                        organism = Vibrio cholerae
SEQUENCE: 51
tggctcagat tgaacgctgg cggcaggcct aacacatgca agtcgagcgg cagcacagag   60
gaacttgttc cttgggtggc gagcggcgga cgggtgagta atgcctggga aattgccggg   120
```

```
tagaggggga taaccattgg aaacgatggc taataccgca taacctcgta agagcaaagc    180
aggggacctt cgggccttgc gctaccggat atgcccaggt gggattagct agttggtgag    240
gtaagggctc accaaggcga cgatccctag ctggtctgag aggatgatca gccacactgg    300
aactgagaca cggtccagac tcctacggga ggcagcagtg gggaatattg cacaatgggc    360
gcaagcctga tgcagccatg ccgcgtgtat gaagaaggcc ttcgggttgt aaagtacttt    420
cagtagggag gaaggtggtt aagctaatac cttaatcatt tgacgttacc tacagaagaa    480
gcaccggcta actccgtgcc agcagccgcg gtaatacgga gggtgcaagc gttaatcgga    540
attactgggc gtaaagcgca tgcaggtggt ttgttaagtc agatgtgaaa gccctgggct    600
caacctagga atcgcatttg aaactgacaa gctagagtac tgtagagggg ggtagaattt    660
caggtgtagc ggtgaaatgc gtagagatct gaaggaatac cggtggcgaa ggcggccccc    720
tggacagata ctgacactca gatgcgaaag cgtggggagc aaacaggatt agataccctg    780
gtagtccacg ccgtaaacga tgtctacttg gaggttgtga cctagagtcg tggctttcgg    840
agctaacgcg ttaagtagac cgcctgggga gtacggtcgc aagattaaaa ctcaaatgaa    900
ttgacggggg cccgcacaag cggtggagca tgtggtttaa ttcgatgcaa cgcgaagaac    960
cttacctact cttgacatcc tcagaagaga ctggagacag tcttgtgcct tcgggaactg   1020
agagacaggt gctgcatggc tgtcgtcagc tcgtgttgtg aaatgttggg ttaagtcccg   1080
caacgagcgc aaccccttatc cttgtttgcc agcacgtaat ggtgggaact ccaggagac   1140
tgccgtgat aaaccggagg aaggtgggga cgacgtcaag tcatcatggc ccttacgagt   1200
agggctacac acgtgctaca atggcgtata cagagggcag cgataccgcg aggtggagcg   1260
aatctcacaa agtacgtcgt agtccggatt ggagtctgca actcgactcc atgaagtcgg   1320
aatcgctagt aatcgcaaat cagaatgttg cggtgaatac gttcccgggc cttgtacaca   1380
ccgcccgtca caccatggga gtgggctgca aaagaagcag gtagtttaac cttcgggagg   1440
acgcttgcca ctttgggtac ttgg                                          1464

SEQ ID NO: 52          moltype = DNA   length = 1469
FEATURE                Location/Qualifiers
source                 1..1469
                       mol_type = genomic DNA
                       organism = Yersinia pestis
SEQUENCE: 52
ctggcggcag gcctaacaca tgcaagtcga gcggcaccgg gaagtagttt actactttgc     60
cggcgagcgg cggacgggtg agtaatgtct ggggatctgc ctgatggagg gggataacta    120
ctggaaacgg tagctaatac cgcatgacct cgcaagagca agtggggga ccttagggcc     180
tcacgccatc ggatgaaccc agatgggatt agctagtagg tggggtaatg gctcacctag    240
gcgacgatcc ctagctggtc tgagaggatg accagccaca ctggaactga gacacgtggg    300
agactcctac gggaggcagc agtggggaat attgcacaat gggcgcaagc ctgatgcagc    360
catgccgcgt gtgtgaagaa ggccttcggg ttgtaaagca ctttcagcga ggaggaaggg    420
gttgagttta atacgctcaa tcattgacgt tactcgcaga agaagcaccg gctaactccg    480
tgccagcagc cgcggtaata ctgaggtgc aagcgttact cggaattact ccgcgtaaag    540
cgcacgcagg cggtttgtta agtcagatgt gaaatccccg cgcttaacgt gggaactgca    600
tttgaaactg gcaagctaga gtcttgtaga gggggtaga attccaggtg tagcggtgaa    660
atgcgtagag atctggagga ataccggtgg cgaaggcggc ccctggaca aagactgacg    720
ctcaggtgcg aaagcgtggg gagcaaacag gattagatac cctggtagtc cacgctgtaa    780
acgatgtcga cttggaggtt gtgcccttga ggcgtggctt ccggagctaa cgcgttaagt    840
cgaccgcctg gggagtacgg ccgcaaggtt aaaactcaaa tgaattgacg ggggcccgca    900
caagcggtgg agcatgtggt ttaattcgat gcaacgcgaa gaaccttacc tactcttgac    960
atccacagaa tttggcagag atgctaaagt gccttcgtgc actgtgagac aggtgctgca   1020
tggctgtcgt cagctcgtgt tgtgaaatgt tgggttaagt cccgcaacga gcgcaaccct   1080
tatcctttgt tgccagcacg taatggtggg aactcaaggg agactgccgg tgacaaaccg   1140
gaggaaggtg ggatgacgt caagtcatca tggcccttac gagtagggct acacacgtgc   1200
tacaatggca gatacaaagt gaagcgaact cgcgagagcc agcggaccac ataaagtctg   1260
tcgtagtccg gattggagtc tgcaactcga ctccatgaag tcggaatcgc tagtaatcgt   1320
agatcagaat gctacggtga atacgttccc gggccttgta cacaccgccc gtcacaccat   1380
gggagtgggt tgcaaaagaa gtaggtagct aaccttcgg gagggcgctt accactttgt   1440
gattcatgac tggggtgaag tcgtaacaa                                     1469

SEQ ID NO: 53          moltype = DNA   length = 24
FEATURE                Location/Qualifiers
misc_feature           1..24
                       note = Forward Primer
source                 1..24
                       mol_type = other DNA
                       organism = synthetic construct
SEQUENCE: 53
catccaagga aggcagcagg cgcg                                           24

SEQ ID NO: 54          moltype = DNA   length = 22
FEATURE                Location/Qualifiers
misc_feature           1..22
                       note = Reverse Primer
source                 1..22
                       mol_type = other DNA
                       organism = synthetic construct
SEQUENCE: 54
gttcaactac gagcttttta ac                                             22

SEQ ID NO: 55          moltype = DNA   length = 22
FEATURE                Location/Qualifiers
misc_feature           1..22
```

```
                        note = Reverse Primer
source                  1..22
                        mol_type = other DNA
                        organism = synthetic construct
SEQUENCE: 55
gttcgactac gagcttttta ac                                                22

SEQ ID NO: 56           moltype = DNA  length = 23
FEATURE                 Location/Qualifiers
misc_feature            1..23
                        note = Forward Primer
source                  1..23
                        mol_type = other DNA
                        organism = synthetic construct
SEQUENCE: 56
gtgtagcggt gaaatgcgta gag                                               23

SEQ ID NO: 57           moltype = DNA  length = 23
FEATURE                 Location/Qualifiers
misc_feature            1..23
                        note = Reverse Primer
source                  1..23
                        mol_type = other DNA
                        organism = synthetic construct
SEQUENCE: 57
tcgtttaccg tggactacca ggg                                               23
```